(12) United States Patent
Attie et al.

(10) Patent No.: US 6,207,640 B1
(45) Date of Patent: *Mar. 27, 2001

(54) TREATMENT OF PARTIAL GROWTH HORMONE INSENSITIVITY SYNDROME

(75) Inventors: Kenneth M. Attie, San Francisco, CA (US); Lena M. S. Carlsson, Gothenburg (SE); Neil Gesundheit, Los Altos; Audrey Goddard, San Francisco, both of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/643,212

(22) Filed: May 3, 1996

Related U.S. Application Data

(63) Continuation of application No. 08/410,452, filed on Mar. 24, 1995, now abandoned, and a continuation of application No. 08/224,982, filed on Apr. 7, 1994, now Pat. No. 5,646,113.

(51) Int. Cl.[7] ................................................ A61K 38/00
(52) U.S. Cl. ................................. 514/12; 514/21; 514/3; 530/303; 530/311; 530/399
(58) Field of Search ................................ 514/12, 21, 3; 530/303, 311, 399

(56) References Cited

U.S. PATENT DOCUMENTS

| | | | |
|---|---|---|---|
| 5,187,151 | * | 2/1993 | Clark et al. ................................ 514/3 |
| 5,646,113 | * | 7/1997 | Attie et al. ............................... 514/12 |
| 5,824,642 | * | 10/1998 | Attie et al. ............................... 514/12 |

FOREIGN PATENT DOCUMENTS

95/27495   10/1995   (WO) .

OTHER PUBLICATIONS

Mauras et al., "IGF–K Deficiency and Growth Failure: Association with Mutations in the Intracellular Domain of the Growth Hormone Receptor Gene," Joint Meeting of the American Pediatric Society and the Society for Pediatric Research, Washington, DC, (May 6–10, 1996) *Pediatric Research* 39(4 Part 2):93A Abstract No. 541 (1996).

Shimasaki et al., Progress in Growth Factor Res., vol. 3, pp 243–66 (1991).*

* cited by examiner

*Primary Examiner*—Dwayne C. Jones
*Assistant Examiner*—C. Delacroix-Muirheid
(74) *Attorney, Agent, or Firm*—Knobbe, Martens, Olson & Bear, LLP

(57) ABSTRACT

Methods for increasing the growth rate of a human patient having partial growth hormone insensitivity syndrome, but not Laron syndrome, are described. One such method comprises administering an effective dose of growth hormone, preferably growth hormone with a native human sequence, with or without an N-terminal methionine, to the patient. The patient is characterized as having a height of less than about −2 standard deviations below normal for age and sex, a serum level of high-affinity growth hormone binding protein that is at least 2 standard deviations below normal levels, a serum level of IGF-I that is below normal mean levels, and a serum level of growth hormone that is at least normal. In another such method, the same patient population is treated with an effective amount of IGF-I, given alone or in combination with an amount of growth hormone that is effective in combination with the IGF-I.

21 Claims, 38 Drawing Sheets

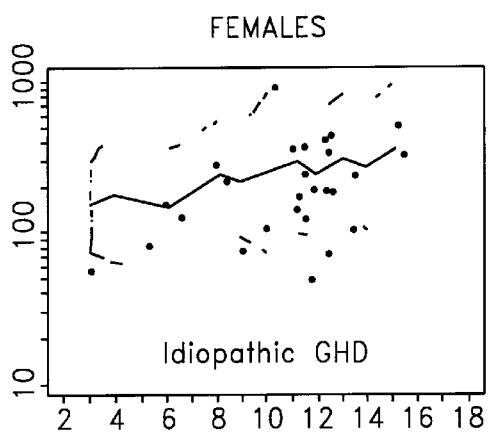
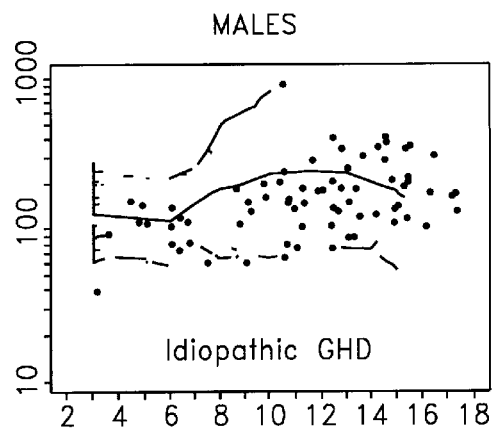
FIG. 1A  FIG. 1B
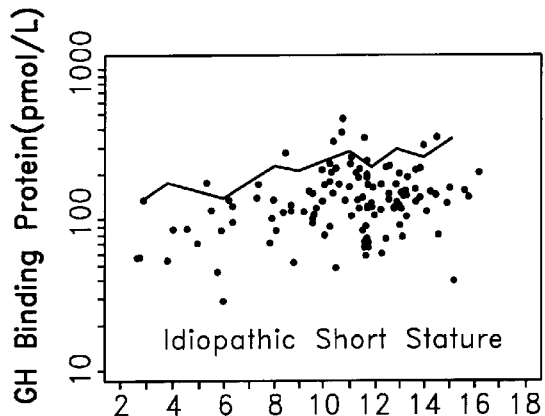
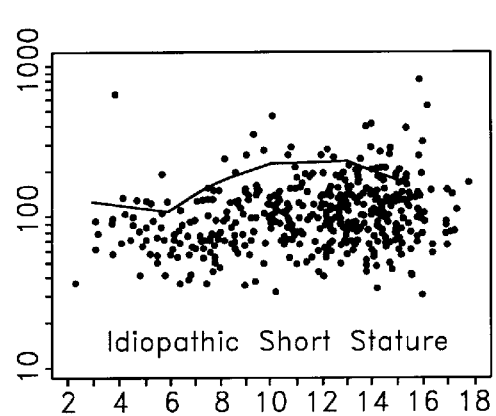
FIG. 1C  FIG. 1D
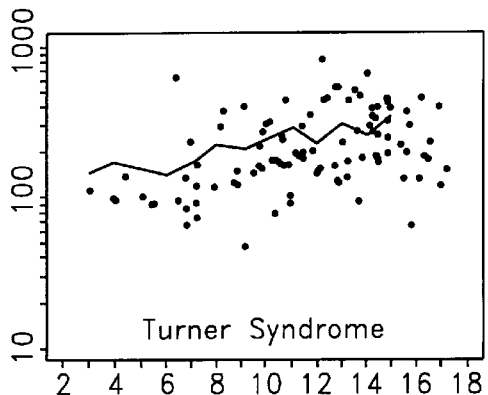
FIG. 1E

Patient 4
GHR RT-PCR Product
Exons 4-6

```
GHR allele 1    ATCCTCTAAG  GAGCCTAAAT  TCACCAAGTG  CCGTTCACCT  GAGCCAGAGA  CTTTTTCATG  CCACTGGACA
                 S  S  K      E  P  K  F   T  K  C      R  S  P      E  R  E  T     F  S  C       H  W  T
GHR allele 2    ATCCTCTAAG  GAGCCTAAAT  TCACCAAGTG  CCGTTCACCT  GAGCCAAAGA  CTTTTTCATG  CCACTGGACA
                 S  S  K      E  P  K  F   T  K  C      R  S  P      E  R [K] T      F  S  C       H  W  T GHR allele 1    GATGAGGTTC  ATCATGGTAC  AAAGAACCTA  GGACCCATAC  AGCTGTTCTA  TACCAGAAG|G  AACACTCAAG
                 D  E  V  H   H  G  T      K  N  L      G  P  I  Q     L  F  Y       T  R  R         N  T  Q  E
GHR allele 2    GATGAGGTTC  ATCATGGTAC  AAAGAACCTA  GGACCCATAC  AGCTGTTCTA  TACCAGAAG|G  AACACTCAAG
                 D  E  V  H   H  G  T      K  N  L      G  P  I  Q     L  F  Y       T  R  R         N  T  Q  E GHR allele 1    AATGGACTCA  AGAATGGAAA  GAATGCCCTG  ATTATGTTTC  TGCTGGGGAA  AACAGCTGTT  ACTTTAATTC
                 W  T  Q      E  W  K      E  C  P  D      Y  V  S      A  G  E       N  S  C  Y      F  N  S
GHR allele 2    AATGGACTCA  AGAATGGAAA  GAATGCCCTG  ATTATGTTTC  TGCTGGGGAA  AACAGCTGTT  ACTTTAATTC
                 W  T  Q      E  W  K      E  C  P  D      Y  V  S      A  G  E       N  S  C  Y      F  N  S GHR allele 1    ATCGTTTACC  TCCATCTGGA  TACCTTATTG  TATCAAGCTA  ACTAGCAATG  GTGGTACAGT  GGATGAAAAG
                 S  F  F      S  I  W  I    P  Y  C        I  K  L      T  S  N  G      G  T  V       D  E  K
GHR allele 2    ATCGTTTACC  TCCATCTGGA  TACCTTATTG  TATCAAGCTA  ACTAGCAATG  GTGGTACAGT  GGATGAAAAG
                 S  F  T      S  I  W  I    P  Y  C        I  K  L      T  S  N  G      G  T  V       D  E  K GHR allele 1    TCTTTCTCTG  TTGATGAAAT  AG|TGCCACCA  GATCCACCCA  TTGCCCTCAA  CTGGACTTTA  CTGAACGTCA
                 C  F  S  V    D  E  I       V | Q  P  P      D  P  P  I    A  L  N       W  T  L       L  N  V  S
GHR allele 2    TGTTTCTCTG  TTGATGAAAT  AG|TGCCACCA  GATCCACCCA  TTGCCCTCAA  CTGGACTTTA  CTGAACGTCA
                 C  F  S  V    D  E  I       V | Q  P  P      D  P  P  I    A  L  N       W  T  L       L  N  V  S GHR allele 1    GTTTAACTGG  GATTCATGCA  GATATCCAAG  TGAGATGGGA  AGCACCATGA  AATGCAGATA  TTCAGAAAGG
                 L  T  G      I  H  A      D  I  Q  V      R  W  E       A  P  R       N  A  D  I      Q  K  G
GHR allele 2    GTTTAACTGG  GATTCATGCA  GATATCCAAG  TGAGATGGGA  AGCACCACGC  AATGCAGATA  TTCAGAAAGG
                 L  T  G      I  H  A      D  I  Q  V      R  W  E       A  P [C]       N  A  D  I      Q  K  G GHR allele 1    GTGGATGGTT  CTGGAGTATG  AACTT
                 W  W  V      L  E  Y  E    L
GHR allele 2    GTGGATGGTT  CTGGAGTATG  AACTT
                 W  W  V      L  E  Y  E    L
```

FIG. 8

Patient 2
*GHR* GenoWic PCR Product
Exon 5

```
GHR allele 1  GAACACTCAA GAATGGACTC AAGAATGGAA AGAATGCCCT GATTATGTTT CTGCTGGGGA
              N  T  Q    E  W  T  Q    E  W  K      E  C  P      D  Y  V      A  G  E
GHR allele 2  GAACACTCAA GAATGGACTC AAGAATGGAA AGAATGCCCT GATTATGTTT CTGCTGGGGA
              N  T  Q    E  W  T  Q    E  W  K      E  C  P      D  Y  V      A  G  E GHR allele 1  AAACAGCTGT TACTTTAATT CATCGTTTAC CTCCATCTGG ATACCTTATT GTATCAAGCT
              N  S  C    Y  F  N  S    S  F  T      S  I  W      I  P  Y  C    I  K  L
GHR allele 2  AAACAGCTGT TACTTTAATT CATCGTTTAC CTCCATCTGG ATACCTTATT GTATCAAGCT
              N  S  C    Y  F  N  S    S  F  T      S  I  W      I  P  Y  C    I  K  L GHR allele 1  AACTAGCAAT GGTGGTACAG TGGATGAAAA GTGTTTCTCT GTTGATGAAA TAG
              T  S  N    G  G  T  V    D  E  K      C  F  S      V  D  E  I
GHR allele 2  AACTAGCAAT GGTGGTACAG TGGATGAAAA GTGATTCTCT GTTGATGAAA TAG
              T  S  N    G  G  T  V    D  E  K      * Stop
```

*FIG.9*

Patient 1
GHR Genomic PCR Product
Exon 7

| | | | | | | |
|---|---|---|---|---|---|---|
| GHR allele 1 | gactctttgg | ccaatatgcg | tttatatttt | gtcttgaaag | ATGGACCCTA<br>M D P | TATTGACAAC<br>I L T T |
| GHR allele 2 | gactctttgg | ccaatatgcg | tttatatttt | gtcttgaaag | ATGGACCCTA<br>M D P | TATTGACAAC<br>I L T T |
| GHR allele 1 | ATCAGTTCCA<br>S V P | GTGTACTCAT<br>V Y S L | TGAAAGTGGA<br>K V D | TAAGGAATAT<br>K E Y | GAAGTGCGTG<br>E V R V | TGAGATCCAA<br>R S K |
| GHR allele 2 | ATCAGTTCCA<br>S V P | GTGTACTCAT<br>V Y S L | TGAAAGTGGA<br>K V D | TAAGGAATAT<br>K E Y | GAAGTGCATG<br>E V [H] | TGAGATCCAA<br>R S K |
| GHR allele 1 | ACAACGAAAC<br>Q R N | TCTGGAAATT<br>S G N Y | ATGGCGAGTT<br>G E F | CAGTGAGGTG<br>S E V | CTCTATGTAA<br>L Y V T | CACTTCCTCA<br>L P Q |
| GHR allele 2 | ACAACGAAAC<br>Q R N | TCTGGAAATT<br>S G N Y | ATGGCGAGTT<br>G E F | CAGTGAGGTG<br>S E V | CTCTATGTAA<br>L Y V T | CACTTCCTCA<br>L P Q |
| GHR allele 1 | GATGAGCCAA<br>M S Q | TTTACATGTG<br>F T C | AAGAAG<br>E E | gtaa | aagaaataaa | agattaaaat agtagctaac |
| GHR allele 2 | GATGAGCCAA<br>M S Q | TTTACATGTG<br>F T C | AAGAAG<br>E E | gtaa | aagaaataaa | agattaaaat agtagctaac |

*FIG. 10*

Patient 7
GHR Genomic PCR Product
Exon 7

```
GHR allele 1    gactctttgg ccaatatgcg tttatatttt gtcttgaaag|ATGGACCCTA TATTGACAAC
                                                           M  D  P  I  L  T  T
GHR allele 2    gactctttgg ccaatatgcg tttatatttt gtcttgaaag|ATGGACCCTA TATTGACAAC
                                                           M  D  P  I  L  T  T GHR allele 1    ATCAGTTCCA GTGTACTCAT TGAAAGTGGA TAAGGAATAT GAAGTGCGTG TGAGATCCAA
                S  V  P  V  Y  S  L  K  V  D  K  E  Y  E  V  R  V  R  S  K
GHR allele 2    ATCAGTTCCA GTGTACTCAT TGAAAGTGGA TAAGGAATAT GAAGTGCGTG TGAGATCCAA
                S  V  P  V  Y  S  L  K  V  D  K  E  Y  E  V  R  V  R  S  K GHR allele 1    ACAACGAAAC TCTGGAAATT ATGGCGAGTT CAGTGAGGTG CTCTATGTAA CACTTCCTCA
                Q  R  N  S  G  N  Y  G  E  F  S  E  V  L  Y  V  T  L  P  Q
GHR allele 2    ACAACGAAAC TCTGGAAATT ATGGCGACTT CAGTGAGGTG CTCTATGTAA CACTTCCTCA
                Q  R  N  S  G  N  Y  G  [D] F  S  E  V  L  Y  V  T  L  P  Q GHR allele 1    GATGAGCCAA TTTACATGTG AAGAAG|gtaa aagaaataaa agattaaaat agtagctaac
                M  S  Q  F  T  C  E  E  E
GHR allele 2    GATGAGCCAA TTTACATGTG AAGAAG|gtaa aagaaataaa agattaaaat agtagctaac
                M  S  Q  F  T  C  E  E  E
```

FIG. 11

S473
Patients 13 and 44
GHR Genomic Exon 10 PCR Product

```
wild-type  gagttctttt tcatagatct tcatttttct tctatttttct agGAAGGAAA ATTAGAGAG
                                                          E  G  K   L  E  E
S473       gagttctttt tcatagatct tcatttttct tctatttttct agGAAGGAAA ATTAGAGAG
                                                          E  G  K   L  E  E wild-type  GTGAACACAA TCTTAGCCAT TCATGATAGC TATAAACCCG AATTCCACAG TGATGACTCT
            V  N  T  I   L  A  I    H  D  S   Y  K  P  E    F  H  S    D  D  S
S473       GTGAACACAA TCTTAGCCAT TCATGATAGC TATAAACCCG AATTCCACAG TGATGACTCT
            V  N  T  I   L  A  I    H  D  S   Y  K  P  E    F  H  S    D  D  S wild-type  TGGGTTGAAT TTATTGAGCT AGATATTGAT GAGCCAGATG AAAAGACTGA GGAATCAGAC
            W  V  E  F   I  E  L    D  I  D   E  P  D  E    K  T  E    E  S  D
S473       TGGGTTGAAT TTATTGAGCT AGATATTGAT GAGCCAGATG AAAAGACTGA GGAATCAGAC
            W  V  E  F   I  E  L    D  I  D   E  P  D  E    K  T  E    E  S  D wild-type  ACAGACAGAC TTCTAAGCAG TGACCATGAG AAATCACATA GTAACCTAGG GGTGAAGGAT
            T  D  R  L   L  S  S    D  H  E   K  S  H  S    N  L  G    V  K  D
S473       ACAGACAGAC TTCTAAGCAG TGACCATGAG AAATCACATA GTAACCTAGG GGTGAAGGAT
            T  D  R  L   L  S  S    D  H  E   K  S  H  S    N  L  G    V  K  D wild-type  GGCGACTCTG GACGTACCAG CTGTTGTGAA CCTGACATTC TGGAGACTGA TTTCAATGCC
            G  D  S  G   R  T  S    C  C  E   P  D  I  L    E  T  D    F  N  A
S473       GGCGACTCTG GACGTACCAG CTGTTGTGAA CCTGACATTC TGGAGACTGA TTTCAATGCC
            G  D  S  G   R  T  S    C  C  E   P  D  I  L    E  T  D    F  N  A wild-type  AATGACATAC ATGAGGGTAC CTCAGAGGTT GCTCAGCCAC AGAGGTTAAA AGGGGAAGCA
            N  D  I  H   E  G  T    S  E  V   A  Q  P  Q    R  L  K    G  E  A
S473       AATGACATAC ATGAGGGTAC CTCAGAGGTT GCTCAGCCAC AGAGGTTAAA AGGGGAAGCA
            N  D  I  H   E  G  T    S  E  V   A  Q  P  Q    R  L  K    G  E  A wild-type  GATCTCTTAT GCCTTGACCA GAAGAATCAA AATAACTCAC CTTATCATGA TGCTTGCCCT
            D  L  L  C   L  D  Q    K  N  Q   N  N  S  P    Y  H  D    A  C  P
S473       GATCTCTTAT GCCTTGACCA GAAGAATCAA AATAACTCAC CTTATCATGA TGCTTGCCCT
            D  L  L  C   L  D  Q    K  N  Q   N  N  S  P    Y  H  D    A  C  P
```

FIG. 12A

```
wild-type  GCTACTCAGC AGCCCAGTGT TATCCAAGCA GAGAAAAACA AACCACAACC ACTTCCTACT
           A  T  Q  Q   P  S  V     I  Q  A     E  K  N  K     P  Q  P     L  P  T
S473       GCTACTCAGC AGCCCAGTGT TATCCAAGCA GAGAAAAACA AACCACAACC ACTTCCTACT
           A  T  Q  Q   P  S  V     I  Q .A     E  K  N  K     P  Q  P     L  P  T wild-type  GAAGGAGCTG AGTCAACTCA CCAAGCTGCC CATATTCAGC TAAGCAATCC AAGTTCACTG
           E  G  A  E   S  T  H     Q  A  A     H  I  Q  L     S  N  P     S  S  L
S473       GAAGGAGCTG AGTCAACTCA CCAAGCTGCC CATATTCAGC TAAGCAATCC AAGTTCACTG
           E  G  A  E   S  T  H     Q  A  A     H  I  Q  L     S  N  P     S  S  L wild-type  TCAAACATCG ACTTTTATGC CCAGGTGAGC GACATTACAC CAGCAGGTAG TGTGGTCCTT
           S  N  I  D   F  Y  A     Q  V  S     D  I  T  P     A  G  S     V  V  L
S473       TCAAACATCG ACTTTTATGC CCAGGTGAGT GACATTACAC CAGCAGGTAG TGTGGTCCTT
           S  N  I  D   F  Y  A     Q  V  S     D  I  T  P     A  G  S     V  V  L wild-type  TCCCCGGGCC AAAAGAATAA GGGCAGGGATG TCCCAATGTG ACATGCACCC GGAAATGGTC
           S  P  G  Q   K  N  K     A  G  M     S  Q  C  D     M  H  P     E  M  V
S473       TCCCCGGGCC AAAAGAATAA GGGCAGGGATG TCCCAATGTG ACATGCACCC GGAAATGGTC
           S  P  G  Q   K  N  K     A  G  M     S  Q  C  D     M  H  P     E  M  V wild-type  TCACTCTGCC AAGAAAACTT CCTTATGGAC AATGCCTACT TCTGTGAGGC AGATGCCAAA
           S  L  C  Q   E  N  F     L  M  D     N  A  Y  F     C  E  A     D  A  K
S473       TCACTCTGCC AAGAAAACTT CCTTATGGAC AATGCCTACT TCTGTGAGGC AGATGCCAAA
           S  L  C  Q   E  N  F     L  M  D     N  A  Y  F     C  E  A     D  A  K wild-type  AAGTGCCTCC CTGTGGCTCC TCACATCAAG GTTGAATCAC ACATACAGCC AAGCTAAAC
           K  C  L  P   V  A  P     H  I  K     V  E  S  H     I  Q  P     S  L  N
S473       AAGTGCCTCC CTGTGGCTCC TCACATCAAG GTTGAATCAC ACATACAGCC AAGCTAAAC
           K  C  L  P   V  A  P     H  I  K     V  E  S  H     I  Q  P     S  L  N wild-type  CAAGAGGACA TTTACATCAC CACAGAAAGC CTTACCACTG CTGCTGGGAG GCCTGGGACA
           Q  E  D  I   Y  I  T     T  E  S     L  T  T  A     A  G  R     P  G  T
S473       CAAGAGGACA TTTACATCAC CACAGAAAGC CTTACCACTG CTGCTGGGAG GCCTGGGACA
           Q  E  D  I   Y  I  T     T  E  S     L  T  T  A     A  G  R     P  G  T wild-type  GGAGAACATG TTCCAGGTTC TGAGATGCCT GTCCCAGACT ATACCTCCAT TCATATAGTA
           G  E  H  V   P  G  S     E  M  P     V  P  D  Y     T  S  I     H  I  V
S473       GGAGAACATG TTCCAGGTTC TGAGATGCCT GTCCCAGACT ATACCTCCAT TCATATAGTA
           G  E  H  V   P  G  S     E  M  P     V  P  D  Y.    T  S  I     H  I  V
```

*FIG. 12B*

```
wild-type  CAGTCCCCAC AGGGCCTCAT ACTCAATGCG ACTGCCTTGC CCTTGCCTGA CAAAGAGTTT
           Q  S  P  Q  G  L  I  L  N  A  T  A  L  P  L  P  D  K  E  F
s473       CAGTCCCCAC AGGGCCTCAT ACTCAATGCG   ACTGCCTTGC CCTTGCCTGA CAAAGAGTTT
           Q  S  P  Q  G  L  I  L  N  A     T  A  L  P  L  P  D  K  E  F wild-type  CTCTCATCAT GTGGCTATGT GAGCACAGAC CAACTGAACA AAATCATGCC TTAGCCTTTC
           L  S  S  C  G  Y  V  S  T  D  Q  L  N  K  I  M  P
s473       CTCTCATCAT GTGGCTATGT GAGCACAGAC   CAACTGAACA AAATCATGCC TTAGCCTTTC
           L  S  S  C  G  Y  V  S  T  D     Q  L  N  K  I  M  P wild-type  TTTGG
s473       TTTGG
```

FIG.12C

A478T
Patient 13
GHR Genomic Exon 10 PCR Product

```
wild-type                                          gagtttcttt tcatagatct tcatttcctt agGAAGGAAA ATTAGAGGAG
                                                                                    E G K   L E E
A478T                                              gagtttcttt tcatagatct tcatttcctt agGAAGGAAA ATTAGAGGAG
                                                                                    E G K   L E E wild-type   GTGAACACAA TCTTAGCCAT TCATGATAGC TATAAACCCG AATTCCACAG TGATGACTCT
            V N T  I   L A I H D S  Y K P E   F H S   D D S
A478T       GTGAACACAA TCTTAGCCAT TCATGATAGC TATAAACCCG AATTCCACAG TGATGACTCT
            V N T  I   L A I H D S  Y K P E   F H S   D D S wild-type   TGGGTTGAAT TTATTGAGCT AGATATTGAT GAGCCAGATG AAAAGACTGA GGAATCAGAC
            W V E  F   I E L D I D  E P D E   K T E   E S D
A478T       TGGGTTGAAT TTATTGAGCT AGATATTGAT GAGCCAGATG AAAAGACTGA GGAATCAGAC
            W V E  F   I E L D I D  E P D E   K T E   E S D wild-type   ACAGACAGAC TTCTAAGCAG TGACCATGAG AAATCACATA GTAACCTAGG GGTGAAGGAT
            T D R  L   L S S D H E  K S H S   N L G   V K D
A478T       ACAGACAGAC TTCTAAGCAG TGACCATGAG AAATCACATA GTAACCTAGG GGTGAAGGAT
            T D R  L   L S S D H E  K S H S   N L G   V K D wild-type   GGCGACTCTG GACGTACCAG CTGTGTGAA  CCTGACATTC TGGAGACTGA TTTCAATGCC
            G D S  G   R T S C C E  P D I L   E T D   F N A
A478T       GGCGACTCTG GACGTACCAG CTGTGTGAA  CCTGACATTC TGGAGACTGA TTTCAATGCC
            G D S  G   R T S C C E  P D I L   E T D   F N A wild-type   AATGACATAC ATGAGGGTAC CTCAGAGGTT GCTCAGCCAC AGAGGTTAAA AGGGGAAGCA
            N D I  H   E G T S E V  A Q P Q   R L K   G E A
A478T       AATGACATAC ATGAGGGTAC CTCAGAGGTT GCTCAGCCAC AGAGGTTAAA AGGGGAAGCA
            N D I  H   E G T S E V  A Q P Q   R L K   G E A wild-type   GATCTCTTAT GCCTTGACCA GAAGAATCAA AATAACTCAC CTTATCATGA TGCTTGCCCT
            D L C   L D Q  K N Q    N N S P   Y H D   A C P
A478T       GATCTCTTAT GCCTTGACCA GAAGAATCAA AATAACTCAC CTTATCATGA TGCTTGCCCT
            D L C   L D Q  K N Q    N N S P   Y H D   A C P
```

FIG. 13A

```
wild-type  GCTACTCAGC AGCCCAGTGT TATCCAAGCA GAGAAAACA AACCACAACC ACTTCCTACT
           A  T  Q  Q  P  S  V    I  Q  A     E  K  N  K  P  Q  P    L  P  T
A478T      GCTACTCAGC AGCCCAGTGT TATCCAAGCA GAGAAAACA AACCACAACC ACTTCCTACT
           A  T  Q  Q  P  S  V    I  Q  A     E  K  N  K  P  Q  P    L  P  T wild-type  GAAGGAGCTG AGTCAACTCA CCAAGCTGCC CATATTCAGC TAAGCAATCC AAGTTCACTG
           E  G  A  E  S  T  H    Q  A  A     H  I  Q  L  S  N  P    S  S  L
A478T      GAAGGAGCTG AGTCAACTCA CCAAGCTGCC CATATTCAGC TAAGCAATCC AAGTTCACTG
           E  G  A  E  S  T  H    Q  A  A     H  I  Q  L  S  N  P    S  S  L wild-type  TCAAACATCG ACTTTTATGC CCAGTGAGAC GACATTACAC CAGCAGGTAG TGTGGTCCTT
           S  N  I  D  F  Y  A    Q  V  S     D  I  T  P  A  G  S    V  V  L
A478T      TCAAACATCG ACTTTTATGC CCAGTGAGAC GACATTACAC CAGCAGGTAG TGTGGTCCTT
           S  N  I  D  F  Y  A    Q  V  S     D  I  T  P  A  G  S    V  V  L wild-type  TCCCCGGGCC AAAAGAATAA GGCAGGGATG TCCCAATGTG ACATGCACCC GGAAATGGTC
           S  P  G  Q  K  N  K    A  G  M     S  Q  C  D  M  H  P    E  M  V
A478T      TCCCCGGGCC AAAAGAATAA GGCAGGGATG TCCCAATGTG ACATGCACCC GGAAATGGTC
           S  P  G  Q  K  N  K    A  G  M     S  Q  C  D  M  H  P    E  M  V wild-type  TCACTCTGCC AAGAAAACTT CCTTATGGAC AATGCCTACT TCTGTGAGGC AGATGCCAAA
           S  L  C  Q  E  N  F    L  M  D     N  A  Y  F  C  E  A    D  A  K
A478T      TCACTCTGCC AAGAAAACTT CCTTATGGAC AATGCCTACT TCTGTGAGGC AGATGCCAAA
           S  L  C  Q  E  N  F    L  M  D     N  A  Y  F  C  E  A    D  A  K wild-type  AAGTGCCTCC CTGTGGCTCC TCACACATCAAG GTTGAATCAC ACATACAAGCC AAGCTTAAAC
           K  C  L  P  V  A  P    H  I  K     V  E  S  H  I  Q  P    S  L  N
A478T      AAGTGCCTCC CTGTGGCTCC TCACACATCAAG GTTGAATCAC ACATACAAGCC AAGCTTAAAC
           K  C  L  P  V  A  P    H  I  K     V  E  S  H  I  Q  P    S  L  N wild-type  CAAGAGGACA TTTACATCAC CACAGAAAGC CTTACCACTG CTGCTGGGAG GCCTGGGACA
           Q  E  D  I  Y  I  T    T  E  S     L  T  T  A  A  G  R    P  G  T
A478T      CAAGAGGACA TTTACATCAC CACAGAAAGC CTTACCACTG CTGCTGGGAG GCCTGGGACA
           Q  E  D  I  Y  I  T    T  E  S     L  T  T  A  A  G  R    P  G  T wild-type  GGAGAACATG TTCCAGGTTC TGAGATGCCT GTCCCAGACT ATACCTCCAT TCATATAGTA
           G  E  H  V  P  G  S    E  M  P     V  P  D  Y  T  S  I    H  I  V
A478T      GGAGAACATG TTCCAGGTTC TGAGATGCCT GTCCCAGACT ATACCTCCAT TCATATAGTA
           G  E  H  V  P  G  S    E  M  P     V  P  D  Y  T  S  I    H  I  V
```

FIG.13B

```
wild-type  CAGTCCCCAC AGGGCCTCAT ACTCAATGCG ACTGCCTTGC CCTTGCCTGA CAAAGAGTTT
           Q  S  P  Q   G  L  I   L  N  A    T  A  L  P   L  P  D    K  E  F
A478T      CAGTCCCCAC AGGGCCTCAT ACTCAATGCG ACTGCCTTGC CCTTGCCTGA CAAAGAGTTT
           Q  S  P  Q   G  L  I   L  N  A    T  A  L  P   L  P  D    K  E  F wild-type  CTCTCATCAT GTGGCTATGT GAGCACAGAC CAACTGAACA AAATCATGCC TTAGCCTTTC
           L  S  S  C   G  Y  V   S  T  D    Q  L  N  K   I  M  P
A478T      CTCTCATCAT GTGGCTATGT GAGCACAGAC CAACTGAACA AAATCATGCC TTAGCCTTTC
           L  S  S  C   G  Y  V   S  T  D    Q  L  N  K   I  M  P wild-type  TTTGG
A478T      TTTGG
```

FIG. 13C

```
                               C422F
                          Patients 27 and 32
                     GHR Genomic Exon 10 PCR Product wild-type  gagtttcttt tcatagatct tcattttctt tctattttct agGAAGGAAA ATTAGAGGAG
                                                          E  G  K  L  E  E
C422F      gagtttcttt tcatagatct tcattttctt tctattttct agGAAGGAAA ATTAGAGGAG
                                                          E  G  K  L  E  E wild-type  GTGAACACAA TCTTAGCCAT TCATGATAGC TATAAACCCG AATTCCACAG TGATGACTCT
            V  N  T  I  L  A  I  H  D  S  Y  K  P  E  F  H  S  D  D  S
C422F      GTGAACACAA TCTTAGCCAT TCATGATAGC TATAAACCCG AATTCCACAG TGATGACTCT
            V  N  T  I  L  A  I  H  D  S  Y  K  P  E  F  H  S  D  D  S wild-type  TGGGTTGAAT TTATTGAGCT AGATATTGAT GAGCCAGATG AAAAGACTGA GGAATCAGAC
            W  V  E  F  I  E  L  D  I  D  E  P  D  E  K  T  E  E  S  D
C422F      TGGGTTGAAT TTATTGAGCT AGATATTGAT GAGCCAGATG AAAAGACTGA GGAATCAGAC
            W  V  E  F  I  E  L  D  I  D  E  P  D  E  K  T  E  E  S  D wild-type  ACAGACAGAC TTCCTAAGCAG TGACCATGAG AAATCACATA GTAACCTAGG GGTGAAGGAT
            T  D  R  L  L  S  S  D  H  E  K  S  H  S  N  L  G  V  K  D
C422F      ACAGACAGAC TTCCTAAGCAG TGACCATGAG AAATCACATA GTAACCTAGG GGTGAAGGAT
            T  D  R  L  L  S  S  D  H  E  K  S  H  S  N  L  G  V  K  D wild-type  GGCGACTCTG GACGTACCAG CTGTTGTGAA CCTGACATTC TGGAGACTGA TTTCAATGCC
            G  D  S  G  R  T  S  C  C  E  P  D  I  L  E  T  D  F  N  A
C422F      GGCGACTCTG GACGTACCAG CTGTTGTGAA CCTGACATTC TGGAGACTGA TTTCAATGCC
            G  D  S  G  R  T  S  C  C  E  P  D  I  L  E  T  D  F  N  A wild-type  AATGACATAC ATGAGGGTAC CTCAGAGGTT GCTCAGCCAC AGAGGTTAAA AGGGGAAGCA
            N  D  I  H  E  G  T  S  E  V  A  Q  P  Q  R  L  K  G  E  A
C422F      AATGACATAC ATGAGGGTAC CTCAGAGGTT GCTCAGCCAC AGAGGTTAAA AGGGGAAGCA
            N  D  I  H  E  G  T  S  E  V  A  Q  P  Q  R  L  K  G  E  A wild-type  GATCTCTTAT GCCTTGACCA GAAGAATCAA AATAACTCAC CTTATCATGA TGCTTGCCCT
            D  L  L  C  L  D  Q  K  N  Q  N  N  S  P  Y  H  D  A  C  P
C422F      GATCTCTTAT GCCTTGACCA GAAGAATCAA AATAACTCAC CTTATCATGA TGCTTTCCCT
            D  L  L  C  L  D  Q  K  N  Q  N  N  S  P  Y  H  D  A  F  P
```

FIG. 15A

```
wild-type  GCTACTCAGC AGCCCAGTGT TATCCAAGCA GAGAAAAACA AACCACAACC ACTTCCTACT
           A  T  Q  Q   P  S  V    I  Q  A    E  K  N  K    P  Q  P    L  P  T
C422F      GCTACTCAGC AGCCCAGTGT TATCCAAGCA GAGAAAAACA AACCACAACC ACTTCCTACT
           A  T  Q  Q   P  S  V    I  Q  A    E  K  N  K    P  Q  P    L  P  T wild-type  GAAGGAGCTG AGTCAACTCA CCAAGCTGCC CATATTCAGC TAAGCAATCC AAGTTCACTG
           E  G  A  E   S  T  H    Q  A  A    H  I  Q  L    S  N  P    S  S  L
C422F      GAAGGAGCTG AGTCAACTCA CCAAGCTGCC CATATTCAGC TAAGCAATCC AAGTTCACTG
           E  G  A  E   S  T  H    Q  A  A    H  I  Q  L    S  N  P    S  S  L wild-type  TCAAACATGC ACTTTTATGC CCAGGTGAGC GACATTACAC CAGCAGGTAG TGTGGTCCTT
           S  N  I  D   F  Y  A    Q  V  S    D  I  T  P    A  G  S    V  V  L
C422F      TCAAACATCG ACTTTTATGC CCAGGTGAGC GACATTACAC CAGCAGCTAG TGTGGTCCTT
           S  N  I  D   F  Y  A    Q  V  S    D  I  T  P    A  G  S    V  V  L wild-type  TCCCCGGGCC AAAAGAATAA GGCAGGGATG TCCCAATGTG ACATGCACCC GGAAATGGTC
           S  P  G  Q   K  N  K    A  G  M    S  Q  C  D    M  H  P    E  M  V
C422F      TCCCCGGGCC AAAAGAATAA GGCAGGGATG TCCCAATGTG ACATGCACCC GGAAATGGTC
           S  P  G  Q   K  N  K    A  G  M    S  Q  C  D    M  H  P    E  M  V wild-type  TCACTCTGCC AAGAAAACTT CCTTATGGAC AATGCCTACT TCTGTGAGGC AGATGCCAAA
           S  L  C  Q   E  N  F    L  M  D    N  A  Y  F    C  E  A    D  A  K
C422F      TCACTCTGCC AAGAAAACTT CCTTATGGAC AATGCCTACT TCTGTGAGGC AGATGCCAAA
           S  L  C  Q   E  N  F    L  M  D    N  A  Y  F    C  E  A    D  A  K wild-type  AAGTGCCTCC CTGTGGCTCC TCACATCAAG GTTGAATCAC ACATACAGCC AAGCTTAAAC
           K  C  L  P   V  A  P    H  I  K    V  E  S  H    I  Q  P    S  L  N
C422F      AAGTGCCTCC CTGTGGCTCC TCACATCAAG GTTGAATCAC ACATACAGCC AAGCTTAAAC
           K  C  L  P   V  A  P    H  I  K    V  E  S  H    I  Q  P    S  L  N wild-type  CAAGAGGACA TTTACATCAC CACAGAAAGC CTTACCACTG CTGCTGGGAG GCCTGGACA
           Q  E  D  I   Y  I  T    T  E  S    L  T  T  A    A  G  R    P  G  T
C422F      CAAGAGGACA TTTACATCAC CACAGAAAGC CTTACCACTG CTGCTGGGAG GCCTGGACA
           Q  E  D  I   Y  I  T    T  E  S    L  T  T  A    A  G  R    P  G  T wild-type  GGAGAACATG TTCCAGGTTC TGAGATGCCT GTCCCAGACT ATACCTCCAT TCATATAGTA
           G  E  H  V   P  G  S    E  M  P    V  P  D  Y    T  S  I    H  I  V
C422F      GGAGAACATG TTCCAGGTTC TGAGATGCCT GTCCCAGACT ATACCTCCAT TCATATAGTA
           G  E  H  V   P  G  S    E  M  P    V  P  D  Y    T  S  I    H  I  V
```

*FIG. 15B*

| | | | | | | |
|---|---|---|---|---|---|---|
| wild-type | CAGTCCCCAC | AGGGCCTCAT | ACTCAATGCG | ACTGCCTTGC | CCTTGCCTGA | CAAAGAGTTT |
| | Q S P | Q G L I | L N A | T A L P | L P D | K E F |
| C422F | CAGTCCCCAC | AGGGCCTCAT | ACTCAATGCG | ACTGCCTTGC | CCTTGCCTGA | CAAAGAGTTT |
| | Q S P | Q G L I | L N A | T A L P | L P D | K E F |
| | | | | | | |
| wild-type | CTCTCATCAT | GTGGCTATGT | GAGCACAGAC | CAACTGAACA | AAATCATGCC | TTAGCCTTTC |
| | L S S | C G Y V | S T D | Q L N K | I M P | |
| C422F | CTCTCATCAT | GTGGCTATGT | GAGCACAGAC | CAACTGAACA | AAATCATGCC | TTAGCCTTTC |
| | L S S | C G Y V | S T D | Q L N K | I M P | |
| | | | | | | |
| wild-type | TTTGG | | | | | |
| C422F | TTTGG | | | | | |

FIG.15C

P561T
Patients 27 and 32
GHR Genomic Exon 10 PCR Product

```
wild-type  gagtttcttt tcatagatct tcattttctt tctatttct agAAGGAAA ATTAGAGAG
                                                         E G K    L E E
P561T      gagtttcttt tcatagatct tcattttctt tctatttct agAAGGAAA ATTAGAGAG
                                                         E G K    L E E wild-type  GTGAACACAA TCTTAGCCAT TCATGATAGC TATAAACCCG AATTCCACAG TGATGACTCT
           V  N  T  I  L  A  I    H  D  S    Y  K  P  E  F  H  S    D  D  S
P561T      GTGAACACAA TCTTAGCCAT TCATGATAGC TATAAACCCG AATTCCACAG TGATGACTCT
           V  N  T  I  L  A  I    H  D  S    Y  K  P  E  F  H  S    D  D  S wild-type  TGGGTTGAAT TTATTGAGCT AGATATTGAT GAGCCAGATG AAAAGACTGA GGAATCAGAC
           W  V  E  F  I  E  L    D  I  D    E  P  D  E  K  T  E    E  S  D
P561T      TGGGTTGAAT TTATTGAGCT AGATATTGAT GAGCCAGATG AAAAGACTGA GGAATCAGAC
           W  V  E  F  I  E  L    D  I  D    E  P  D  E  K  T  E    E  S  D wild-type  ACAGACAGAC TTCTAAGCAG TGACCATGAG AAATCACATA GTAACCTAGG GGTGAAGGAT
           T  D  R  L  L  S  S    D  H  E    K  S  H  S  N  L  G    V  K  D
P561T      ACAGACAGAC TTCTAAGCAG TGACCATGAG AAATCACATA GTAACCTAGG GGTGAAGGAT
           T  D  R  L  L  S  S    D  H  E    K  S  H  S  N  L  G    V  K  D wild-type  GGCGACTCTG GACGTACCAG CTGTTGTGAA CCTGACATTC TGGAGACTGA TTTCAATGCC
           G  D  S  G  R  T  S    C  C  E    P  D  I  L  E  T  D    F  N  A
P561T      GGCGACTCTG GACGTACCAG CTGTTGTGAA CCTGACATTC TGGAGACTGA TTTCAATGCC
           G  D  S  G  R  T  S    C  C  E    P  D  I  L  E  T  D    F  N  A wild-type  AATGACATAC ATGAGGGTAC CTCAGAGGTT GCTCAGCCAC AGAGGTTAAA AGGGGAAGCA
           N  D  I  H  E  G  T    S  E  V    A  Q  P  Q  R  L  K    G  E  A
P561T      AATGACATAC ATGAGGGTAC CTCAGAGGTT GCTCAGCCAC AGAGGTTAAA AGGGGAAGCA
           N  D  I  H  E  G  T    S  E  V    A  Q  P  Q  R  L  K    G  E  A wild-type  GATCTCTTAT GCCTTGACCA GAAGAATCAA AATAACTCAC CTTATCATGA TGCTTGCCCT
           D  L  L  C  L  D  Q    K  N  Q    N  N  S  P  Y  H  D    A  C  P
P561T      GATCTCTTAT GCCTTGACCA GAAGAATCAA AATAACTCAC CTTATCATGA TGCTTGCCCT
           D  L  L  C  L  D  Q    K  N  Q    N  N  S  P  Y  H  D    A  C  P
```

FIG. 16A

| | | | | | | | |
|---|---|---|---|---|---|---|---|
|wild-type|GCTACTCAGC|AGCCCAGTGT|TATCCAAGCA|GAGAAAAACA|AACCACAACC|ACTTCCTACT| |
| |A T Q Q|P S V|I Q A|E K N K|P Q P|L P T| |
|P561T|GCTACTCAGC|AGCCCAGTGT|TATCCAAGCA|GAGAAAAACA|AACCACAACC|ACTTCCTACT| |
| |A T Q Q|P S V|I Q A|E K N K|P Q P|L P T| |
|wild-type|GAAGGAGCTG|AGTCAACTCA|CCAAGCTGCC|CATATTCAGC|TAAGCAATCC|AAGTTCACTG| |
| |E G A E|S T H|Q A A|H I Q L|S N P|S S L| |
|P561T|GAAGGAGCTG|AGTCAACTCA|CCAAGCTGCC|CATATTCAGC|TAAGCAATCC|AAGTTCACTG| |
| |E G A E|S T H|Q A A|H I Q L|S N P|S S L| |
|wild-type|TCAAACATCG|ACTTTTATGC|CCAGGTGAGC|GACATTACAC|CAGCAGGTAG|TGTGGTCCTT| |
| |S N I D|F Y A|Q V S|D I T P|A G S|V V L| |
|P561T|TCAAACATCG|ACTTTTATGC|CCAGGTGAGC|GACATTACAC|CAGCAGGTAG|TGTGGTCCTT| |
| |S N I D|F Y A|Q V S|D I T P|A G S|V V L| |
|wild-type|TCCCCGGGCC|AAAAGAATAA|GGCAGGGATG|TCCCAATGTG|ACATCACCCC|GGAAATGGTC| |
| |S P G Q|K N K|A G M|S Q C D|M H P|E M V| |
|P561T|TCCCCGGGCC|AAAAGAATAA|GGCAGGGATG|TCCCAATGTG|ACATCACCCC|GGAAATGGTC| |
| |S P G Q|K N K|A G M|S Q C D|M H P|E M V| |
|wild-type|TCACTCTGCC|AAGAAAACTT|CCTTATGAAC|AATGCCTACT|TCTGTGAGGC|AGATGCCAAA| |
| |S L C Q|E N F|L M D|N A Y F|C E A|D A K| |
|P561T|TCACTCTGCC|AAGAAAACTT|CCTTATGAAC|AATGCCTACT|TCTGTGAGGC|AGATGCCAAA| |
| |S L C Q|E N F|L M D|N A Y F|C E A|D A K| |
|wild-type|AAGTGCCTCC|CTGTGGCTCC|TCACATCAAG|GTTGAATCAC|ACATACAGCC|AAGCTTAAAC| |
| |K C L P|V A P|H I K|V E S H|I Q P|S L N| |
|P561T|AAGTGCCTCC|CTGTGGCTCC|TCACATCAAG|GTTGAATCAC|ACATACAGCC|AAGCTTAAAC| |
| |K C L P|V A P|H I K|V E S H|I Q P|S L N| |
|wild-type|CAAGAGGACA|TTTACATCAC|CACAGAAAGC|CTTACCACTG|CTGCTGGGAG|GCCTGGGACA| |
| |Q E D I|Y I T|T E S|L T T A|A G R|P G T| |
|P561T|CAAGAGGACA|TTTACATCAC|CACAGAAAGC|CTTACCACTG|CTGCTGGGAG|GACTGGGACA| |
| |Q E D I|Y I T|T E S|L T T A|A G R|D W T| |
|wild-type|GGAGAACATG|TTCCAGGTTC|TGAGATGCCT|GTCCCAGACT|ATACCTCCAT|TCATATAGTA| |
| |G E H V|P G S|E M P|V P D Y|T S I|H I V| |
|P561T|GGAGAACATG|TTCCAGGTTC|TGAGATGCCT|GTCCCAGACT|ATACCTCCAT|TCATATAGTA| |
| |G E H V|P G S|E M P|V P D Y|T S I|H I V| |

FIG. 16B

```
wild-type  CAGTCCCCAC AGGGCCTCAT ACTCAATGCG ACTGCCTTGC CCTTGCCTGA CAAAGAGTTT
           Q  S  P  Q  G  L  I   L  N  A    T  A  L  P   L  P  D    K  E  F
P561T      CAGTCCCCAC AGGGCCTCAT ACTCAATGCG ACTGCCTTGC CCTTGCCTGA CAAAGAGTTT
           Q  S  P  Q  G  L  I   L  N  A    T  A  L  P   L  P  D    K  E  F wild-type  CTCTCATCAT GTGGCTATGT GAGCACAGAC CAACTGAACA AAATCATGCC TTAGCCTTTC
           L  S  S  C  G  Y  V   S  T  D    Q  L  N  K   I  M  P
P561T      CTCTCATCAT GTGGCTATGT GAGCACAGAC CAACTGAACA AAATCATGCC TTAGCCTTTC
           L  S  S  C  G  Y  V   S  T  D    Q  L  N  K   I  M  P wild-type  TTTGG
P561T      TTTGG
```

FIG. 16C

T306P
Patients 44 and 49
GHR Genomic Exon 10 PCR Product

```
wild-type  gagtttcttt tcatagatct tcatttcttt tctatttct agGAAGAAA ATTAGAGGAG
                                                          E  G  K    L  E  E
T306P      gagtttcttt tcatagatct tcatttcttt tctatttct agGAAGAAA ATTAGAGGAG
                                                          E  G  K    L  E  E wild-type  GTGAACACAA TCTTAGCCAT TCATGATAGC TATAAACCCG AATTCCACAG TGATGACTCT
            V  N  T  I  L  A  I   H  D  S   Y  K  P  E  F  H  S   D  D  S
T306P      GTGAACCCAA TCTTAGCCAT TCATGATAGC TATAAACCCG AATTCCACAG TGATGACTCT
            V  N  P  I  L  A  I   H  D  S   Y  K  P  E  F  H  S   D  D  S wild-type  TGGGTTGAAT TTATTGAGCT AGATATTGAT GAGCCAGATG AAAAGACTGA GGAATCAGAC
            W  V  E  F  I  E  L   D  I  D   E  P  D  E  K  T  E   E  S  D
T306P      TGGGTTGAAT TTATTGAGCT AGATATTGAT GAGCCAGATG AAAAGACTGA GGAATCAGAC
            W  V  E  F  I  E  L   D  I  D   E  P  D  E  K  T  E   E  S  D wild-type  ACAGACAGAC TTCTAAGCAG TGACCATGAG AAATCACATA GTAACCTAGG GGTGAAGGAT
            T  D  R  L  L  S  S   D  H  E   K  S  H  S  N  L  G   V  K  D
T306P      ACAGACAGAC TTCTAAGCAG TGACCATGAG AAATCACATA GTAACCTAGG GGTGAAGGAT
            T  D  R  L  L  S  S   D  H  E   K  S  H  S  N  L  G   V  K  D wild-type  GGCGACTCTG GACGTACCAG CTGTTGTGAA CCTGACATTC TGGAGACTGA TTTCAATGCC
            G  D  S  G  R  T  S   C  C  E   P  D  I  L  E  T  D   F  N  A
T306P      GGCGACTCTG GACGTACCAG CTGTTGTGAA CCTGACATTC TGGAGACTGA TTTCAATGCC
            G  D  S  G  R  T  S   C  C  E   P  D  I  L  E  T  D   F  N  A wild-type  AATGACATAC ATGAGGGTAC CTCAGAGGTT GCTCAGCCAC AGAGGTTAAA AGGGGAAGCA
            N  D  I  H  E  G  T   S  E  V   A  Q  P  Q  R  L  K   G  E  A
T306P      AATGACATAC ATGAGGGTAC CTCAGAGGTT GCTCAGCCAC AGAGGTTAAA AGGGGAAGCA
            N  D  I  H  E  G  T   S  E  V   A  Q  P  Q  R  L  K   G  E  A wild-type  GATCTCTTAT GCCTTGACCA GAAGAATCAA AATAACTCAC CTTATCATGA TGCTTGCCCT
            D  L  L  C  L  D  Q   K  N  Q   N  N  S  P  Y  H  D   A  C  P
T306P      GATCTCTTAT GCCTTGACCA GAAGAATCAA AATAACTCAC CTTATCATGA TGCTTGCCCT
            D  L  L  C  L  D  Q   K  N  Q   N  N  S  P  Y  H  D   A  C  P
```

*FIG. 18A*

```
wild-type  GCTACTCAGC AGCCCAGTGT TATCCAAGCA GAGAAAAACA AACCACAACC ACTTCCTACT
           A  T  Q  Q  S  P  S  V  I  Q  A  E  K  N  K  P  Q  P  L  P  T
T306P      GCTACTCAGC AGCCCAGTGT TATCCAAGCA GAGAAAAACA AACCACAACC ACTTCCTACT
           A  T  Q  Q  P  S  V  I  Q  A  E  K  N  K  P  Q  P  L  P  T wild-type  GAAGGAGCTG AGTCAACTCA CCAAGCTGCC CATATTCAGC TAAGCAATCC AAGTTCACTG
           E  G  A  E  S  T  H  Q  A  A  H  I  Q  L  S  N  P  S  S  L
T306P      GAAGGAGCTG AGTCAACTCA CCAAGCTGCC CATATTCAGC TAAGCAATCC AAGTTCACTG
           E  G  A  E  S  T  H  Q  A  A  H  I  Q  L  S  N  P  S  S  L wild-type  TCAAACATCG ACTTTTATGC CCAAGTGAGC GACATTACAC CAGCAGGTAG TGTGGTCCTT
           S  N  I  D  F  Y  A  Q  V  S  D  I  T  P  A  G  S  V  V  L
T306P      TCAAACATCG ACTTTTATGC CCAAGTGAGC GACATTACAC CAGCAGGTAG TGTGGTCCTT
           S  N  I  D  F  Y  A  Q  V  S  D  I  T  P  A  G  S  V  V  L wild-type  TCCCCGGGCC AAAAGAATAA GGCAGGGATG TCCCAATGTG ACATGCACCC GGAAATGGTC
           S  P  G  Q  K  N  K  A  G  M  S  Q  C  D  M  H  P  E  M  V
T306P      TCCCCGGGCC AAAAGAATAA GGCAGGGATG TCCCAATGTG ACATGCACCC GGAAATGGTC
           S  P  G  Q  K  N  K  A  G  M  S  Q  C  D  M  H  P  E  M  V wild-type  TCACTCTGCC AAGAAAACTT CCTTATGGAC AATGCCTACT TCTGTGAGGC AGATGCCAAA
           S  L  C  Q  E  N  F  L  M  D  N  A  Y  F  C  E  A  D  A  K
T306P      TCACTCTGCC AAGAAAACTT CCTTATGGAC AATGCCTACT TCTGTGAGGC AGATGCCAAA
           S  L  C  Q  E  N  F  L  M  D  N  A  Y  F  C  E  A  D  A  K wild-type  AAGTGCCTCC CTGTGGCTCC TCACATCAAG GTTGAATCAC ACATACCACC AAGCTTAAAC
           K  C  L  P  V  A  P  H  I  K  V  E  S  H  I  Q  P  S  L  N
T306P      AAGTGCCTCC CTGTGGCTCC TCACATCAAG GTTGAATCAC ACATACAGCC AAGCTTAAAC
           K  C  L  P  V  A  P  H  I  K  V  E  S  H  I  Q  P  S  L  N wild-type  CAAGAGACA TTTACATCAC CACAGAAAGC CTTACCACTG CTGCTGGGAG GCCTGGGACA
           Q  E  D  I  Y  I  T  T  E  S  L  T  T  A  A  G  R  P  G  T
T306P      CAAGAGACA TTTACATCAC CACAGAAAGC CTTACCACTG CTGCTGGGAG GCCTGGGACA
           Q  E  D  I  Y  I  T  T  E  S  L  T  T  A  A  G  R  P  G  T wild-type  GGAGAACATG TTCCAGGTTC TGAGATGCCT GTCCCAGACT ATACCTCCAT TCATATAGTA
           G  E  H  V  P  G  S  E  M  P  V  P  D  Y  T  S  I  H  I  V
T306P      GGAGAACATG TTCCAGGTTC TGAGATGCCT GTCCCAGACT ATACCTCCAT TCATATAGTA
           G  E  H  V  P  G  S  E  M  P  V  P  D  Y  T  S  I  H  I  V
```

*FIG. 18B*

```
wild-type  CAGTCCCCCAC AGGGCCTCAT ACTCAATGCG ACTGCCTTGC CCTTGCCTGA CAAAGAGTTT
           Q  S  P  Q   G  L  I    L  N  A    T  A  L  P   L  P  D    K  E  F
T306P      CAGTCCCCCAC AGGGCCTCAT ACTCAATGCG ACTGCCTTGC CCTTGCCTGA CAAAGAGTTT
           Q  S  P  Q   G  L  I    L  N  A    T  A  L  P   L  P  D    K  E  F wild-type  CTCTCATCAT GTGGCTATGT GAGCACAGAC CAACTGAACA AAATCATGCC TTAGCCTTTC
           L  S  S  C  G  Y  V   S  T  D    Q  L  N  K   I  M  P    
T306P      CTCTCATCAT GTGGCTATGT GAGCACAGAC CAACTGAACA AAATCATGCC TTAGCCTTTC
           L  S  S  C  G  Y  V   S  T  D    Q  L  N  K   I  M  P wild-type  TTTGG
T306P      TTTGG
```

FIG. 18C

C518X
Patient 49
GHR Genomic Exon 10 PCR Product

| | | | | | |
|---|---|---|---|---|---|
| wild-type | | gagtttcttt | tcatagatct | tcatttcctt | tctattttct | agGAAGGAAA ATTAGAGGAG |
| | | | | | | E G K L E E |
| C518X | | gagtttcttt | tcatagatct | tcatttcctt | tctattttct | agGAAGGAAA ATTAGAGGAG |
| | | | | | | E G K L E E |

| wild-type | GTGAACACAA | TCTTAGCCAT | TCATGATAGC | TATAAACCCG | AATTCCACAG | TGATGACTCT |
| | V N T I | L A I | H D S | Y K P E | F H S | D D S |
| C518X | GTGAACACAA | TCTTAGCCAT | TCATGATAGC | TATAAACCCG | AATTCCACAG | TGATGACTCT |
| | V N T I | L A I | H D S | Y K P E | F H S | D D S |

| wild-type | TGGGTTGAAT | TTATTGAGCT | AGATATTGAT | GAGCCAGATG | AAAAGACTGA | GGAATCAGAC |
| | W V E F | I E L | D I D | E P D P | K T E | E S D |
| C518X | TGGGTTGAAT | TTATTGAGCT | AGATATTGAT | GAGCCAGATG | AAAAGACTGA | GGAATCAGAC |
| | W V E F | I E L | D I D | E P D P | K T E | E S D |

| wild-type | ACAGACAGAC | TTCTAAGCAG | TGACCATGAG | AAATCACATA | GTAACCTAGG | GGTGAAGGAT |
| | T D R L | S S | D H E | K S H S | N L G | V K D |
| C518X | ACAGACAGAC | TTCTAAGCAG | TGACCATGAG | AAATCACATA | GTAACCTAGG | GGTGAAGGAT |
| | T D R L | S S | D H E | K S H S | N L G | V K D |

| wild-type | GGCGACTCTG | GACGTACCAG | CTGTTGTGAA | CCTGACATTC | TGGAGACATTC | TTTCAATGCC |
| | G D S G | R T S | C C E | P D I L | E T D | F N A |
| C518X | GGCGACTCTG | GACGTACCAG | CTGTTGTGAA | CCTGACATTC | TGGAGACTGA | TTTCAATGCC |
| | G D S G | R T S | C C E | P D I L | E T D | F N A |

| wild-type | AATGACATAC | ATGAGGGTAC | CTCAGAGGTT | GCTCAGCCAC | AGAGGTTAAA | AGGGAAGCA |
| | N D I H | E G T | S E V | A Q P Q | R L K | G E A |
| C518X | AATGACATAC | ATGAGGGTAC | CTCAGAGGTT | GCTCAGCCAC | AGAGGTTAAA | AGGGAAGCA |
| | N D I H | E G T | S E V | A Q P Q | R L K | G E A |

| wild-type | GATCTCTTAT | GCCTTGACCA | GAAGAATCAA | AATAACTCAC | CTTATCATGA | TGCTTGCCCT |
| | D L L C | L D Q | K N Q | N N S P | Y H D | A C P |
| C518X | GATCTCTTAT | GCCTTGACCA | GAAGAATCAA | AATAACTCAC | CTTATCATGA | TGCTTGCCCT |

```
c518x       CAGTCCCCAC AGGGCCTCAT ACTCAATGCG ACTGCCTTGC CCTTGCCTGA CAAAGAGTTT
wild-type   CTCTCATCAT GTGGCTATGT GAGCACAGAC CAACTGAACA AAATCATGCC TTAGCCTTTC
            L   S   S   C   G   Y   V   S   T   D   Q   L   N   K   I   M   P
c518x       CTCTCATCAT GTGGCTATGT GAGCACAGAC CAACTGAACA AAATCATGCC TTAGCCTTTC wild-type   TTTGG
c518x       TTTGG
```

*FIG. 20C*

TREATMENT OF PARTIAL GROWTH HORMONE INSENSITIVITY SYNDROME

This application is a continuation of application U.S. Ser. No. 08/224,982 filed on Apr. 7, 1994, now U.S. Pat. No. 5,646,113 and Ser. No. 08/410,452 filed on Mar. 24, 1995, now abandoned, the full disclosures of which are incorporated herein by reference.

BACKGROUND OF THE INVENTION

1. Field of the Invention

This invention relates to a method for increasing the growth rates of human patients having partial growth hormone insensitivity syndrome.

2. Description of Background and Related Art

Most children with significant short stature do not have growth hormone (GH) deficiency as classically defined by the GH response to provocative stimuli. Once known causes of short stature have been excluded, these patients are classified with various terms, including familial short stature, constitutional delay of growth, or "idiopathic" short stature (ISS). Some of these children may not reach their genetic potential for height, although results from large-scale longitudinal studies have not been reported. Since there are so many factors that contribute to normal growth and development, it is likely that patients with ISS are heterogeneous with regard to their etiology of short stature. Despite not being classically GH deficient, most children with ISS respond to treatment with GH, although not as well.

Many investigators have searched for disturbances in spontaneous GH secretion in this set of patients. One hypothesis suggests that some of these patients have inadequate secretion of endogenous GH under physiologic conditions, but are able to demonstrate a rise in GH in response to pharmacologic stimuli, as in traditional GH stimulation tests. This disorder has been termed "GH neurosecretory dysfunction," and the diagnosis rests on the demonstration of an abnormal GH pattern on prolonged serum sampling. Numerous investigators have reported results of such studies, and have found this abnormality to be only occasionally present. Other investigators have postulated that these patients have "bioinactive GH;" however, this has not yet been demonstrated conclusively.

When the GH receptor (GHR) was cloned, it was shown that the major GH binding activity in blood was due to a protein which derives from the same gene as the GHR and corresponds to the extracellular domain of the full-length GHR. Most patients with growth hormone insensitivity (or Laron) syndrome (GHIS) lack growth hormone receptor binding activity and have absent or very low GH-binding protein (GHBP) activity in blood. Such patients have a mean height standard deviation score (SDS) of about −5 to −6, are resistant to GH treatment, and have increased serum concentrations of GH and low serum concentrations of insulin-like growth factor (IGF-I). They respond to treatment with IGF-I. In patients with defects in the extracellular domain of the GHR, the lack of functional GHBP in the circulation can serve as a marker for the GH insensitivity.

There is a subclass of patients with ISS having low GHBP in their blood who have a mean height SDS intermediate between patients with complete GHIS (Laron syndrome) and normal children, and who respond somewhat, but not completely, to GH treatment. This class of patients can be characterized as having partial GHIS.

It is an object of the present invention to identify a subset of patients with ISS who exhibit partial GHIS and do not have complete GHIS or Laron syndrome.

It is another object to treat this identified subset of patients so that they attain ultimate height consistent with their genetic potential as determined by the mid-parental target height.

These and other objects will be apparent to those of ordinary skill in the art.

SUMMARY OF THE INVENTION

Accordingly, in one aspect, the present invention provides a method for increasing the growth rate of a human patient having partial GHIS comprising administering an effective amount of GH to said patient, whereby said patient has a height less than about −2 standard deviations below normal for age and sex, has a serum level of high-affinity GHBP that is at least 2 standard deviations below normal levels, has a serum level of IGF-I that is below normal mean levels, and has a mean or maximum stimulated serum level of GH that is at least normal, wherein the patient does not have Laron syndrome. Preferably, the GH is human recombinant GH.

In another aspect, the invention provides a method for increasing the growth rate of a human patient having partial GHIS comprising administering an effective amount of IGF-I (preferably human recombinant IGF-I) to said patient, whereby said patient has a height less than about −2 standard deviations below normal for age and sex, has a serum level of high-affinity GHBP that is at least 2 standard deviations below normal levels, has a serum level of IGF-I that is below normal mean levels, and has a mean or maximum stimulated serum level of GH that is at least normal, wherein the patient does not have Laron syndrome.

In a further aspect, the invention supplies a method for increasing the growth rate of a human patient having partial GHIS comprising administering amounts of IGF-I and GH to said patient which amounts are effective in combination, whereby said patient has a height less than about −2 standard deviations below normal for age and sex, has a serum level of high-affinity GHBP that is at least 2 standard deviations below normal levels, has a serum level of IGF-I that is below normal mean levels, and has a mean or maximum stimulated serum level of GH that is at least normal, wherein the patient does not have Laron syndrome.

In a still further aspect, the present invention provides a method for increasing the growth rate of a human patient having partial GHIS whereby said patient has a heterogeneous (intracellular and/or extracellular) GHR gene defect comprising administering an effective amount of GH and/or IGF-I to said patient. Preferably, the GH is human recombinant GH and the IGF-I is human recombinant IGF-I.

In a still further aspect, the invention provides a method for increasing the growth rate of a human patient having partial GHIS comprising detecting whether the patient has a heterogeneous (intracellular and/or extracellular) GHR gene defect, and if so, administering an effective amount of GH and/or IGF-I to said patient.

BRIEF DESCRIPTION OF THE DRAWINGS

FIGS. 1A–1E shows serum GHBP concentrations in children in the Genentech National Cooperative Growth Study (NCGS) with growth hormone deficiency (GHD), ISS, and Turner syndrome (TS) standardized for age and sex and expressed as SDS, by age at the time of enrollment in the study. The shaded area represents the normal range (−2 SD to +2 SD) for each sex. The solid line indicates the normal mean for age and sex. Occasionally, points for two or more patients overlap and appear as a single point.

FIG. 8 shows the DNA sequences (SEQ ID NOS: 1 and 3, respectively) and predicted amino acid sequences (SEQ ID NOS: 2 and 4, respectively) of two GHR alleles in ISS Patient 4 (exons 4–6). The mutations in alleles 1 and 2 are boxed. The vertical bars indicate exon boundaries in the cDNA sequence.

FIG. 9 shows the DNA sequences (SEQ ID NOS: 5 and 7, respectively) and predicted amino acid sequences (SEQ ID NOS: 6 and 8, respectively) of two GHR alleles in ISS Patient 2 (exon 5). The mutation in allele 2 is boxed.

FIG. 10 shows the DNA sequences (SEQ ID NOS: 9 and 11, respectively) and predicted amino acid sequences (SEQ ID NOS: 10 and 12, respectively) of two GHR alleles in ISS Patient 1 (exon 7). The mutation in allele 2 is boxed. The intron sequence is given in lower-case letters and the exon sequence in upper-case lettering. The vertical bars indicate exon boundaries in the DNA sequence.

FIG. 11 shows the DNA sequences (SEQ ID NOS: 13 and 15, respectively) and predicted amino acid sequences (SEQ ID NOS: 14 and 16, respectively) of two GHR alleles in ISS Patient 7 (exon 7). The mutation in allele 2 is boxed. The intron sequence is given in lower-case letters and the exon sequence in upper-case lettering. The vertical bars indicate exon boundaries in the DNA sequence.

FIGS. 12A–12C, 13A–13C, 14, 15A–15C, 16A–16C, 17, 18A–18C, 19, 20A–20C and 21 show the analysis of the GHR gene for patients herein (SEQ ID NOS: 17–30), and demonstrate consequential inheritance from parents, as well as growth response data for various of the patients herein. See infra for further explanatory text.

Figure 2:
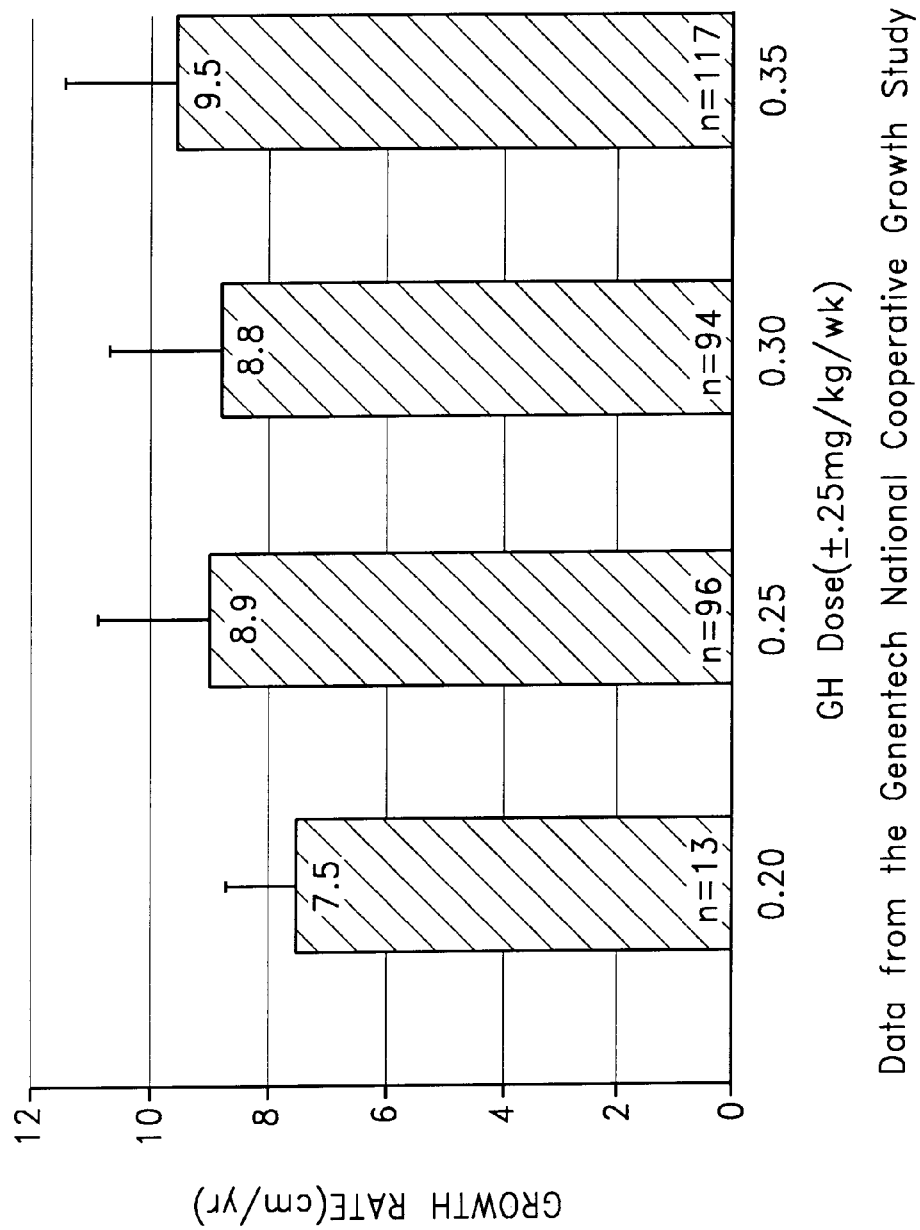
FIG. 2 shows the growth rate in cm/year of patients enrolled in the NCGS with ISS, treated with various doses of GH administered by daily injection.

(A) A 199 bp fragment containing exon 8 was amplified from the genomic DNA of affected patients 1 and 2, the mother (M) and father (F) of patient 1, and a control subject (WT) using oligonucleotide primers 8a and 8b. The mutation generates a MaeII site producing 2 fragments of 154 and 45 bp respectively. After 1 hr digestion with MaeII the DNA fragments were subject to polyacrylamide gel electrophoresis. The parents of patient 1 gave a mixed digestion pattern consistent with the presence of both wild-type and mutant alleles, whereas both patients bear only the mutant allele and the control DNA the wild-type allele only. ND—nondigested fragment. Mk=SIZE marker.

(B) Partial pedigree of the families of patients 1 and 2 demonstrating the inheritance of the mutant allele as determined by sequencing and restriction digestion of the PCR generated exon 8 fragment. The mutant allele is denoted 154 and the normal allele 199 (as in the restriction enzyme digest pattern). The data on the newborn sibling of patient 1 has not been shown but restriction digest of placental DNA revealed a pattern consistent with a heterozygous state.

Figure 24A:
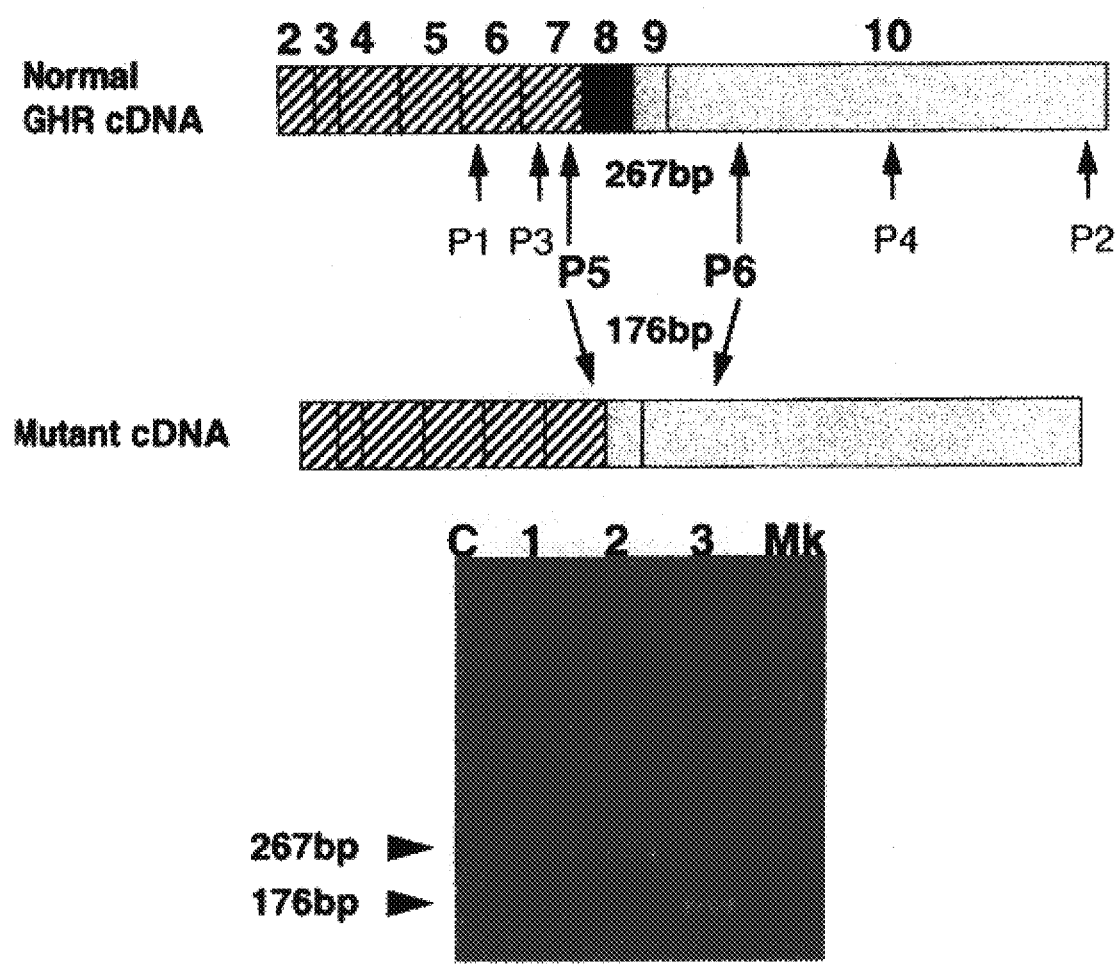
Figure 24B:
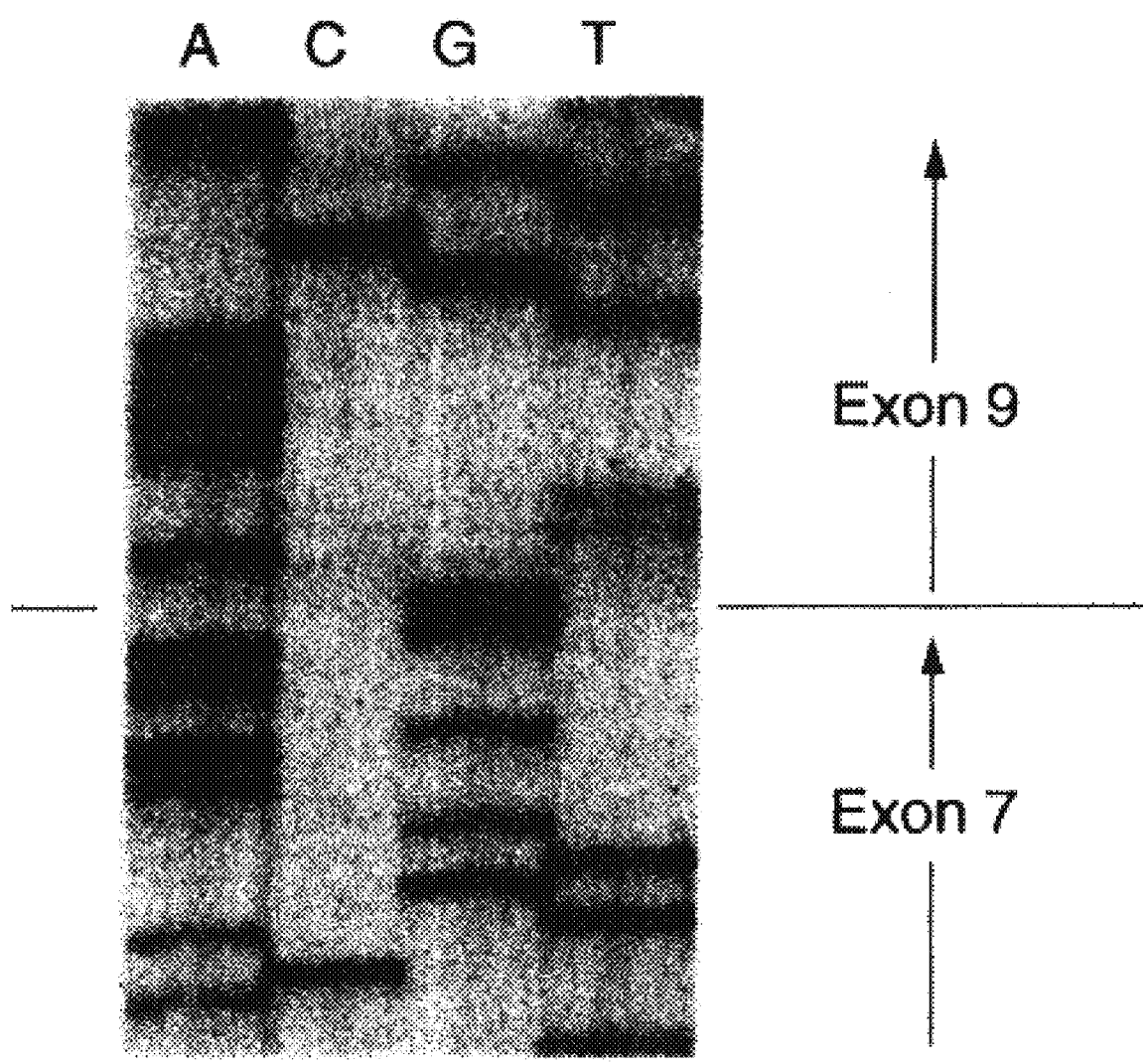

FIGS. 24(A and B) demonstrates the effect of the mutation on splicing of the GHR.

(A) RT-PCR was performed on RNA isolated from EBV transformed lymphocytes from patient 1 using the nested PCR technique depicted (Sequences of primers P1–P5 are listed in table 2). The last round of PCR using primers P5 and P6 amplified as expected a 267 bp fragment in the normally spliced GHR (lanes 1 and 2: normal control lymphocytes and liver respectively) whereas in patient 1 (lane 3) only a 176 bp product is obtained consistent with the skipping of the 91 bp exon 8. Mk=size marker, C=water control)

(B) Direct sequencing of these RT-PCR products confirmed the skipping of exon 8 in patient 1 with exon 7 splicing directly into exon 9 whereas in the control normal splicing of exon 7 into exon 8 occurs.

TABLE A

| Primer name | | Primer sequence 5'-3' | |
|---|---|---|---|
| 8a | | GAAACTGTGCTTCAACTAGTCG | (SEQ ID NO:31) |
| 8b | | GGTCTAACACAACTGGTACAG | (SEQ ID NO:32) |
| P1 | (465S) | CAACTGGACTTTACTGAACG | (SEQ ID NO:33) |
| P2 | (1956AS) | TGCTATTAAATACGTAGC | (SEQ ID NO:34) |
| P3 | (666S) | GGATAAGGAATATGAAGTGC | (SEQ ID NO:35) |
| P4 | (1487AS) | GCTGGTGTAATGTCGCTCA | (SEQ ID NO:36) |
| P5 | (748S) | ACACTTCCTCAGATGAGC | (SEQ ID NO:37) |
| P6 | (1015AS) | CACTGTGGAATTCGGGTTTA | (SEQ ID NO:38) |

DESCRIPTION OF THE PREFERRED EMBODIMENTS

Definitions

The patient population treated by the method of this invention excludes patients with "Laron syndrome," otherwise known and defined herein as people with complete lack of GHR function or complete GHIS. These patients attain an adult height of only 110–130 cm. Additional common symptoms include small face and jaw, depressed nasal bridge, frontal bossing, obesity, high-pitched voice, and hypoglycemia in early childhood. Biochemically, they are characterized by having increased serum concentrations of GH but low serum concentrations of IGF-I.

"Increasing the growth rate of a human patient" includes not only the situation where the patient attains at least the same ultimate height as GH-deficient patients treated with GH (i.e., patients diagnosed with GHD), but also refers to a situation where the patient catches up in height at the same growth rate as GH-deficient patients treated with GH, or achieves adult height that is within the target height range, i.e., an ultimate height consistent with their genetic potential as determined by the mid-parental target height.

"Partial growth hormone insensitivity syndrome" or "partial GHIS" refers to a syndrome wherein the patient responds to the same doses of GH as that given to GH-deficient patients, but does not respond as well. This syndrome is further characterized in that the patient has a height of less than about −2 standard deviations below normal for age and sex, preferably in the range of less than about −2 to about −4 standard deviations below normal for age and sex, has a serum level of high-affinity GHBP that is at least 2 standard deviations (typically 2–4 standard deviations) below the normal level for humans, has a serum level of IGF-I that is below the normal mean level for humans, and has a mean or maximum stimulated serum level of GH that is at least normal for humans. Mean serum levels are the mean of measurements in the patient.

As used herein, "non-GH-deficient short stature" refers to a patient who has a height SDS of about ≦2 SD below normal for age and sex and does not have GHD (as classically defined based on secreting levels of GH below a minimum threshold level).

As used herein, "growth hormone" or "GH" refers to growth hormone in native-sequence or in variant form, and from any source, whether natural, synthetic, or recombinant. Examples include human growth hormone (hGH), which is natural or recombinant GH with the human native sequence (somatotropin or somatropin), and recombinant growth hormone (rGH), which refers to any GH or GH variant produced by means of recombinant DNA technology, including somatrem, somatotropin, and somatropin. Preferred herein for human use is recombinant human native-sequence, mature GH with or without a methionine at its N-terminus. More preferred is methionyl human growth hormone (met-hGH) produced in *E. coli,* e.g., by the process described in U.S. Pat. No. 4,755,465 issued Jul. 5, 1988 and Goeddel et al., *Nature,* 282: 544 (1979). Met-hGH, which is sold under the trademark PROTROPIN®, by Genentech, Inc., is identical to the natural polypeptide, with the exception of the presence of an N-terminal methionine residue. This added amino acid is a result of the bacterial protein synthesis process. Also preferred is recombinant hGH available from Genentech, Inc. under the trademark NUTROPIN®. This latter hGH lacks this methionine residue and has an amino acid sequence identical to that of the natural hormone. See Gray et al., *Biotechnology,* 2: 161 (1984). Both methionyl hGH and hGH have equivalent potencies and pharmacokinetic values. Moore et al., *Endocrinology,* 122: 2920–2926 (1988). Another appropriate hGH candidate is an hGH variant that is a placental form of GH with pure somatogenic and no lactogenic activity as described in U.S. Pat. No. 4,670,393 issued Jun. 2, 1987. Also included are GH variants as described in WO 90/04788 published May 3, 1990 and WO 92/09690 published Jun. 11, 1992.

As used herein, "IGF-I" refers to insulin-like growth factor-I from any species, including bovine, ovine, porcine, equine, avian, and preferably human, in native-sequence or in variant form, and from any source, whether natural, synthetic, or recombinant. IGF-I has been isolated from human serum and produced recombinantly. See, e.g., EP 123,228 and 128,733.

Preferred herein for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif., for clinical investigations.

The preferred IGF-I variants are those described in U.S. Pat. No. 5,077,276 issued Dec. 31, 1991, in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1–3)-IGF-I, or des-IGF-I).

"High-affinity growth hormone binding protein" or "high-affinity GHBP" refers to the extracellular domain of the GHR that circulates in blood and functions as a GHBP in several species (Ymer and Herington, *Mol. Cell. Endocrino.,* 41: 153 [1985]; Smith and Talamantes, *Endocrinology,* 123: 1489–1494 [1988]; Emtner and Roos, *Acta Endocrinologica (Copenh.),* 122: 296–302 [1990]), including man. Baumann et al., *J. Clin. Endocrinol. Metab. (J.C.E.M.),* 62: 134–141 (1986); EP 366,710 published May 9, 1990; Herington et al., *J. Clin. Invest.,* 77: 1817–1823 (1986); Leung et al., *Nature,* 330: 537–543 (1987). A second BP with lower affinity for GH has also been described that appears to be structurally unrelated to the GHR. Baumann and Shaw, *J.C.E.M.,* 70: 680–686 (1990). Various methods exist for measuring functional GHBP in serum, with the preferred method being a ligand-mediated immunofunctional assay (LIFA) described by Carlsson et al., *J.C.E.M.,* 73: 1216 (1991) and U.S. Pat. No. 5,210,017.

Modes for Carrying Out the Invention

The subpopulation of patients targeted for treatment by the current invention consists of those patients with partial GHIS as defined above. The patient must exhibit each of the clinical signs set forth to be treatable by the method claimed herein.

The GH and/or IGF-I is directly administered to the patient by any suitable technique, including parenterally, intranasally, intrapulmonary, orally, or by absorption through the skin. If they are administered together, they need not be administered by the same route. They can be administered locally or systemically. Examples of parenteral administration include subcutaneous, intramuscular, intravenous, intraarterial, and intraperitoneal administration. Preferably, they are administered by daily subcutaneous injection.

The GH and/or IGF-I to be used in the therapy will be formulated and dosed in a fashion consistent with good medical practice, taking into account the clinical condition of the individual patient (especially the side effects of treatment with GH or IGF-I alone), the site of delivery of the IGF-I and GH compositions, the method of administration, the scheduling of administration, and other factors known to practitioners. The "effective amounts" of each component for purposes herein are thus determined by such considerations and are amounts that increase the growth rates of the patients.

If GH is administered alone, a dose of greater than about 0.2 mg/kg/week is preferably employed, more preferably greater than about 0.25 mg/kg/week, and even more preferably greater than or equal to about 0.3 mg/kg/week. In one embodiment, the dose of GH ranges from about 0.3 to 1.0 mg/kg/week, and in another embodiment, 0.35 to 1.0 mg/kg/week. Preferably, the GH is administered once per day subcutaneously.

The GH is suitably administered continuously or non-continuously, such as at particular times (e.g., once daily) in the form of an injection of a particular dose, where there will be a rise in plasma GH concentration at the time of the injection, and then a drop in plasma GH concentration until the time of the next injection. Another non-continuous administration method results from the use of PLGA microspheres and many implant devices available that provide a discontinuous release of active ingredient, such as an initial burst, and then a lag before release of the active ingredient. See, e.g., U.S. Pat. No. 4,767,628, col. 2, lines 19–37.

The GH may also be administered so as to have a continual presence in the blood that is maintained for the duration of the administration of the GH. This is most preferably accomplished by means of continuous infusion via, e.g., mini-pump such as an osmotic mini-pump. Alternatively, it is properly accomplished by use of frequent injections of GH (i.e., more than once daily, for example, twice or three times daily).

In yet another embodiment, GH may be administered using long-acting GH formulations that either delay the clearance of GH from the blood or cause a slow release of GH from, e.g., an injection site. The long-acting formulation that prolongs GH plasma clearance may be in the form of GH complexed, or covalently conjugated (by reversible or irreversible binding) to a macromolecule such as one or more of its binding proteins (WO 92/08985 published May 29, 1992) or a water-soluble polymer selected from PEG and polypropylene glycol homopolymers and polyoxyethylene polyols, i.e., those that are soluble in water at room temperature. Alternatively, the GH may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides.

The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1–C4 alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

The GH is covalently bonded via one or more of the amino acid residues of the GH to a terminal reactive group on the polymer, depending mainly on the reaction conditions, the molecular weight of the polymer, etc. The polymer with the reactive group(s) is designated herein as activated polymer. The reactive group selectively reacts with free amino or other reactive groups on the GH. It will be understood, however, that the type and amount of the reactive group chosen, as well as the type of polymer employed, to obtain optimum results, will depend on the particular GH employed to avoid having the reactive group react with too many particularly active groups on the GH. As this may not be possible to avoid completely, it is recommended that generally from about 0.1 to 1000 moles, preferably 2 to 200 moles, of activated polymer per mole of protein, depending on protein concentration, is employed. The final amount of activated polymer per mole of protein is a balance to maintain optimum activity, while at the same time optimizing, if possible, the circulatory half-life of the protein.

While the residues may be any reactive amino acids on the protein, such as one or two cysteines or the N-terminal amino acid group, preferably the reactive amino acid is lysine, which is linked to the reactive group of the activated polymer through its free epsilon-amino group, or glutamic or aspartic acid, which is linked to the polymer through an amide bond.

The covalent modification reaction may take place by any appropriate method generally used for reacting biologically active materials with inert polymers, preferably at about pH 5–9, more preferably 7–9 if the reactive groups on the GH are lysine groups. Generally, the process involves preparing an activated polymer (with at least one terminal hydroxyl group), preparing an active substrate from this polymer, and thereafter reacting the GH with the active substrate to produce the GH suitable for formulation. The above modification reaction can be performed by several methods, which may involve one or more steps. Examples of modifying agents that can be used to produce the activated polymer in a one-step reaction include cyanuric acid chloride (2,4,6-trichloro-S-triazine) and cyanuric acid fluoride.

In one embodiment the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group that is capable of reacting with the GH. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted at elevated temperatures, preferably about 100–110° C. for four hours, with glutaric anhydride.

The monomethyl PEG-glutaric acid thus produced is then reacted with N-hydroxysuccinimide in the presence of a carbodiimide reagent such as dicyclohexyl or isopropyl carbodiimide to produce the activated polymer, methoxypolyethyleneglycolyl-N-succinimidyl glutarate, which can then be reacted with the GH. This method is described in detail in Abuchowski et al., *Cancer Biochem. Biophys.*, 7: 175–186 (1984). In another example, the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described by Bhatnagar et al., *Peptides: Synthesis-Structure-Function, Proceedings of the Seventh American Peptide Symposium*, Rich et al. (eds.) (Pierce Chemical Co., Rockford Ill., 1981), p. 97–100, and in Nitecki et al., *High-Technology Route to Virus Vaccines* (American Society for Microbiology: 1986) entitled "Novel Agent for Coupling Synthetic Peptides to Carriers and Its Applications."

Specific methods of producing GH conjugated to PEG include the methods described in U.S. Pat. No. 4,179,337 on PEG-GH and U.S. Pat. No. 4,935,465, which discloses PEG reversibly but covalently linked to GH. Other specific methods for producing PEG-GH include the following:

PEGylation with methoxypolyethylene glycol aldehyde (Me-PEG aldehyde) by reductive alkylation and purification is accomplished by adding to 2 mg/mL of GH in phosphate-buffered saline (PBS) pH 7.0, 5 mM of Me-PEG aldehyde-5000 (molecular weight 5000 daltons) and 20 mM of NaCNBH3 and gently mixing at room temperature for 3 hours. Ethanolamine is then added to 50 mM to reductively amidate the remaining unreacted Me-PEG. The mixture is separated on an anion-exchange column, FPLC Mono Q. The surplus unreacted Me-PEG does not bind to the column and can then be separated from the mixture. Two main PEGylated GH fractions are obtained with apparent molecular weights of 30K and 40K on reduced SDS-PAGE, vs. 20K of the unreacted GH. GH-GHBP complex is PEGylated in the same manner to give a derivative of 150K by gel filtration.

PEGylation with N-hydroxysuccinimidyl PEG (NHS-PEG) and purification are accomplished by adding NHS-PEG at a 5-fold molar excess of the total lysine concentration of GH to a solution containing 2 mg/mL of GH in 50 mM of sodium borate buffer at pH 8.5 or PBS at pH 7, and mixing at room temperature for one hour. Products are separated on a Superose 12 sizing column and/or Mono Q of FPLC. The PEGylated GH varies in size depending on the pH of the reaction from approximately 300K for the reaction run at pH 8.5 to 40K for pH 7.0 as measured by gel filtration. The H-GHBP complex is also PEGylated the same way with a resulting molecular weight of 400 to 600 Kd from gel filtration.

PEGylation of the cysteine mutants of GH with PEGaleimide is accomplished by preparing a single cysteine mutant of GH by site-directed mutagenesis, secreting it from an $E.\ coli$ 16C9 strain (W3110 ΔtonA phoA ΔE15 Δ(argF-lac)169 deoC2 that does not produce the deoC protein), and purifying it on an anion-exchange column.

Strain 16C9 was constructed genetically by transferring the deoC2 allele from strain CGSC#6092 (No. 6092, available from the $E.\ coli$ Genetic Stock Center, New Haven, Conn. and described in Mark et al., *Molec. Gen. Genet.*, 155: 145–152 (1977), with genotype trxA1 recA1 ilvE720::tn5 metE70 deoC2 lacZ53 rha5 malB45 rpsL151) into a strain designated 7C1.

Strain 7C1 [with genotype W3110 ΔtonA phoA ΔE15 Δ(argF-lac)169] was constructed in several steps using techniques involving transductions with phage P1Kc, derived from P1 (J. Miller, *Experiments in Molecular Genetics* [Cold Spring Harbor, N.Y.: Cold Spring Harbor Laboratory, 1972]), and transposon genetics (Kleckner et al., *J. Mol. Biol.*, 116: 125–159 [1977]). $E.\ coli$ K12 W3110, which is a K12 strain that is F-, λ- (the wild type is F+, λ+) (Bachmann, *Bact. Rev.*, 36: 525–557 [1972]), was used as the starting host.

First, the tonA gene (fhuA) (Kadner et al., *J. Bact.*, 143: 256–264 [1980]; Bachmann, *Microbiol. Rev.*, 47: 180–230 [1983]) was deleted by the insertion and subsequent imprecise excision of a Tn10 transposon into the tonA gene.

In the first step of this procedure, $E.\ coli$ W3110 was transduced with λ::Tn10 to generate a Tn10 hop pool of $E.\ coli$ W3110 (Kleckner et al., *J. Mol. Biol.*, supra).

The $E.\ coli$ W3110::Tn10 hop pool was grown in L broth at 37° C. to a cell density of about $1 \times 10^9$/mL. A total of 0.5 mL of the culture was centrifuged and the pellet was resuspended in 0.2 mL of a λphi80 lysate containing $7.0 \times 10^9$ pfu. The phage was allowed to adsorb for 30 minutes at 37° C. The suspension was then spread on EMB plates supplemented with tetracycline (15 μg/mL). After an overnight incubation at 37° C., the colonies were pooled in 3 mL of L broth, grown overnight at 37° C., washed twice, and resuspended in L broth. A bacteriophage P1kc lysate was made on this culture (Miller, J. H., *Experiments in Molecular Biology*, supra, page 304).

$E.\ coli$ AT982 (no. 4546, $E.\ coli$ Genetic Stock Center, New Haven, Conn.) was transduced to tetracycline resistance by this P1kc lysate. Transductants were selected on L broth plates supplemented with tetracycline (15 μg/mL) and 40 μg/mL diaminopimelic acid (dap). The resulting transductants were screened for tetracycline resistance and the regeneration of the dap gene (dap+, tet$^R$). dap+, tet$^R$ transductants were then tested for λphi80 resistance.

P1kc lysates were then made on several dap+, tet$^R$, λphi80-resistant strains. The lysates were used to transduce $E.\ coli$ W3110 to tetracycline resistance. The transductants were screened and selected for λphi80 resistance.

Tetracycline-sensitive isolates were selected from the W3110 tonA::Tn10-λphi80R transductants. Maloy and Nunn, *J. Bacteriol.*, 145: 1110 (1981). These isolates were checked for λphi80 resistance and tetracycline sensitivity after single colony purification.

DNA was isolated from several tetracycline-sensitive λphi80-resistant mutants and digested with SstII. The SstII-digested DNA was characterized by the Southern blot procedure using radioactively labeled and SstII-digested λ::Tn10 DNA as a probe to determine if the Tn10 had been excised. Davis et al., *Advanced Bacterial Genetics* (Cold Spring Harbor Laboratory, New York, 1980). One of the tetracycline-sensitive isolates was shown to have lost two of the Tn10 hydridization bands as compared to the hybridization between DNA from the λ::Tn10 and the parental W3110 tonA::Tn10λphi80R. A third hybridization band had an altered mobility, indicating that a deletion caused by the imprecise excision of Tn10 had occurred.

SDS-gel electrophoresis of outer membrane preparations from the strain with an imprecise Tn10 excision revealed that the band assumed to be the TonA protein had an altered electrophoretic mobility as compared to the wild-type TonA protein. The resulting protein was non-functional as a λphi80 phage receptor protein. A second independent strain that also had undergone imprecise excision of Tn10 showed no TonA protein on the SDS gel.

Neither of these strains demonstrated reversion to tetracycline resistance or to λphi80 susceptibility, indicating that there was an imprecise excision of all or part of the Tn10 transposon together with either a partial or complete deletion of the tonA gene. Thus, the TonA protein (MW 78,000) was eliminated from the outer membrane, rendering the W3110 tonA strain resistant to several bacteriophages.

Then, two more deletion mutations, phoA Δ E15 (Sarthy et al., *J. Bact.*, 145: 288–292 [1981]) and Δ (argF-lac)-169 (Schweizer et al., *Mol. Gen. Genet.*, 192: 293–294 [1983]), were simultaneously transferred into W3110 tonA by genetic linkage to a kanamycin-resistance transposon inserted into a proline biosynthetic gene (proC::Tn5).

The transposon was eliminated by selecting for a spontaneous prototrophic (pro+) revertant on glucose minimal agar plates. The introduction of the phoA mutation was recognized as transductants that form white colonies on glucose-minimal agar plates with 0.2 mM phosphate and 20 mg/L 5-bromo-4-chloro-3-indolyl phosphate. Likewise, the Δ(argF-lac)169 mutation causes the loss of the enzyme beta-galactosidase and results in cells that form white colonies on MacConkey-1% lactose agar plates. The result was strain 7C1.

Finally, the deoC mutation (Bachmann, supra), removing the aldolase, was introduced into 7C1 by a multistep process of transductions using phage P1kc. Standard methods for transduction were utilized. First, threonine auxotrophy was introduced into 7C1 to provide a means for positive selection of transduced chromosomal segments in the region of the deoC gene as follows.

P1kc was grown on a threonine auxotroph, such auxotrophs being described in Clare N. Berg and Douglas E. Berg, *Microbiology*-1981, "Bacterial Transposons", pp. 107–116 (Amer. Soc. for Microbiology, Washington, D.C., 1981).

The resulting lysate was used to transduce strain 7C1 to tetracycline resistance, selecting for transductants on LB plates containing 25 μg/mL tetracycline. The resulting strain, designated 14A9 (tonAΔ, phoAΔE15, Δ(argF-lac) 169 thr::tn10), reverted spontaneously to prototrophy at a high frequency, so fusaric acid plates (*J. Bact.*, 145: 1110 [1981]) were used to select a stable tetracycline-sensitive threonine auxotroph, designated strain 16C4.

P1kc was grown on Strain CGSC#6092, described supra.

The resulting lysate was used to transduce strain 16C4 to prototrophy, selecting for growth on glucose minimal agar plates. To obtain a high-frequency transducing lysate from strain 2D4, the P1kc phage had to be cycled for growth two times on this host. Five prototrophic transductants of strain 16C4 were isolated, purified, and tested for growth on thymidine minimal agar plates. Four out of five of these isolates could not grow on thymidine and therefore had received the deoC2 mutation that eliminates synthesis of the deoC protein. One of these four isolates was saved and was designated strain 16C9 (ΔtonA, phoA, ΔE15, Δ(argF-lac) 169, deoC2).

PEG-maleimide is made by reacting monomethoxyPEG amine with sulfo-MBs in 0.1M sodium phosphate pH 7.5 for one hour at room temperature and buffer exchanged to phosphate buffer pH 6.2. Next GH with a free extra cysteine is mixed in for one hour and the final mixture is separated on a Mono Q column as in Me-PEG aldehyde PEGylated GH.

As ester bonds are chemically and physiologically labile, it may be preferable to use a PEG reagent in the conjugating reaction that does not contain ester functionality. For example, a carbamate linkage can be made by reacting PEG-monomethyl ether with phosgene to give the PEG-chloroformate. This reagent could then be used in the same manner as the NHS ester to functionalize lysine side-chain amines. In another example, a urea linkage is made by reacting an amino-PEG-monomethyl ether with phosgene. This would produce a PEG-isocyanate that will react with lysine amines.

A preferred manner of making PEG-GH, which does not contain a cleavable ester in the PEG reagent, is described as follows: Methoxypoly(ethylene glycol) is converted to a carboxylic acid by titration with sodium naphthalene to generate the alkoxide, followed by treatment with bromo-ethyl acetate to form the ethyl ester, followed by hydrolysis to the corresponding carboxylic acid by treatment with sodium hydroxide and water, as reported by Bückmann et al., *Macromol. Chem.*, 182: 1379–1384 (1981). The resultant carboxylic acid is then converted to a PEG-N-hydroxysuccinimidyl ester suitable for acylation of GH by reaction of the resultant carboxylic acid with dicyclohexyl-carbodiimide and NHS in ethyl acetate.

The resultant NHS-PEG reagent is then reacted with 12 mg/mL of GH using a 30-fold molar excess over GH in a sodium borate buffer, pH 8.5, at room temperature for one hour and applied to a Q Sepharose column in TRIS buffer and eluted with a salt gradient. Then it is applied to a second column (phenyl Toyopearl) equilibrated in 0.3M sodium citrate buffer, pH 7.8. The PEGylated GH is then eluted with a reverse salt gradient, pooled, and buffer-exchanged using a G25 desalting column into a mannitol, glycine, and sodium phosphate buffer at pH 7.4 to obtain a suitable formulated PEG7-GH.

The PEGylated GH molecules and GH-GHBP complex can be characterized by SDS-PAGE, gel filtration, NMR, tryptic mapping, liquid chromatography-mass spectrophotometry, and in vitro biological assay. The extent of PEGylation is suitably first shown by SDS-PAGE and gel filtration and then analyzed by NMR, which has a specific resonance peak for the methylene hydrogens of PEG. The number of PEG groups on each molecule can be calculated from the NMR spectrum or mass spectrometry. Polyacrylamide gel electrophoresis in 10% SDS is appropriately run in 10 mM Tris-HCl pH 8.0, 100 mM NaCl as elution buffer. To demonstrate which residue is PEGylated, tryptic mapping can be performed. Thus, PEGylated GH is digested with trypsin at the protein/enzyme ratio of 100 to 1 in mg basis at 37° C. for 4 hours in 100 mM sodium acetate, 10 mM Tris-HCl, 1 mM calcium chloride, pH 8.3, and acidified to pH<4 to stop digestion before separating on HPLC Nucleosil C-18 (4.6 mm×150 mm, 5μ, 100 Å). The chromatogram is compared to that of non-PEGylated starting material. Each peak can then be analyzed by mass spectrometry to verify the size of the fragment in the peak. The fragment(s) that carried PEG groups are usually not retained on the HPLC column after injection and disappear from the chromatograph. Such disappearance from the chromatograph is an indication of PEGylation on that particular fragment that should contain at least one lysine residue. PEGylated GH may then be assayed for its ability to bind to the GHBP by conventional methods.

The various PEGylation methods used produced various kinds of PEGylated wild-type GH, with apparent molecular weights of 35K, 51K, 250K, and 300K by size exclusion chromatography, which should be close to their native hydrodynamic volume. These were designated PEG1-GH, PEG2-GH, PEG3-GH, and PEG7-GH, respectively. From the results of the tryptic mapping, the PEG1-GH and PEG2-GH both had the N-terminal 9-amino-acid fragment missing from the chromatogram and possibly PEGylated, which could be confirmed by the mass spectrometry of the big molecular species found in the flowthrough of the liquid chromatograph. From the molecular weight on SDS-PAGE, PEG1-GH may have one PEG on the N-terminal amine, and the PEG2-GH may have two PEG molecules on the N-terminal amine, forming a tertiary amide. The PEG3-GH has about 5 PEG groups per molecule based upon the NMR result, and on the tryptic map, at least five peptide fragments were missing, suggesting that they are PEGylated. The PEG7-GH molecule is believed to have 6–7 PEG groups per molecule based on mass spectrometry.

The sites for adding PEG groups to GH, and those that are preferred residues for such conjugation, are N-terminal methionine or phenylalanine, lysine 38, lysine 41, lysine 70, lysine 140, lysine 145, lysine 158, and lysine 168. Two lysines that appeared not to be PEGylated were lysine 115 and lysine 172.

The GH is also suitably administered by sustained-release systems. Examples of sustained-release compositions useful herein include semi-permeable polymer matrices in the form of shaped articles, e.g., films, or microcapsules. Sustained-release matrices include polylactides (U.S. Pat. No. 3,773, 919, EP 58,481), copolymers of L-glutamic acid and gamma-ethyl-L-glutamate (Sidman et al., *Biopolymers,* 22, 547–556 [1983]), poly(2-hydroxyethyl methacrylate) (Langer et al., *J. Biomed. Mater. Res.,* 15: 167–277 [1981]; Langer, *Chem. Tech.,* 12: 98–105 [1982]), ethylene vinyl acetate (Langer et al., supra) or poly-D-(−)-3-hydroxybutyric acid (EP 133,988), or PLGA microspheres.

Sustained-release GH compositions also include liposomally entrapped GH. Liposomes containing GH are prepared by methods known per se: DE 3,218,121; Epstein et al., *Proc. Natl. Acad. Sci. USA,* 82: 3688–3692 (1985); Hwang et al., *Proc. Natl. Acad. Sci. USA,* 77: 4030–4034 (1980); EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapy. In addition, a biologically active sustained-release formulation can be made from an adduct of the GH covalently bonded to an activated polysaccharide as described in U.S. Pat. No. 4,857,505 issued Aug. 15, 1989. In addition, U.S. Pat. No. 4,837,381 describes a microsphere composition of fat or wax or a mixture thereof and GH for slow release.

In another embodiment, the patients identified above are treated with an effective amount of IGF-I. As a general proposition, the total pharmaceutically effective amount of IGF-I administered parenterally per dose will be in the range of about 50 to 240 $\mu$g/kg/day, preferably 100 to 200 $\mu$g/kg/day, of patient body weight, although, as noted above, this will be subject to a great deal of therapeutic discretion. Also, preferably the IGF-I is administered once or twice per day by subcutaneous injection.

The IGF-I may be administered by any means, including injections (single or multiple, e.g., 1–4 per day) or infusions. As with the GH, the IGF-I may be formulated so as to have a continual presence in the blood during the course of treatment, as described above for GH. Thus, it may be covalently attached to a polymer or made into a sustained-release formulation as described above.

In addition, the IGF-I is appropriately administered together with any one or more of its binding proteins, for example, those currently known, i.e., IGFBP-1, IGFBP-2, IGFBP-3, IGFBP-4, IGFBP-5, or IGFBP-6. The IGF-I may also be coupled to a receptor or antibody or antibody fragment for administration. The preferred binding protein for IGF-I herein is IGFBP-3, which is described in U.S. Pat. No. 5,258,287 and by Martin and Baxter, *J. Biol. Chem.,* 261: 8754–8760 (1986). This glycosylated IGFBP-3 protein is an acid-stable component of about 53 Kd on a non-reducing SDS-PAGE gel of a 125–150 Kd glycoprotein complex found in human plasma that carries most of the endogenous IGFs and is also regulated by GH.

The administration of the IGF binding protein with IGF-I may be accomplished by the method described in U.S. Pat. No. 5,187,151. Briefly, the IGF-I and IGFBP are administered in effective amounts by subcutaneous bolus injection in a molar ratio of from about 0.5:1 to about 3:1, preferably about 1:1.

In a further embodiment, both IGF-I and GH can be administered to the patient, each in effective amounts, or each in amounts that are sub-optimal but when combined are effective. Preferably such amounts are about 50 to 100 $\mu$g/kg/day of IGF-I and about 0.3 mg/kg/week GH. Preferably, the administration of both IGF-I and GH is by injection using, e.g., intravenous or subcutaneous means. More preferably, the administration is by subcutaneous injection for both IGF-I and GH, most preferably daily injections.

It is noted that practitioners devising doses of both IGF-I and GH should take into account the known side effects of treatment with these hormones. For GH, the side effects include sodium retention and expansion of extracellular volume (Ikkos et al., *Acta Endocrinol.* (Copenhagen), 32: 341–361 [1959]; Biglieri et al., *J.C.E.M,* 21: 361–370 [1961]), as well as hyperinsulinemia and hyperglycemia. The major apparent side effect of IGF-I is hypoglycemia. Guler et al., *Proc. Natl. Acad. Sci. USA,* 86: 2868–2872 (1989). Indeed, the combination of IGF-I and GH may lead to a reduction in the unwanted side effects of both agents (e.g., hypoglycemia for IGF-I and hyperinsulinism for GH) and to a restoration of blood levels of GH, the secretion of which is suppressed by IGF-I.

For parenteral administration, in one embodiment, the IGF-I and GH are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IGF-I and GH each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or non-ionic surfactants such as polysorbates, poloxamers, or PEG.

The IGF-I and GH are each typically formulated individually in such vehicles at a concentration of about 0.1 mg/mL to 100 mg/mL, preferably 1–10 mg/mL, at a pH of about 4.5 to 8. Full-length IGF-I is preferably formulated at a pH about 5–6, and des(1–3)-IGF-I is preferably formulated at a pH about 3.2 to 5. GH is preferably at a pH of 7.4–7.8. It will be understood that use of certain of the foregoing excipients, carriers, or stabilizers will result in the formation of IGF-I or GH salts.

While GH can be formulated by any suitable method, the preferred formulations for GH are as follows: For met-GH (PROPTROPIN® brand), the pre-lyophilized bulk solution contains 2.0 mg/mL met-GH, 16.0 mg/mL mannitol, 0.14 mg/mL sodium phosphate, and 1.6 mg/mL sodium phosphate (monobasic monohydrate), pH 7.8. The 5-mg vial of met-GH contains 5 mg met-GH, 40 mg mannitol, and 1.7 mg total sodium phosphate (dry weight) (dibasic anhydrous), pH 7.8. The 10-mg vial contains 10 mg met-GH, 80 mg mannitol, and 3.4 mg total sodium phosphate (dry weight) (dibasic anhydrous), pH 7.8.

For metless-GH (NUTROPIN® brand), the pre-lyophilized bulk solution contains 2.0 mg/mL GH, 18.0 mg/mL mannitol, 0.68 mg/mL glycine, 0.45 mg/mL sodium phosphate, and 1.3 mg/mL sodium phosphate (monobasic monohydrate), pH 7.4. The 5-mg vial contains 5 mg GH, 45 mg mannitol, 1.7 mg glycine, and 1.7 mg total sodium phosphates (dry weight) (dibasic anhydrous), pH 7.4. The 10-mg vial contains 10 mg GH, 90 mg mannitol, 3.4 mg glycine, and 3.4 mg total sodium phosphates (dry weight) (dibasic anhydrous).

Alternatively, a liquid formulation for NUTROPIN® brand hGH can be used, for example: 5.0±0.5 mg/mL rhGH; 8.8±0.9 mg/mL sodium chloride; 2.0±0.2 mg/mL Polysorbate 20; 2.5±0.3 mg/mL phenol; 2.68±0.3 mg/mL sodium citrate dihydrate; and 0.17±0.02 mg/mL citric acid anhydrous (total anhydrous sodium citrate/citric acid is 2.5 mg/mL, or 10 mM); pH 6.0±0.3. This formulation is suitably put in a 10-mg vial, which is a 2.0-mL fill of the above formulation in a 3-cc glass vial. Alternatively, a 10-mg (2.0 mL) cartridge containing the above formulation can be placed in an injection pen for injection of liquid GH to the patient.

While the IGF-I can be formulated in any way suitable for administration, the preferred formulation contains about 2–20 mg/mL of IGF-I, about 2–50 mg/mL of an osmolyte, about 1–15 mg/mL of a stabilizer, and a buffered solution at about pH 5–5.5. Preferably, the osmolyte is an inorganic salt at a concentration of about 2–10 mg/mL or a sugar alcohol at a concentration of about 40–50 mg/mL, the stabilizer is benzyl alcohol or phenol, or both, and the buffered solution is an acetic acid salt buffered solution. More preferably, the osmolyte is sodium chloride and the acetic acid salt is sodium acetate. Even more preferably, the amount of IGF-I is about 8–12 mg/mL, the amount of sodium chloride is about 5–6 mg/mL, the amount of benzyl alcohol is about 8–10 mg/mL, the amount of phenol is about 2–3 mg/mL, and the amount of sodium acetate is about 50 mM so that the pH is about 5.4. Additionally, the formulation can contain about 1–5 mg/mL of a surfactant, preferably polysorbate or poloxamer, in an amount of about 1–3 mg/mL.

In addition, the IGF-I and GH, preferably the full-length IGF-I, may be formulated together in an appropriate carrier vehicle to form a pharmaceutical composition that preferably does not contain cells. In one embodiment, the buffer used for formulation will depend on whether the composition will be employed immediately upon mixing or stored for later use. If employed immediately after mixing, a mixture of full-length IGF-I and GH can be formulated in mannitol, glycine, and phosphate, pH 7.4. If this mixture is to be stored, it is formulated in a buffer at a pH of about 6, such as citrate, with a surfactant that increases the solubility of the GH at this pH, such as 0.1% polysorbate 20 or poloxamer 188. The final preparation may be a stable liquid or lyophilized solid.

The preferred combined composition comprises IGF-I and GH in a weight ratio of IGF-I:GH of between about 1:1 and 100:1 (w/w), about 0.05–0.3 mM of an osmolyte, about 0.1–10 mg/mL of a stabilizer, about 1–5 mg/mL of a surfactant, and about 5–100 mM of a buffer at about pH 5–6. Preferably, the osmolyte is an inorganic salt and the surfactant is nonionic. More preferably, the inorganic salt is sodium chloride or potassium chloride, the stabilizer is phenol or benzyl alcohol, the surfactant is polysorbate or poloxamer, the buffer is sodium acetate or sodium citrate or both, and the amounts of IGF-I and GH are about 2–20 mg/mL and about 0.2–10 mg/mL, respectively, with the weight ratio of IGF-I:GH being between about 1:1 and 50:1. Even more preferably, the amount of IGF-I is about 5–10 mg/mL, the amount of GH is about 1–5 mg/mL, the weight ratio of IGF-I:GH is about 1:1 to 4:1, the amount of sodium chloride is about 5–7 mg/mL, the amount of phenol is about 0.1–3 mg/mL, the amount of benzyl alcohol is about 6–10 mg/mL, the surfactant is polysorbate in an amount of about 1–3 mg/mL, the amount of sodium acetate is about 2.5–4 mg/mL, and the amount of sodium citrate is about 0.1–1 mg/mL.

IGF-I and GH to be used for therapeutic administration are preferably sterile. Sterility is readily accomplished by filtration through sterile filtration membranes (e.g., 0.2 micron membranes). Therapeutic IGF-I and GH compositions generally are placed into a container having a sterile access port, for example, an intravenous solution bag or vial having a stopper pierceable by a hypodermic injection needle.

The IGF-I and GH ordinarily will be stored in unit or multi-dose containers, for example, sealed ampoules or vials, as an aqueous solution, or as a lyophilized formulation for reconstitution. As an example of a lyophilized formulation, 10-mL vials are filled with 5 mL of sterile-filtered 1% (w/v) aqueous IGF-I and GH solutions, and the resulting mixture is lyophilized. The infusion solution is prepared by reconstituting the lyophilized IGF-I and GH using bacteriostatic Water-for-Injection.

The invention will be more fully understood by reference to the following examples. They should not, however, be construed as limiting the scope of the invention. All literature and patent citations are expressly incorporated by reference.

EXAMPLE I

In this example, serum concentrations of GHBP were measured in a large number of samples from short children with either defined etiologies of growth failure (GHD or TS) or ISS, and were compared to GHBP levels in normal controls.

Control subjects

To establish the normal range for GHBP in serum, samples from 773 children, 366 females and 407 males, were analyzed. Ages ranged from 3 to 16 years; in some cases, age for a given subject was reported to the nearest year. The majority of the samples were obtained from a normal, school-aged population through a screening program for detection of antibodies to pancreatic β-cells (Pasco Co. School System, Fla.), and additional samples were generously provided by Dr. Juan Sotos of Children's Hospital of Columbus, Ohio and Dr. Rebecca Kirkland of Baylor College of Medicine, Houston, Tex. The children were healthy and are believed to represent a cross-section of the American population with regard to stature.

Subjects with growth retardation

Serum samples from growth-retarded children (age 1 to 17 years) were collected at baseline evaluation of 776 subjects enrolled in a post-marketing surveillance project, the NCGS. Samples were provided by 106 of the centers participating in this study.

All children with GHD and ISS included for analysis had heights that were 2 or more SDS below the mean for age and sex. Subjects were classified as having GHD by their enrolling physician. None of the children with GHD had maximum stimulated or endogenous GH levels above 10 μg/L reported by the treating physician (using an unspecified assay) or measured at Genentech Inc. using a double monoclonal immunoradiometric assay (Tandem-R HGH, Hybritech, San Diego, Calif.). Excluded are subjects with organic causes of GHD, such as central nervous system (CNS) tumors.

Patients classified as ISS in the NCGS database were either designated as such by the enrolling physician (using various terms) or had a stimulated or endogenous GH level >10 μg/L with no organic etiology of short stature indicated. Patients with TS were so identified by their enrolling physicians and include those with various forms of mosaicism. None of the subjects included had previously received any form of GH therapy.

GHBP measurements

GHBP was measured by LIFA as described above. Briefly, ninety-six-well microtiter plates (Corning Glass Works, Corning, N.Y.) were coated with a monoclonal antibody directed against GHBP (MAb 263, Agen, Australia) by incubating overnight at 4° C. with 100 μL/well of antibody at 10 μg/mL in 50 mmol/L carbonate buffer, pH 9.6. The coated wells were blocked with 150 μL PBS, pH 7.2, containing bovine serum albumin (BSA) (5 g/L) and washed. Standards (recombinant hGHBP) or samples (50 μL/well) were dispensed into the coated wells together with 50 μL/well of recombinant hGH (200 μg/L; Genentech, Inc.) and mouse immunoglobulin G (10 g/L; Fitzgerald Industries, Chelmsford, Mass.).

Plates were sealed, incubated at room temperature for 2 hr with gentle agitation, and washed before addition of a monoclonal anti-GH antibody (MAb MCB, Genentech, Inc.) conjugated to horseradish peroxidase (100 μL/well). After further incubation for 2 hours at room temperature, the plates were washed six times with wash buffer. Freshly prepared substrate solution (0.4 g of o-phenylenediamine dihydrochloride in one liter of PBS plus 0.4 mL of 30% hydrogen peroxide) was added to the plates (100 μL per well) and the incubation carried out in the dark for 15 minutes at room temperature. The reaction was stopped by the addition of 100 μL of 2.25 mol/L sulfuric acid and the absorbance at 490 nm determined. The detection range in the LIFA was 15.6 to 1000 pmol/L. The intra- and interassay coefficients of variation were approximately 7% and 11%, respectively. All samples were measured in duplicate.

GH measurements

To assess spontaneous GH secretion in the different groups, GH concentrations were measured in serum samples taken at 20-minute intervals for 12 hours (8 pm to 8 am) from 851 of the children. Mean values were calculated for each subject. GH concentrations were measured using a monoclonal antibody-based immunoradiometric assay (IRMA), with a detection limit of 0.5 μg/L (Tandem-R HGH, Hybritech).

IGF-I measurements

IGF-I concentrations were measured in serum samples taken from 858 of the children at baseline at the time of overnight GH sampling, using RIA following acid ethanol extraction (IGF-I RIA Kit, Nichols Institute, San Juan Capistrano, Calif.).

Statistical analysis

Standardized height (SDS) was calculated from age- and sex-specific mean and standard deviations derived from the National Center for Health Statistics (NCHS) normative data for American children. Hamill et al., *Am. J. Clin. Nutrition*, 32: 607–629 (1979). Body mass index (BMI) was calculated utilizing the formula: weight (kg)/[height (m)]$^2$. Mean and SD values for age, height SDS, and BMI for growth-retarded children were calculated from data reported on NCGS enrollment forms.

Means and standard deviations for GHBP concentrations (Tables I and III) and for mean 12-hour GH concentrations (Table IV) were calculated after log transformation due to the skewed nature of the data. The antilogs of the mean, mean±2 SD (GHBP, Table I) and mean±1 SD (GHBP, Table III, and mean 12-hr GH, Table IV) were then calculated to provide the listed values. Effects of age and sex on log GHBP concentrations in the control group were assessed by analysis of variance (ANOVA).

The calculation of standardized GHBP levels (SDS) was based on the means and associated SD's from the control subject data grouped by sex and age utilizing the equation below. For a GHBP concentration in an individual 3–15 years of age (the age range for which control samples were available), $$SDS = \frac{\log(GHBP) - \text{mean}(\log(GHBP) \mid \text{age, sex})}{SD(\log(GHBP) \mid \text{age, sex})}$$

where mean (log (GHBP|age, sex) is the average log value of GHBP for control subjects of the same age and sex as that of the individual, and SD (log (GHBP)|age, sex) is the associated SD. After conversion to SDS, the serum GHBP concentrations in children diagnosed with GHD, ISS, and TS were compared with each other and to controls of the same sex by ANOVA. The GHBP SDS was also calculated based on bone age, rather than chronological age.

When multiple between-group comparisons on any variable were performed, Bonferroni adjustments to the p-values for statistical significance were applied to maintain an overall 0.05 level of significance for the test. Nominal p-values for the significant statistical comparisons are included in the text.

Results

The normal range (mean±2 SD) for serum GHBP concentrations in children between 3 and 15 years of age is shown in Table I. Due to a technical problem, results are not available for children 5 years of age. Both age and sex had a significant effect on GHBP concentrations. Females had higher GHBP concentrations than males (p<0.0001). In both sexes, GHBP concentrations increased with age (p<0.0001).

TABLE I

Normal Range for Serum GHBP Concentration (pmol/L)

| Sex  | Age | n  | Mean − 2SD | Mean | Mean + 2SD |
|------|-----|----|------------|------|------------|
| Male | 3   | 20 | 57         | 127  | 282        |
| "    | 4   | 21 | 65         | 120  | 224        |
| "    | 6   | 31 | 60         | 114  | 214        |
| "    | 7   | 31 | 70         | 138  | 272        |
| "    | 8   | 31 | 72         | 193  | 519        |
| "    | 9   | 36 | 60         | 193  | 619        |
| "    | 10  | 39 | 62         | 221  | 783        |
| "    | 11  | 37 | 79         | 244  | 751        |
| "    | 12  | 50 | 69         | 228  | 750        |

TABLE I-continued

Normal Range for Serum GHBP Concentration (pmol/L)

| Sex | Age | n | Mean − 2SD | Mean | Mean + 2SD |
|---|---|---|---|---|---|
| " | 13 | 33 | 80 | 242 | 733 |
| " | 14 | 40 | 65 | 190 | 558 |
| " | 15 | 33 | 52 | 173 | 582 |
| Female | 3 | 15 | 77 | 149 | 288 |
| " | 4 | 17 | 62 | 179 | 519 |
| " | 6 | 32 | 58 | 144 | 358 |
| " | 7 | 32 | 71 | 172 | 419 |
| " | 8 | 32 | 92 | 230 | 572 |
| " | 9 | 34 | 96 | 214 | 477 |
| " | 10 | 35 | 72 | 247 | 844 |
| " | 11 | 32 | 98 | 289 | 849 |
| " | 12 | 36 | 86 | 226 | 595 |
| " | 13 | 35 | 110 | 306 | 856 |
| " | 14 | 34 | 111 | 271 | 660 |
| " | 15 | 32 | 103 | 316 | 965 |

Table II shows the mean (±SD) age, height SDS, and BMI for each group of subjects (height and BMI data were not available for all control subjects). Mean age was similar in all groups (approximately 11 years). Mean height SDS values were not statistically different among the GHD, ISS, and TS females or between the GHD and ISS males. Mean BMI values were significantly lower in the ISS groups compared with the other growth-retarded groups in both females ($p \leq 0.0137$) and males ($p < 0.0001$).

TABLE II

Age, Height SDS, and BMI (mean ± SD)

| Etiology | Sex | n | Age (yr) | Height (SDS) | BMI |
|---|---|---|---|---|---|
| Control | M | 47 | 11.7 ± 2.8 | 0.3 ± 0.8 | 18.4 ± 2.9 |
| " | F | 35 | 11.6 ± 2.4 | 0.3 ± 0.8 | 19.0 ± 3.0 |
| GHD | M | 80 | 11.8 ± 3.6 | −2.9 ± 0.8 | 18.3 ± 4.5 |
| " | F | 27 | 10.8 ± 2.9 | −3.2 ± 0.9 | 17.8 ± 4.0 |
| TS | F | 96 | 11.5 ± 3.3 | −3.3 ± 0.9 | 19.1 ± 4.0 |
| ISS | M | 449 | 11.4 ± 3.4 | −23.9 ± 0.7 | 16.6 ± 2.3 |
| " | F | 124 | 10.8 ± 3.0 | −3.1 ± 0.7 | 16.4 ± 2.4 |

FIGS. 1A–1E show serum GHBP concentrations in individual children with GHD, ISS, and TS compared to the normal range for the same sex (−2 SD to +2 SD). The corresponding mean GHBP concentrations and mean SDS values in all groups are listed in Table III.

For males with either GHD or ISS, the mean GHBP SDS was lower than that of control males (both $p < 0.0001$), and the mean SDS in males with ISS was lower than that of males with GHD ($p < 0.0001$). The mean SDS for females with ISS and GHD was lower than that of control females ($p < 0.0001$ and $p = 0.0046$, respectively). In addition, the mean SDS in ISS females was lower than that in GHD females ($p = 0.0039$). When the GHD groups were limited to subjects with maximum-stimulated GH levels $\leq 5$ μg/L (n=23), the GHBP SDS was not significantly different from the control mean.

Because of differences in BMI between the GHD and ISS groups and the recognized relationship between BMI and GHBP levels, an analysis of covariance (ANCOVA) was performed using BMI as a covariate to determine if the between-group difference in GHBP was independent of differences in BMI. In both males and females, the differences in GHBP between the GHD and ISS groups remained significant ($p < 0.02$).

In 91% of male ISS subjects and 92% of female ISS subjects, GHBP concentrations were below the mean for age- and sex-matched controls. The difference between ISS and GHD subjects was particularly striking in males, where 79 of 394 (20.1%) males with ISS had values >2 SDS below the mean, compared with only 6 of 69 (8.7%) males with GHD.

In contrast to the females with GHD or ISS, the mean GHBP SDS in children with TS did not differ significantly from that of control females. GHBP SDS computed for all growth-retarded groups using bone age rather than chronological age showed little difference (Table III).

TABLE III

Serum GHBP Concentrations (pmol/L)

| Etiology | Sex | n | Mean | Mean −1 SD | Mean +1 SD | Mean GHBP $SDS_{CA}$ (n) | Mean GHBP $SDS_{BA}$ (n) |
|---|---|---|---|---|---|---|---|
| Control | M | 407 | 183 | 103 | 326 | 0.0 (402) | n/a |
| " | F | 366 | 228 | 133 | 394 | 0.0 (366) | n/a |
| GHD (GH < 10) | M | 80 | 146 | 86 | 250 | −0.6 (69) | −0.5 (46) |
| GHD (GH < 10) | F | 27 | 182 | 89 | 372 | −0.6 (26) | −0.5 (18) |
| GHD (GH ≤ 5) | M | 15 | 183 | 111 | 302 | 0.1 (12) | −0.2 (5) |
| GHD (GH ≤ 5) | F | 11 | 203 | 117 | 352 | −0.5 (11) | 0.1 (8) |
| TS | F | 96 | 208 | 115 | 378 | −0.3 (80) | −0.1 (61) |
| ISS | M | 449 | 103 | 63 | 166 | −1.2 (394) | −1.1 (244) |
| " | F | 124 | 131 | 81 | 213 | −1.2 (117) | −1.1 (67) | n/a-not available
CA-chronological age
BA-bone age

For mean GH concentrations obtained during 12-hour overnight GH sampling (Table IV), ANCOVA with etiology, sex, and age revealed that only etiology had a significant impact on the mean 12-hour GH level. As expected, the mean value in children with GHD was significantly less than in controls ($p < 0.0001$). The value in girls with TS was greater than that in GHD females ($p < 0.0001$) and less than that in either ISS or control females (both $p < 0.002$). The mean 12-hour GH concentration in subjects with ISS was not statistically different from that in the controls. However, ISS subjects with GHBP levels>2 SD below the mean had higher mean 12-hour GH values than those with normal GHBP levels (2.8 vs. 2.3 μg/L, $p < 0.005$). Mean IGF-I levels were lowest in GHD patients, and were lower than controls for ISS and TS patients.

TABLE IV

Mean 12-hour GH and IGF-I Concentrations (μg/L)

| | | Mean 12-hr GH (μg/L) | | | | Extracted IGF-I (μg/L) | | |
|---|---|---|---|---|---|---|---|---|
| Etiology | Sex | n | Mean | Mean −1SD | Mean +1SD | n | Mean | Mean −1SD | Mean +1SD |
| Control | M | 47 | 2.1 | 1.2 | 3.5 | 47 | 217 | 130 | 363 |
| " | F | 35 | 2.7 | 1.4 | 5.1 | 35 | 308 | 178 | 531 |

TABLE IV-continued

Mean 12-hour GH and IGF-I Concentrations (µg/L)

| | | Mean 12-hr GH (µg/L) | | | | Extracted IGF-I (µg/L) | | | |
|---|---|---|---|---|---|---|---|---|---|
| Etiology | Sex | n | Mean | Mean −1SD | Mean +1SD | n | Mean | Mean −1SD | Mean +1SD |
| GHD (GH < 10) | M | 79 | 1.4 | 0.9 | 2.1 | 80 | 99 | 41 | 238 |
| GHD (GH < 10) | F | 26 | 1.2 | 0.7 | 2.0 | 27 | 84 | 36 | 195 |
| GHD (GH ≦ 5) | M | 37 | 1.2 | 0.8 | 1.9 | 37 | 73 | 30 | 174 |
| GHD (GH ≦ 5) | F | 15 | 1.0 | 0.6 | 1.6 | 16 | 74 | 31 | 175 |
| TS | F | 96 | 1.8 | 1.0 | 3.2 | 96 | 141 | 80 | 248 |
| ISS | M | 446 | 2.2 | 1.4 | 3.4 | 449 | 108 | 51 | 231 |
| " | F | 122 | 2.2 | 1.3 | 3.5 | 124 | 120 | 56 | 257 |

Serum GHBP concentrations in some children with ISS are lower than those in age-matched control children. Compared with control subjects, children with GHD also had lower GHBP concentrations, but the reduction was less pronounced than in children with ISS. In girls with TS, a condition where the diagnosis is based on the presence of a chromosomal abnormality and therefore is absolute, the GHBP levels were not different from those of the control group, indicating that the GHBP levels do not simply correlate with short stature.

In addition to geographically and genetically well-defined populations with impaired peripheral GH action, such as patients with Laron syndrome and African pygmies, there may be subjects with more subtle forms of GH insensitivity, most likely representing a variety of molecular defects. In spite of the probable heterogeneity of the causes of growth retardation in children with IS, the results above show that as a group they have reduced serum GHBP concentrations, and a significant subset (20%) have GHBP levels 2 SD or more below the normal mean for age and sex.

The children with ISS that were studied did not differ from the control group in terms of GH secretion and had significantly lower GHBP concentrations than those of the group with GHD. Patients defined as GHD, based on the arbitrary cutoff of maximum GH<10 µg/L, had lower GHBP levels than controls. However, in GHD patients with maximum GH≦5 µg/L, mean GHBP SDS was greater than that of the GHD group with GH>5 µg/L and was not different from that of the controls.

EXAMPLE II

Patients followed in a post-marketing surveillance study, the National Cooperative Growth Study (NCGS), were studied to compare growth rates for GHD patients with those for ISS patients treated with various doses of GH. The ISS patients include both those with normal GHBP levels and those with low GHBP levels. The results for the ISS patients, shown in FIG. 2, demonstrate that a substantially higher growth rate was obtained for children treated with 0.25±0.025 mg/kg/week of GH as compared to 0.20 mg/kg/week or less. Comparison with the GHD patients reveals that the normal doses of GH of up to 0.20 mg/kg/week were not sufficient to allow patients to have a mean growth rate range close to that seen in the GHD patients; however, doses of 0.25±0.025 mg/kg/week resulted in a mean growth rate closer to the range seen in GHD patients (about 10 cm/year). Hence, a dose of GH of greater than about 0.20 mg/kg/week is suitable for at least some patients identified by this invention.

EXAMPLE III

Patients with ISS (as defined by a maximum GH level>10 µg/L and height SDS<−2) have low GHBP levels compared to normal controls as determined by LIFA. This was not the case in short children with GHD or TS.

To assess the utility of the GHBP assay in the evaluation of short children, ISS patients were grouped according to their GHBP SDS. Patients with low GHBP SDS, defined as <−2, were compared with patients with normal GHBP levels (GHBP SDS>−2) to determine whether there was evidence of impaired sensitivity to GH treatment in the former group.

Patient Population

Serum samples were collected at 96 sites from 511 children with ISS who were subsequently treated with Protropin® brand hGH (with the mean±SD dose of GH being 0.26±0.07 mg/kg/week by injection parenterally for patients with one-year growth data, with the particular dose and schedule of GH being at the discretion of the individual clinical investigator), and enrolled in the NCGS. To be included in this study, patients had to have a maximum stimulated GH>10 µg/L, height SDS≦−2, and no other reported etiology of short stature. The results of the GHBP measurements were not known before the initiation of GH therapy. For analyses involving growth response while on GH treatment, only prepubertal patients were included.

Assay Methods

GHBP was assayed using the LIFA, as described in Carlsson et al., supra. Monoclonal antibodies to GHBP (MAb 263) and GH (MAb MCB) were used. GHBP values were standardized for age and sex using normative data for the LIFA based on samples provided by Dr. Thomas Merimee at University of Florida, Division of Endocrinology and Metabolism, Health Science Center, P.O. Box 100226, Gainesville, Fla. 32610-0226, and by Drs. Sotos and Kirkland mentioned above. These values have been previously reported. Carlsson et al., *J.C.E.M.*, 78: 1325–1330 (1994).

Overnight samples for GH were assayed using a double monoclonal immunoradiometric assay (Tandem-R HGH, Hybritech, San Diego, Calif.). Values reported for GH stimulation tests were measured using various GH assays.

IGF-I was measured by radioimmunoassay following acid-ethanol extraction (IGF-I by Extraction, Nichols Institute, San Juan Capistrano, Calif.) and standardized for age and sex using the normative data provided.

Statistical Methods

Heights were standardized for age and sex, and weights were standardized for height and sex using norms derived from published data for North American children. Hamill et al., *Am. J. Clin. Nutrition*, 32: 607–629 (1979). Mothers' and fathers' height SDS were calculated based on height percentiles for normal adults. Hamill et al., supra.

Multiple linear regression was used to determine which explanatory variables were linearly related to GHBP SDS, if any. In addition, subjects were divided into two groups based on their GHBP SDS (≦−2 SD and >−2 SD), to determine the significance, if any, of GHBP values that are below the normal range. The two groups were compared to each other with respect to the means or medians of several covariates (see Table VI). Univariate tests of significance between groups were performed using one of three tests: the t-test (for Gaussian-distributed variables), the Wilcoxon rank sum test (for non-Gaussian-distributed variables), or the Chi-square test (for categorical variables). To adjust for multiple comparisons, p-values <0.005 were considered statistically significant. ANCOVA was used to test for differences between the two GHBP groups after controlling for other significant variables.

Results

Patients in the low GHBP group were younger and had lower weight-for-height SDS and BMI than the normal GHBP group (Table V). The mean height SDS was −2.9 in both groups, with values ranging from −5.8 to −2.0. Approximately three-fourths of the patients were male; a similar sex distribution is seen in the total NCGS database. August et al., *J. Pediatr.*, 116: 899–903 (1990). Seventy-two percent of the patients were pre-pubertal at baseline.

TABLE V

Baseline Patient Charcateristics

| | GHBP SDS ≤ −2 | | | GHBP SDS > −2 | | | |
|---|---|---|---|---|---|---|---|
| | n | mean | SD | n | mean | SD | p-value |
| Male | 80 (79%) | | | 315 (77%) | | | 0.61 |
| Female | 21 (21%) | | | 95 (23%) | | | |
| Prepubertal | 75 (78%) | | | 281 (71%) | | | 0.14 |
| Pubertal | 21 (22%) | | | 117 (29%) | | | |
| Age (yr) | 101 | 10.4 | 3.1 | 410 | 11.4 | 2.8 | 0.003 |
| Bone age (yr) | 64 | 7.8 | 3.2 | 245 | 8.9 | 3.2 | 0.015 |
| Bone age delay (yr) | 64 | 2.4 | 1.9 | 245 | 2.4 | 1.7 | 0.54 |
| Bone age SDS | 64 | −2.8 | 2.1 | 245 | −2.7 | 1.8 | 0.73 |
| Height SDS | 101 | −2.9 | 0.7 | 410 | −2.9 | 0.6 | 0.65 |
| Weight-for-Height SDS | 93 | −0.2 | 0.9 | 357 | 0.1 | 1.1 | 0.019 |
| Body mass index (kg/m$^2$) | 100 | 15.7 | 1.6 | 410 | 16.6 | 2.2 | 0.0006 |
| Mother's height SDS | 93 | −0.9 | 1.3 | 365 | −1.1 | 1.1 | 0.27 |
| Father's height SDS | 92 | −0.7 | 1.4 | 361 | −0.6 | 1.2 | 0.57 |

There were 101 patients with GHBP SDS≤−2 (mean −2.5) and 410 patients with GHBP SDS>−2 (mean −0.9) (Table VI). The two groups had comparable median maximum GH levels; however, these values are difficult to evaluate because of the use of various GH assays. The average for the mean 12-hour GH concentrations (using the Hybritech assay) was significantly higher in the low GHBP group, whereas the IGF-I SDS was significantly lower in that group (both p=0.0001, Table VI).

Figure 3A:
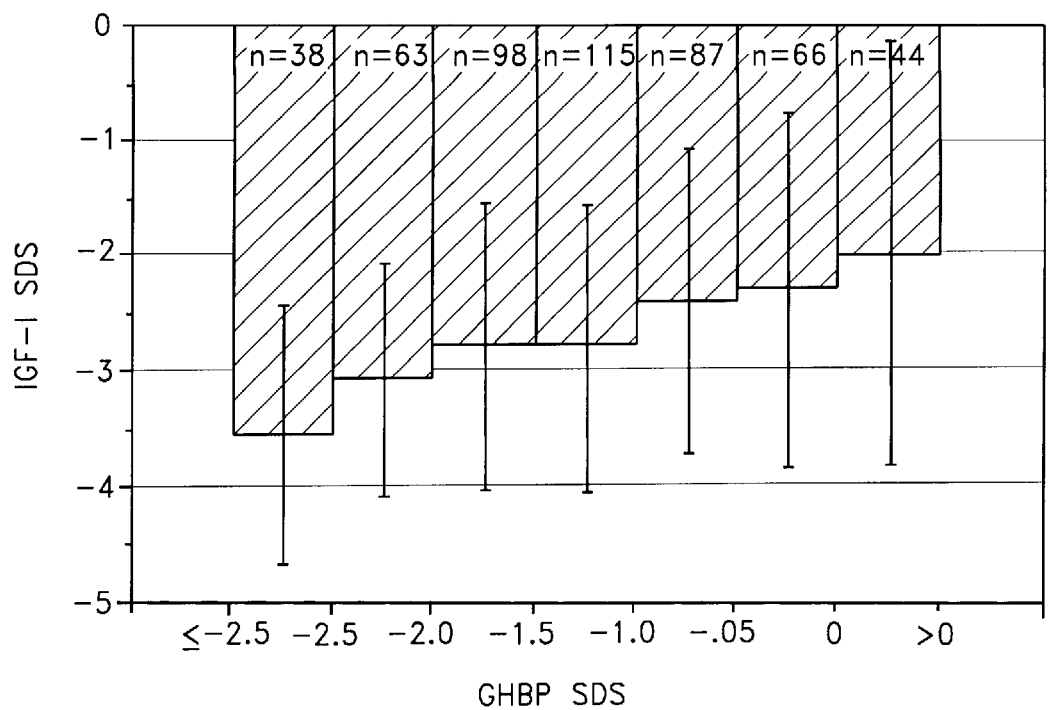
FIG. 3A depicts IGF-I concentrations, standardized for age and sex and expressed as SDS, by GHBP SDS (mean±SD).
Figure 3B:
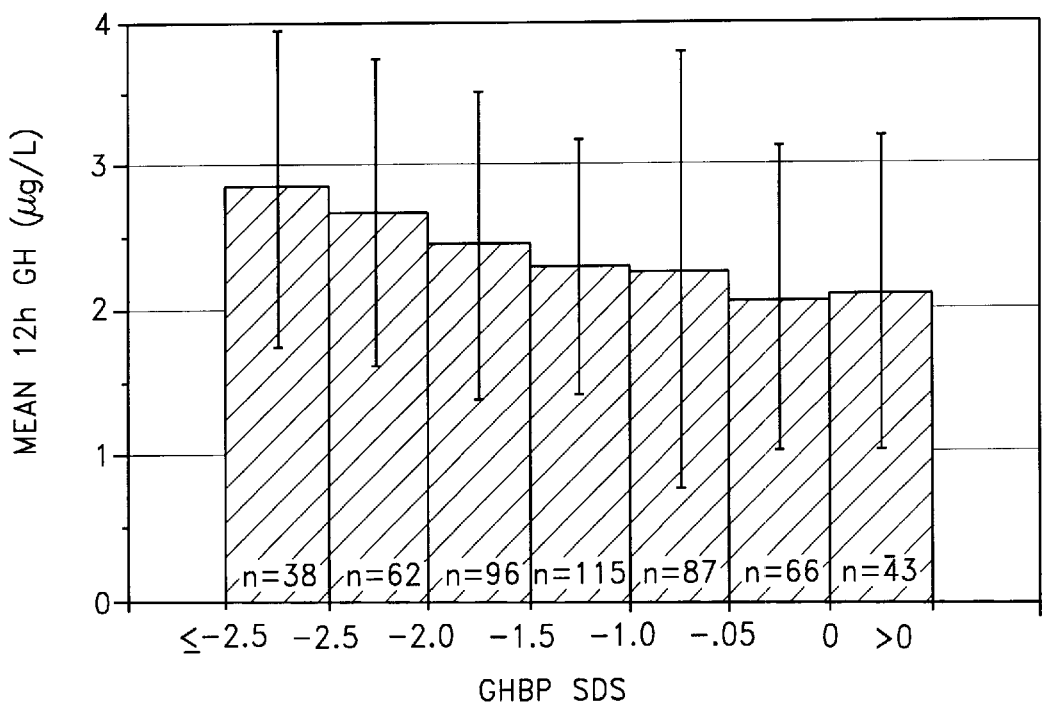
FIG. 3B depicts mean 12-hour GH concentrations from overnight sampling every 20 min for 12 hr, by GHBP SDS (mean±SD) for patients enrolled in the study used to generate FIG. 2.

FIG. 3 shows that those with low GHBP SDS had lower IGF-I SDS (FIG. 3A) and higher mean 12-hour GH levels (FIG. 3B). Among all ISS patients, GHBP SDS was positively correlated with IGF-I SDS (r=0.285, p=0.0001) and negatively correlated with mean 12-hour GH (r=−0.17, p=0.0001).

ANCOVA, controlling for differences in age, weight-for-height SDS, and mean 12-hour GH, showed that patients with GHBP SDS≤−2 still had significantly lower IGF-I SDS than those with GHBP SDS>−2 (p=0.0001). Similarly, the low-GHBP group had significantly higher mean 12-hour GH than the normal-GHBP group (p=0.0001) after controlling for age, weight-for-height SDS, and IGF-I SDS.

TABLE VI

Baseline GHBP, IGF-I and GH Concentrations (mean ± SD)

| | GHBP SDS ≤ −2 (n = 101) | GHBP SDS > −2 (n = 410) | p-value |
|---|---|---|---|
| GHBP (pmol/L) | 60 ± 14 | 138 ± 68 | 0.0001 |
| GHBP SDS | −2.5 ± 0.4 | −0.9 ± 0.8 | 0.0001 |
| IGF-I (μg/L) | 100 ± 61 | 149 ± 101 | 0.0001 |
| IGF-I SDS | −3.3 ± 1.1 | −2.5 ± 1.4 | 0.0001 |
| Mean 12-hr GH (μg/L) | 2.8 ± 1.1 | 2.3 ± 1.1 | 0.0001 |
| Maximum GH (μg/L) | 15.7 ± 8.2 | 15.5 ± 10.0 | 0.309 |

Figure 4:
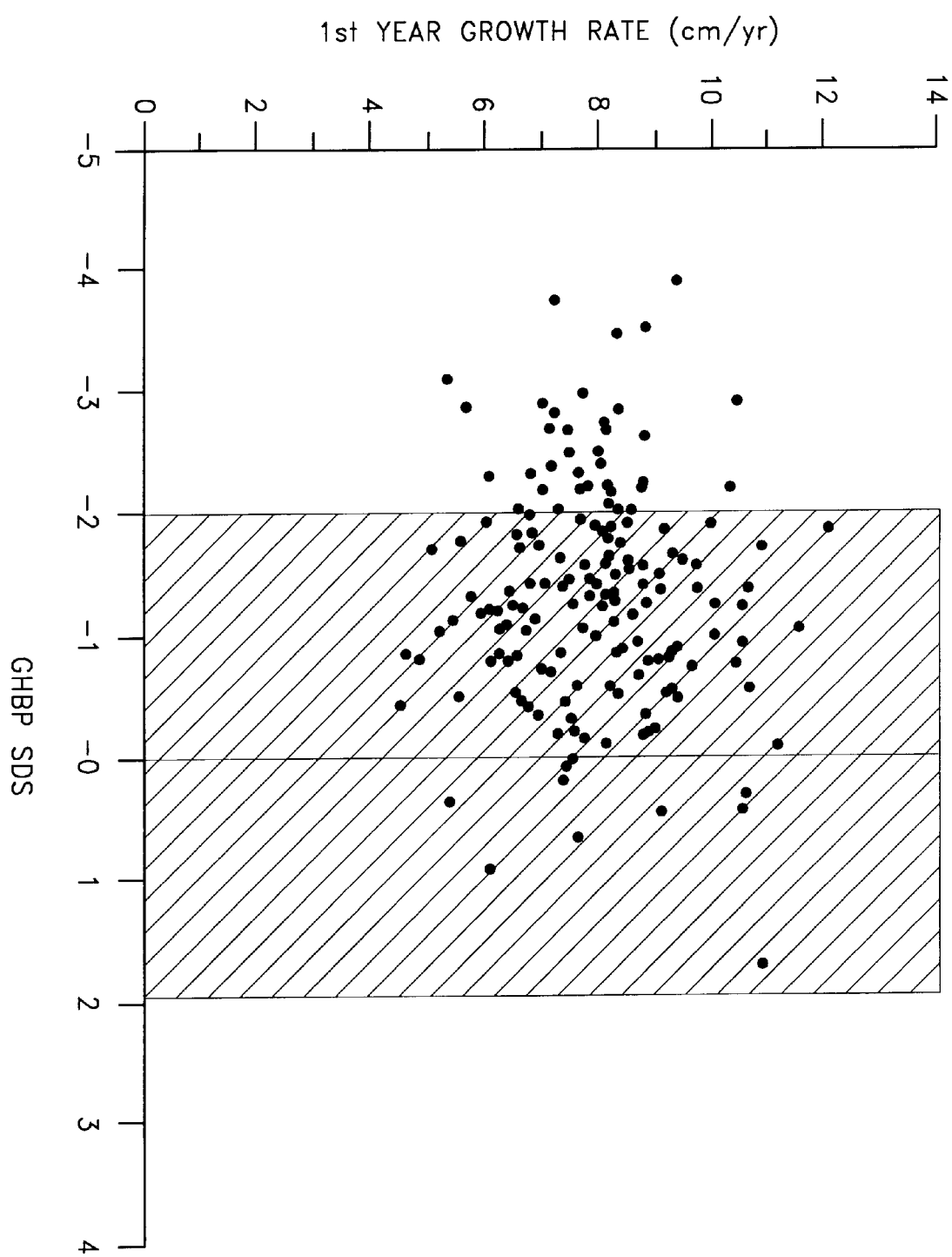
FIG. 4 shows the first-year annualized growth rate (cm/yr) by GHBP SDS for patients treated with human GH (hGH) who remained prepubertal during the first year of GH therapy (n=166). The shaded area represents the normal range for GHBP (−2 SDS to +2 SDS).

Growth rate analyses were restricted to patients who remained prepubertal during the treatment periods considered. There were no significant linear correlations of GHBP SDS and either growth rate or change in height SDS during each of the first three years of treatment. The mean pretreatment growth rate was approximately 4 cm/yr regardless of GHBP SDS. The mean growth rate during the first year of GH therapy was approximately 8 cm/yr. FIG. 4 shows first-year growth rates for pre-pubertal patients treated with GH plotted against their GHBP SDS. There was no statistically significant correlation between the two (r=0.047, p=0.55, n=166). The figure shows that the patients who can be treated by the invention herein are those below the shaded area, provided that they also have the GH, IGF-I, and height requirements set forth as required in this subpopulation. The results indicate that the patients with low GHBP SDS levels and having the criteria of this invention responded to pharmacologic administration of GH.

Figure 5:
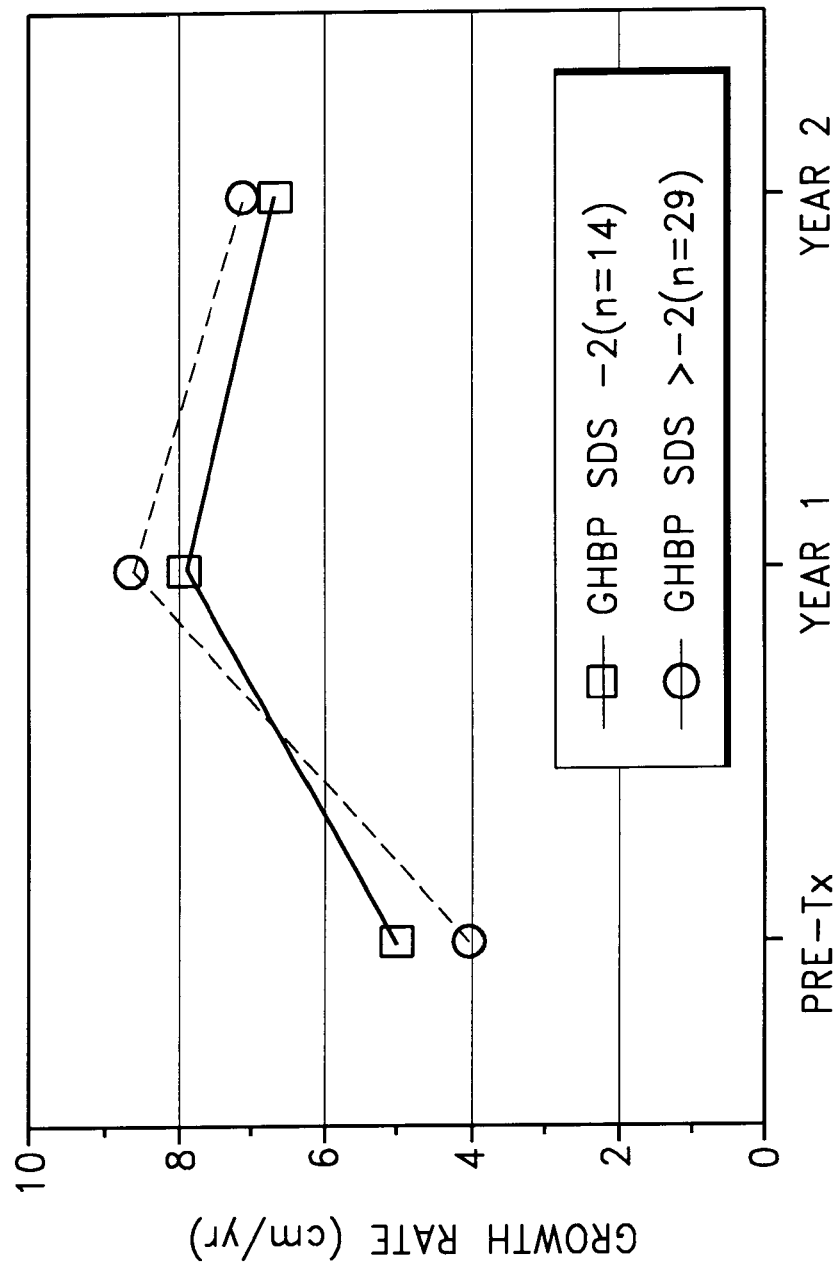
FIG. 5 is a graph of pre-treatment, first-year treatment, and second-year treatment growth rates for patients whose data is set forth in Table VII of Example III below having a GHBP SDS −2 (n=14) (squares) or a GHBP SDS >−2 (n=29) (circles).
Figure 6A:
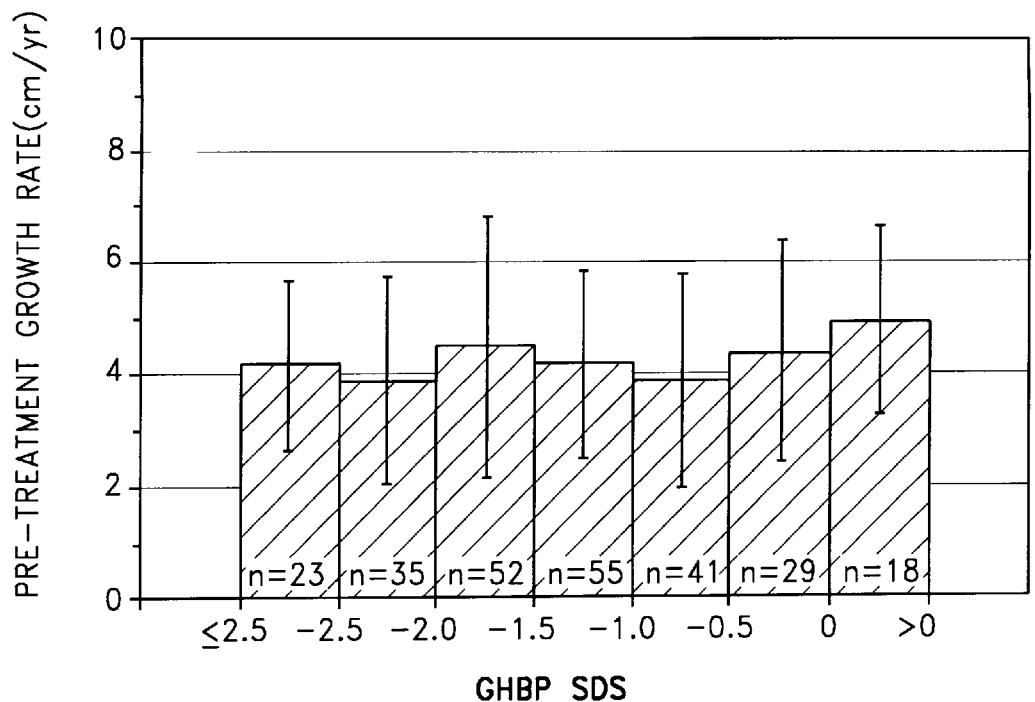
FIGS. 6A and 6B show, in bar-graph form, pre-treatment (FIG. 6A) and first-year treatment (FIG. 6B) growth rates by GHBP SDS for the patients used to generate FIG. 5.
Figure 6B:
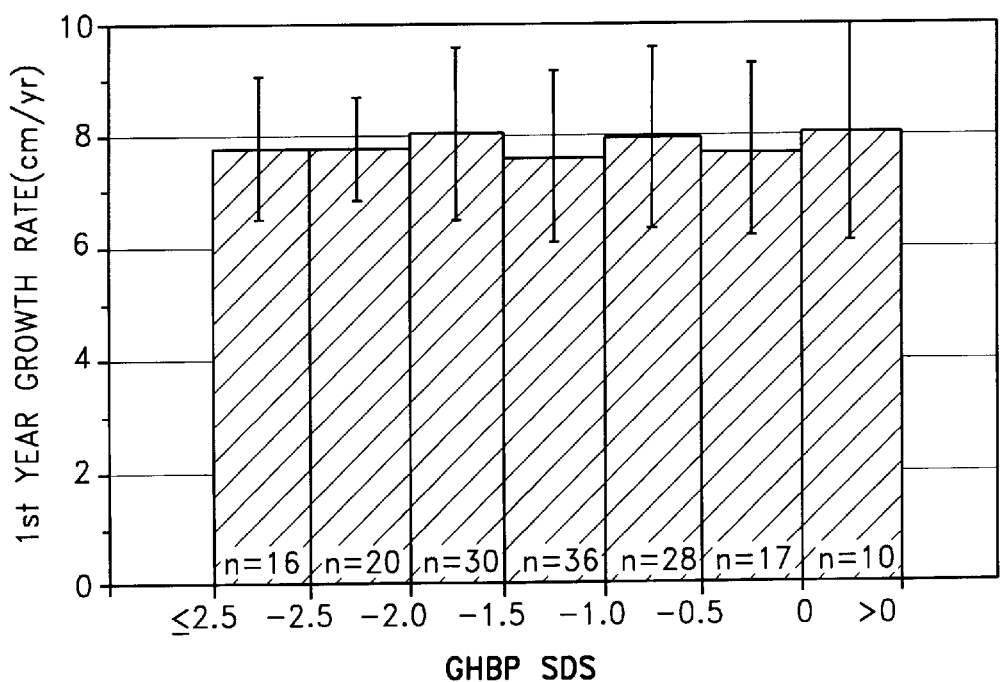

FIGS. 5 and 6 compare the pre-treatment and first-year growth rates of the patients (and in FIG. 5 also second-year growth rates). These figures show that there is a clear increase in growth in the GH-treated patients, regardless of whether the GHBP SDS of the particular patient is −2 or >−2.

Table VII shows the growth response data for the group having low GHBP SDS compared with the group having normal GHBP SDS. The two groups had similar mean GH dose and injection schedules during the first year of therapy. There were no significant differences between the groups for pretreatment growth rate or growth rates during the first four years of GH therapy. The mean change in height SDS was also not statistically different between the two groups; the mean increase in those followed for 4 years was 1.5±0.6 (n=13) in the low GHBP group and 1.7±0.6 (n=21) in the normal GHBP group.

TABLE VII

Growth Rate and Change in Height SDS from Baseline on GH Therapy in Prepubertal Patients

| | GHBP SDS ≤ −2 | | | GHBP > −2 | | | |
|---|---|---|---|---|---|---|---|
| | n | mean | SD | n | mean | SD | p-value |
| 1st year GH Dose (mg/kg/wk) | 42 | 0.26 | 0.07 | 141 | 0.25 | 0.08 | 0.72 |
| 1st year GH Schedule (inj./wk) | 42 | 3.7 | 1.1 | 143 | 3.5 | 1.1 | 0.06 |
| Growth Rate (cm/yr) | | | | | | | |
| Pretreatment | 58 | 4.0 | 1.7 | 197 | 4.2 | 1.9 | 0.47 |
| 1st Year | 36 | 7.8 | 1.1 | 130 | 8.0 | 1.5 | 0.55 |

TABLE VII-continued

Growth Rate and Change in Height SDS from Baseline on GH Therapy in Prepubertal Patients

| | GHBP SDS ≤ -2 | | | GHBP > -2 | | | |
|---|---|---|---|---|---|---|---|
| | n | mean | SD | n | mean | SD | p-value |
| 2nd Year | 22 | 7.2 | 1.2 | 45 | 7.0 | 1.1 | 0.80 |
| 3rd Year | 16 | 6.8 | 1.2 | 22 | 7.1 | 1.0 | 0.29 |
| 4th Year | 12 | 5.8 | 1.1 | 16 | 6.3 | 1.0 | 0.30 |
| Cumulative Δ Height SDS | | | | | | | |
| Year 1 | 45 | 0.5 | 0.2 | 145 | 0.5 | 0.3 | 0.91 |
| Years 1,2 | 28 | 1.0 | 0.4 | 67 | 0.9 | 0.4 | 0.65 |
| Years 1,2,3 | 19 | 1.30 | 0.5 | 36 | 1.3 | 0.4 | 0.70 |
| Years 1,2,3,4 | 13 | 1.5 | 0.6 | 21 | 1.7 | 0.6 | 0.24 |

Although short stature may be defined in a variety of ways, such as being below a given percentile for standard height norms, the patients in this study represent a more select group. These patients were all prescribed GH therapy, and thus went through a screening and selection process by the enrolling physicians. In addition, patients with height SDS above -2 were not included in this study. The resulting group had a mean height SDS of -2.9, mean bone age delay of 2.4 years, and mean growth rate of 4.2 cm/yr, similar to other reported patients with ISS treated with GH. Hopwood et al., *J. Pediatr.*, 123: 215-222 (1993); Albertsson-Wikland, *Acta Paediatr. Scand. Suppl.*, 343: 77-84 (1988). In this select group, it was found that some had low serum GHBP levels, after standardization for age and sex, and after adjusting for bone age. Carlsson et al., *J.C.E.M.*, 78, supra.

GHBP has been shown to be derived from the same gene as the GHR and share sequence homology with its extracellular domain. Leung et al., *Nature*, 330: 537-543 (1987). Serum GHBP levels measured using the functional assay were low or undetectable in patients with complete GHIS. Fielder et al., *J.C.E.M.*, 74: 743-750 (1992). In this example the normal range of GHBP levels in children has been determined by age and sex and it has been shown that the low GHBP levels seen in patients with ISS were significantly less than those seen in normal or GH-deficient subjects or in Turner syndrome. Carlsson et al., *J.C.E.M.*, 78, supra.

Overnight 12-hour serial sampling profiles for GH were obtained on all of the children in this study and the mean levels were normal, suggesting, without being limited to any one theory, that neurosecretory dysfunction was not present in most of the patients. The mean 12-hour GH levels showed a negative correlation with mean GHBP SDS, as has been described in normal individuals. Martha et al., *J.C.E.M.*, 73: 175-181 (1991). However, IGF-I SDS was positively correlated with GHBP SDS. Thus, the patients with lower GHBP levels had higher GH yet lower IGF-I levels, consistent with GH insensitivity.

A significant predictor of GHBP concentration is body composition, which was assessed using both BMI and weight standards for height and age. In an ANCOVA, it was found that GHBP remained a significant predictor of mean 12-hour GH and IGF-I SDS after controlling for age and weight-for-height SDS.

The growth data available for prepubertal patients enrolled in the NCGS database revealed no significant linear correlation between baseline GHBP SDS and either pretreatment growth rate or baseline height SDS. Without being limited to any one theory, one possible explanation is that growth rate and height are commonly used to select patients to be treated with GH, and thus are uniformly low in this patient population.

Figure 7:
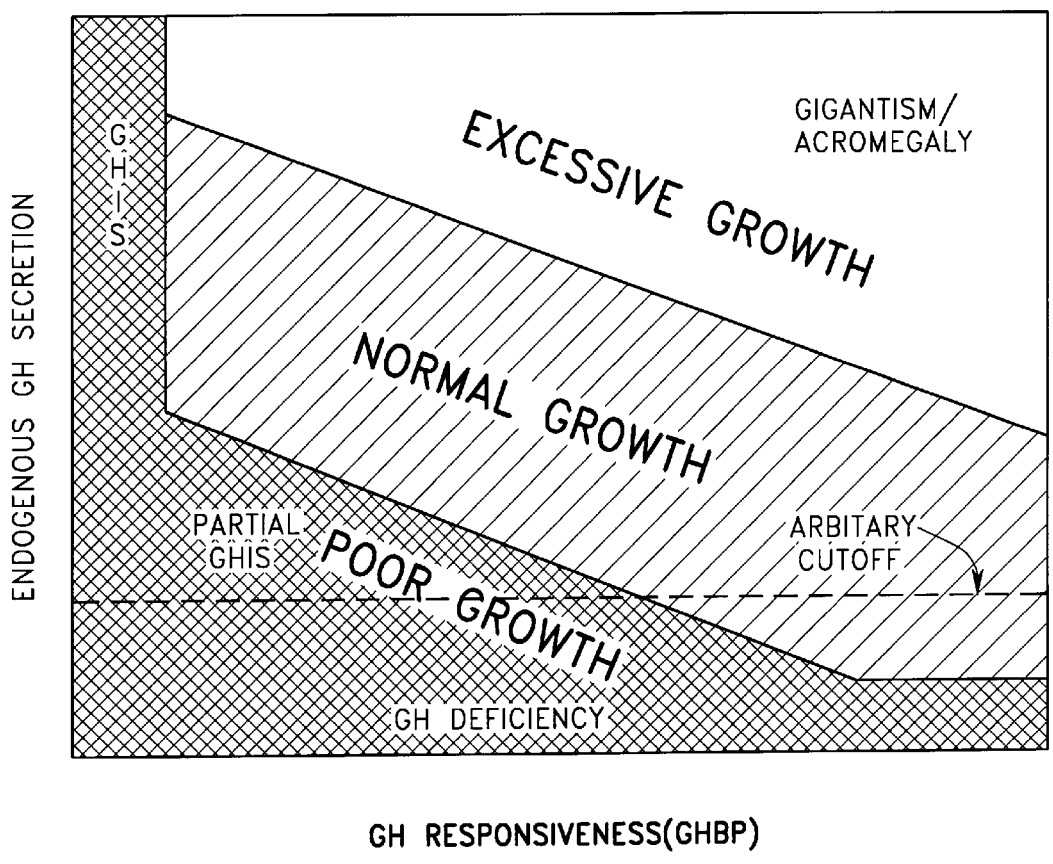
FIG. 7 shows growth status as predicted by a measure of GH secretion (e.g., stimulated or endogenous GH concentration) vs. a measure of GH responsiveness (e.g., GHBP concentration).

An interesting observation was the lack of correlation of GHBP SDS and growth response to GH therapy. Because GH secretion and GHBP levels appear to be negatively correlated in normally growing children (Martha et al., supra), a normal range can be proposed as depicted in FIG. 7. Those with excessive GH relative to their GHBP levels would be expected to have excessive growth, and those whose GH levels are too low for their GHBP levels would have poor growth. Currently, GHD is arbitrarily defined and based solely on measures of GH secretion; it is possible that some patients with GH levels above this arbitrary threshold (and within the scope of this invention) have inadequate amounts of GH relative to their low GHBP levels, resulting in poor growth. Administering exogenous GH to this subset of patients (with lower GHBP and IGF-I levels and higher mean 12-hour GH levels compared to normal, suggesting partial GH insensitivity) would be expected to raise their circulating GH to levels more appropriate for their low GHBP levels, thus overcoming their partially resistant state.

EXAMPLE IV

Introduction

The etiology of the growth failure in the majority of short children without GHD (non-GH-deficient short stature children) is poorly defined. These otherwise normal children with ISS produce normal amounts of GH in response to pharmacological stimulation, but fail to demonstrate a normal growth pattern. Lippe and Nakamoto, *Rec. Prog. Horm. Res.*, 48: 179-235 (1993). A number of GH-related defects have been proposed to account for their growth failure, including neurosecretory dysfunction (Spiliotis et al., *J. Am. Med. Assoc.*, 251: 2223-2230 [1984]; Zadik et al., *Pediatrics*, 76: 355-360 [1985]), and immunologically reactive but biologically inactive GH. Kowarski et al., *J.C.E.M.*, 47: 461-464 (1978); Valenta et al., *N. Eng. J. Med.*, 31: 214-217 (1985). While these mechanisms may account for the failure to grow normally in some ISS patients, the majority do not appear to have demonstrable defects in GH secretion or function. Lanes, *Am. J. Dis. Child.*, 143: 1284-1286 (1989); Ilondo et al., *J.C.E.M.*, 70: 1445-1451 (1990).

An alternative possibility is that ISS patients have normal secretory patterns of bioactive GH and that the defect lies in the ability of target cells to respond to GH. Such defects could lie at the level of the GHR or the mediators of GH signaling, such as IGF-I or the IGF-I receptor. Alterations in the IGF-I gene are uncommon in growth disorders. Lajara et al., *J.C.E.M.*, 70: 687-692 (1990). Resistance to GH could be due to reduction in the affinity of the GHR for GH, impaired ability to propagate a signal in response to binding GH, or to defects causing reduced cell surface receptor number. The high-affinity GHBP present in human serum is identical to the extracellular domain of the GHR and is thought to be produced from the receptor by proteolytic cleavage. Sotiropoulos et al., *Endocrinol.*, 132: 1863-1865 (1993). Immunofunctional GHBP levels (Carlsson et al., *J.C.E.M.*, 73, supra) are below the mean in 90% of ISS patients, and are more than two SDs below the mean in 20% of these children (Carlsson et al., *J.C.E.M.*, 78, supra; Mauras et al., *Metabolism*, 43: 357-359 [1994]). Without being limited to any one theory, it is noted that abnormalities in the GHR that reduce the amount of functional GHBP may be present in ISS patients.

A phenotype of partial GHIS in ISS is postulated by the observation in Example III that ISS patients with lower GHBP levels have lower IGF-I levels and higher mean 12-hour GH levels when compared to those with normal GHBP levels. Without being limited to any one theory, this suggests a deficiency in signaling via the GHR, leading to reduced IGF-I production and reduced negative feedback of IGF-I on GH secretion. Most ISS children respond to recombinant GH treatment with an increase in growth rate (Hopwood et al., supra); however, this response is less than that seen herein in patients with GHD (GH-deficient patients) treated with the same GH dose, once again suggesting, as one theory, a partial insensitivity to GH in ISS patients.

The high frequency of inactivating mutations in the GHR gene in complete GHIS or Laron syndrome (LS) indicates that most complete GHIS cases can be explained by lack of functional GHR. Most LS patients lack detectable GHBP activity in their blood (Baumann et al., *J.C.E.M.*, 65: 814–816 [1987]; Daughaday et al., *Proc. Natl. Acad. Sci. USA*, 84: 4636–4640 [1987]), and when measured, have no or very low levels of specific GH binding to hepatic microsomes. Eshet et al., *Isr. J. Med. Sci.*, 20: 8–11 (1984). There are characterized GHR mutations associated with LS concentrated in the extracellular domain of the protein (reviewed by Rosenfeld et al., *Endocrinol. Rev.*, 15: 369–390 [1994]).

To determine if the milder phenotype of partial GHIS could be caused by less disruptive mutations in GHR, and that the reduced levels of circulating GHBP in the ISS population may serve as a marker for partial GHIS and may indicate mutations in the GHR, a subset of ISS patients with GHBP levels greater than 2 SD below the mean were selected, and the coding region of the GHR gene was analyzed for mutations. Using single-strand conformation analysis (SSCA) and sequencing of polymerase chain reaction (PCR) products with altered mobility, mutations were detected in the extracellular domain of the receptor in 4 out of 14 patients.

Subjects

Fourteen ISS patients were selected from two substudies of the NCGS with some or all of the following criteria: 1) height SDS<–2.5; 2) serum IGF-I levels below normal mean levels (measured by acid-ethanol extraction, Nichols Institute); 3) serum GH>10 μg/L on one or more provocative tests; 4) maximum serum GHBP SDS≦–2 (measured by LIFA as described in Carlsson et al., *J.C.E.M.*, 73, supra, or by charcoal separation as described in Amit et al., *J.C.E.M.*, 71: 474–479 [1990]) in the case of Patient 1); 5) pre-treatment growth rate<4 cm/year; and 6) absence of underlying systemic illness. Additional information was considered if available, including mean 12-hour GH (Hybritech assay), 1st-year growth rate on GH, and IGFBP-3 levels (Endocrine Sciences). The scoring system used to select the patients from the NCGS database is shown in Table VIII. Out of a maximum score of 12, the patients scored 4–10 and all had GHBP SDS≦–2. Relatives of two patients (#2 and #4) were studied to confirm the heritability of the mutations. Twenty-four normal adult volunteers whose height SDS fell within or above the normal range (–2.0 to +3.5 SDS) served as controls. The statistical significance of population differences was calculated with a Fischer Exact Test.

TABLE VIII

Criteria for Patient Selection

| Parameters | Score = 1 | Score = 2 | Score = 3 |
|---|---|---|---|
| Height SDS | <–2.5 | <3.5 | — |
| GHBP SDS | <–2 | <–2.5 | <–3 |
| IGF-I SDS | <–2 | <–3 | <–4 |
| Max. stim. GH (μg/L) | >10 | >15 | >20 |
| Pre-treatment Growth Rate (cm/yr) | <4 | — | — |

Those patients treated with hGH (those given in Table IX who are not listed under the "GH responsive" column as "na") were injected subcutaneously with PROTROPIN® brand GH (all treated patients except Patient 2) and NUTROPIN® brand GH (Patient 2), at about 0.3 mg/kg/week for at least 6 months.

Sample Preparation and PCR Amplification

Lymphocytes were isolated from 1.5 to 10 mL of blood from each patient using either LeucoPREP Cell Separation Tubes (Becton Dickenson) or LSM Lymphocyte Separation Medium (Organon Teknika) and transformed by Epstein Barr Virus (EBV). Katz et al., *J. Infect. Dis.*, 160: 589–598 (1989). DNA was isolated from EBV-transformed lymphocytes or directly from fresh lymphocytes using the QIAamp Blood Kit (Qiagen Inc.). Genomic fragments of the GHR, specific for the coding exons 2 through 9 and their flanking splice sites, were amplified by PCR using intronic primers. The coding portion of exon 10 was amplified in three overlapping fragments in order to restrict the fragment size to less than 400 base pairs (bp). The location and sequence of the intronic primers are as follows:

| Exon | Fragment Size (bp) | Name | Sequence (5' to 3') | |
|---|---|---|---|---|
| 2 | 154 | 101 | TCGTGGGCTTTACCTTAC | (SEQ ID NO: 39) |
|   |   | 102 | CAAAACACTGAGGGTGGA | (SEQ ID NO: 40) |
| 3 | 240 | 154.1 | TACACAGGGTCATATCAGATTG | (SEQ ID NO: 41) |
|   |   | 154.2 | CTATTCCAGTTACTACCATCCC | (SEQ ID NO: 42) |
| 4 | 188 | 105 | CTGATTTCATGCCTTGCC | (SEQ ID NO: 43) |
|   |   | 106 | AGAAAGGCATGATGGTGG | (SEQ ID NO: 44) |
| 5 | 286 | 107B2 | ACTTAAGCTACAACATGATT | (SEQ ID NO: 45) |
|   |   | 108B1 | GCTTCCCCATTTATTTAGT | (SEQ ID NO: 46) |
| 6 | 229 | 109 | ATGCTCTGTTGAATTGCAC | (SEQ ID NO: 47) |

-continued

| Exon | Fragment Size (bp) | Name | Sequence (5' to 3') | |
|---|---|---|---|---|
| | | 110 | GTGTAAGGTGTAGCAACAT | (SEQ ID NO: 48) |
| 7 | 249 | 111a | GACTCTTTGGCCAATATG | (SEQ ID NO: 49) |
| | | 112a | AAGCCAGGTTAGCTACTA | (SEQ ID NO: 50) |
| 8 | 205 | 113B1 | GAAACTGTGCTTCAACTAGTC | (SEQ ID NO: 51) |
| | | 114B1 | GGTCTAACACAACTGGTACA | (SEQ ID NO: 52) |
| 9 | 179 | 115 | ATGTAGCTTTTAACATCTCAA | (SEQ ID NO: 53) |
| | | 116 | ATGACAGGAGTCTTCAGG | (SEQ ID NO: 54) |
| 10a | 311 | 117B | GAGTTTCTTTTCATAGATCTTC | (SEQ ID NO: 55) |
| | | 8 | TTAACCTCTGTGGCTGAG | (SEQ ID NO: 56) |
| 10b | 396 | 9 | ACATGAGGGTACCTCAGA | (SEQ ID NO: 57) |
| | | 10 | CAGAAGTAGGCATTGTCC | (SEQ ID NO: 58) |
| 10c | 375 | 11 | GGAAATGGTCTCACTCTG | (SEQ ID NO: 59) |
| | | 12 | CCAAAGAAAGGCTAAGGC | (SEQ ID NO: 60) |

DNA (100 ng) was amplified in 50 μL containing 0.2 mM dNTPs, 2 units Taq Polymerase (Perkin Elmer Corp.), 1.5 mM MgCl$_2$, 7 μCi $^{33}$P-α-dATP (dupont New England Nuclear), and 15 ng of each primer for 40 cycles (1 minute, 94° C.; 1 minute, 55° C.; 1 minute, 72° C. with 5 seconds added per cycle). The final cycle was followed by 1 minute 94° C. and cooling to 22° C. over 30 minutes. PCR products were electrophoresed in 2% agarose to check for contamination and to verify fragment size.

Total RNA (5–10 μg) was prepared from the EBV-transformed lymphocytes by the acid phenol method (Chomczynski and Sacchi, *Anal. Biochem.*, 162: 156–159 [1987]) and reverse transcribed (Perkin Elmer Corp., RT kit) using random primers (Promega Corp.). PCR amplification of the CHR cDNA was carried out by a nested PCR strategy. Exons 3–10 were amplified in 3 fragments. Nested primers were used to generate smaller fragments (220–415 bp). Cycle conditions were as follows: denaturation at 95° C. for 3 minutes followed by 30 cycles of 95° C., 1 minute; 55° C., 1 minute; 72° C., 1 minute; and finally 72° C. for 10 minutes. The sequences of the primers used in the nesting primer strategy were as follows:

Three RT-PCR fragments (5' to 3'):

1. C1.1-C2.1r

C1.1: GTCCTACAGGTATGGATCTCT (SEQ ID NO: 61)

C3.1r: GAATATCTGCATTGCGTGGTG (SEQ ID NO: 62)

Internal nested PCR products:

C1.1-C1.1r

C1.1: GTCCTACAGGTATGGATCTCT (SEQ ID NO: 61)

C1.1r: CTGGTATAGAACAGCTGTATG (SEQ ID NO: 63)

ex4-ex4.r ex4: ATTCTTCTAAGGAGCCTAAATTCACCA (SEQ ID NO: 64)

ex4.r: CCACCATTGCTAGTTAGCTTG (SEQ ID NO: 65)

ex5-c3.1r ex5: ATGGACTCAAGAATGGAAAGAATG (SEQ ID NO: 66)

c3.1r: GAATATCTGCATTGCGTGGTG (SEQ ID NO: 62)

2. C5.1-C8

C5.1: CACCACGCAATGCAGATATTC (SEQ ID NO: 67)

C8: CTCATGGTCACTGCTTAGAAG (SEQ ID NO: 68)

Internal nested PCR products:

C5.1-C5.1r

C5.1: CACCACGCAATGCAGATATTC (SEQ ID NO: 67)

C5.1r: GTTACATAGAGCACCTCACTG (SEQ ID NO: 69)

n7-C6.1 n7: ATGGACCCTATATTGACAACATC (SEQ ID NO: 70)

C6.1: CCTTTAATCTTTGGAACTGGAAC (SEQ ID NO: 71)

C7-C7.r

C7: GGGCTAACAGTGATGCTATTT (SEQ ID NO: 72)

C7.R: GCTTAGAAGTCTGTCTGTGTC (SEQ ID NO: 73)

3. C9-C14

C9: GCTAGATATTGATGAGCCAGA (SEQ ID NO: 74)

C14: GCTAAGGCATGATTTTGTTCA (SEQ ID NO: 75)

Internal nested PCR products:

C9-C10

C9: GCTAGATATTGATGAGCCAGA (SEQ ID NO: 74)

C10: GTCGATGTTTGACAGTGAACT (SEQ ID NO: 76)

C11.1-C12.1

C11.1: GAAGGAGCTGAGTCAACTCAC (SEQ ID NO: 77)

C12.1: GCTTGGCTGTATGTGTGATTC (SEQ ID NO: 78)

C13-C14

C13: TACTTCTGTGAGGCAGATGCC (SEQ ID NO: 79)

C14: GCTAAGGCATGATTTTGTTCA (SEQ ID NO: 75)

Single-Strand Conformation Analysis

SSCA was carried out on the products from each PCR reaction. 2–4 μL of the reaction mixture was mixed with an equal volume of loading buffer, denatured at 100° C. for 2 minutes and placed on ice. Samples were electrophoresed at room temperature in 0.5×MDE gels (AT Biochem Inc.) with either 1% or 10% glycerol, according to the manufacturer's instructions. Gels were dried on filter paper and autoradiographed.

DNA Sequencing

Mutations detected as aberrant bands by SSCA were confirmed by sequencing. Direct cycle sequencing of the PCR products was carried out with the amplification primers or internal (nested) primers described above and dye-terminator chemistry on the ABI373 sequencer (Applied Biosystems Division of Perkin Elmer Corp.) following standard protocols or using the Ampli-Cycle kit (Perkin Elmer Corp.) and $^{33}$P-α-dATP (duPont New England Nuclear). In addition, multiple subclones from each fragment suspected of containing a mutation were generated in M13mp19 or pBluescript KS+, sequenced with the M13–21 dye-primer, and analyzed on the ABI373 sequencer.

GH Binding Assay

To examine binding of GH to the mutant receptors, recombinant GHR extracellular domains harboring the mutations were engineered. This was done using oligonucleotide-mediated, site-directed mutagenesis, expression in *E. coli*, and purification. Clackson and Wells, *Science*, 267: 383–386 (1995); Fuh et al., *J. Biol. Chem.*, 265: 3111–3115 (1990); Bass et al., *Proc. Natl. Acad. Sci. USA*, 88: 4498–4502 (1991). Affinity for GH was determined by competitive displacement of GH from the mutant receptors using radio-iodinated GH as a tracer. Spencer et al., *J. Biol. Chem.*, 263: 7862–7867 (1988). Dissociation constants (Kds) were calculated by Scatchard analysis. Anti-GHR monoclonal antibody (Mab) 5 (Barnard et al., *Endocrinology*, 115: 1805 [1984]; Cunningham et al., *Science*, 254: 821 [1991]) was used to precipitate the GHR:GH complex. Mab 5 prevents receptor homodimerization, allowing the Kd for the initial 1:1 interaction to be determined free from the effects of dimerization. Clackson and Wells, supra; Cunningham et al., supra.

Results

Fourteen children with ISS were selected with a core score of 4 or above in the selection criteria (Table VIII). Clinical data for these patients are listed in Table IX.

TABLE IX

| Pat. No. | Score | Sex | Age[1] (yr) | Height SDS | GHBP SDS | IGF-I SDS | IGFBP-3 SDS | Max. Stim. GH (μg/L) | Pre-$R_x$ growth rate (cm/yr) | 1st yr growth rate (cm/yr) | GH responsive |
|---|---|---|---|---|---|---|---|---|---|---|---|
| 1 | 9 | M | 3.0 | −5.1 | ***[2] | −0.7 | na[3] | 42.0 | 2.0 | 3.0[7]–6.0[8] | yes[5,6] |
| 2 | 7 | M | 11.6 | −3.1 | ***[2] | −1.2 | na | 18.8 | 4.1 | 5.7 | yes[6] |
| 3 | 9 | M | 7.8 | −3.3 | −2.7 | −4.5 | na | 12.5 | 3.1 | 7.1 | yes[6] |
| 4 | 9 | M | 8.7 | −2.9 | −2.8 | −4.2 | −3.9 | 20.7 | 5.5 | 5.8 | no[6] |
| 5 | 9 | M | 7.8 | −3.4 | −2.6 | −3.7 | na | 48.9 | 2.9 | nc[4] | na |
| 6 | 10 | F | 14.6 | −5.5 | −2.8 | −8.2 | −5.2 | 18.0 | 2.7 | 7.8 | yes[6] |
| 7 | 7 | F | 3.5 | −3.2 | −2.6 | −2.3 | −3.5 | 19.2 | 7.1 | na | na |
| 8 | 10 | M | 9.3 | −2.5 | −2.8 | −6.1 | na | 18.7 | 2.1 | 7.2 | yes[6] |
| 9 | 7 | M | 10.0 | −3.2 | −3.0 | −2.3 | −3.3 | 20.8 | 1.2 | 7.3 | yes[6] |
| 10 | 6 | M | 7.9 | −3.2 | −2.8 | −3.0 | na | 15.6 | 4.4 | 8.4 | yes[6] |
| 11 | 4 | M | 9.8 | −1.6 | −2.3 | −2.0 | −1.3 | 19.3 | 4.2 | 9.1 | yes[6] |
| 12 | 8 | F | 7.9 | −3.1 | −2.5 | −3.5 | na | 21.6 | 6.3 | 9.0 | yes[6] |
| 13 | 8 | M | 12.8 | −3.4 | −2.3 | −4.1 | na | 16.3 | 1.5 | na | na |
| 14 | 7 | M | 8.1 | −3.5 | −2.0 | −3.2 | na | 11.7 | 3.9 | 8.3 | yes[6] |

[1]Age at enrollment into substurdy;
[2]Level of GHBP at or below the limit of detection;
[3]Not available;
[4]Non-compliant;
[5]Positive IGF-I generation test;
[6]growth response with exogenous GH treatment;
[7]at a dose of 0.03 mg/kg/day;
[8]at a dose of about 0.05 mg/kg/day.

Low functional serum GHBP in these patients led to a search for subtle mutations in the GHR gene by a combination of PCR amplification and SSCA. Fragments migrating with altered mobility were observed in four patients: 1, 2, 4, and 7, while no abnormalities were detected in the GHR locus in 24 normal adult controls, with the exception of known polymorphisms in exons 6 and 10 (Leung et al., *Nature*, 330: 537–543 [1987]; Godowkski et al., *Proc. Natl. Acad. Sci. USA*, 86: 8083–8087 [1989]). Thus, there was a significant increase in alterations in the GHR gene in ISS patients with reduced GHBP when compared to a normal population (p=0.014). Each of the genomic PCR fragments suspected of carrying a mutation was sequenced to characterize the alteration causing the aberrant band. See FIGS. 8–11. Patients 1 through 9 were also analyzed by RT-PCR (exons 3–10) and all fragments were of the predicted size, ruling out splicing alterations.

Patient 4 exhibited abnormal bands on SSCA gels when exons 4 and 6 or RT-PCR fragments covering this region were analyzed. The DNA was sequenced and the child found to be a compound heterozygote for a guanosine to adenosine transition in exon 4, introducing a lysine in place of a glutamic acid at position 44 (E44K) in the mature protein (FIG. 8, allele 2 and Table X), and a cytosine to thymidine transition in exon 6, causing an arginine to a cysteine substitution at residue 161 (R161C) (FIG. 8, allele 1 and Table X). RT-PCR products spanning exons 4 through 6 were subcloned and sequenced. The two mutations were found in different subclones; thus, a mutation was found in each of the two alleles. Additionally, genetic analysis of family members indicated that the exon 4 alteration was inherited from the paternal side of the family and the exon 6 mutation from the maternal lineage. The father and paternal grandmother both exhibited the same SSCA band-shift for exon 4 as did the proband, and sequencing confirmed they both carried the identical E44K mutation. Likewise, SSCA and sequencing affirmed the presence of the exon 6 point mutation causing the R161C change in the mother and a maternal uncle. Patient 4 did not respond to exogenous GH with a significant increase in growth rate; his pretreatment growth rate was 5.5 cm/year and his growth rate on GH treatment was 5.8 cm/year.

The effects of these amino acid substitutions on the ability of the receptor to bind GH in a 1:1 complex were investigated using mutant receptor extracellular domain expressed in *E. coli*. Residue E44 is involved in direct contacts with GH (deVos et al., *Science*, 255: 306–312 [1992]) and mutation to alanine reduced ligand binding ($Kd_{MUT}/Kd_{WTb}=17.4$). Clackson and Wells, supra. It was found that introduction of a lysine at position 44 reduces binding 330-fold with respect to the wild-type receptor extracellular domain (Table X). By contrast, residue 161 is not at any intermolecular interface in the human GH:GHR complex (DeVos et al., supra), and its mutation to cysteine caused a 2.1-fold reduction in binding (Table X).

DNA from Patient 2 exhibited a SSCA bandshift with exon genomic PCR fragments. DNA sequencing identified a thymidine to adenosine transversion at position 418 in the cDNA which introduced a stop codon in place of cysteine 122 (C122X). See FIG. 9. Subcloning and sequencing of multiple genomic PCR products from all exons from Patient 2 gave only the wild-type sequence, as did direct sequencing of the genomic PCR fragments. The likelihood that this patient carries a second mutation that was failed to be detected is, therefore, low. Analysis of DNA from both the mother and father of Patient 2 indicated that he inherited the stop codon mutation from his mother. During the first year of treatment with GH his growth rate increased from 4.1 cm/year to 5.7 cm/year (Table IX), indicating a response to exogenous GH. A puberty-associated growth spurt of 10.3. cm/year occurred during his second year of treatment with exogenous GH.

Patients 1 and 7 both carry heterozygous single-base-pair changes which cause amino acid alterations in the GHR from one allele. In Patient 1 an aberrant band was observed with exon 7 genomic PCR fragments. A guanosine to adenosine transition at base pair 686 caused an arginine residue to be replaced with a histidine at amino acid 211 (R211H). See FIG. 10, allele 2. Patient 1 was responsive to GH; he had a positive IGF-I generation test (baseline IGF-I was 56 μg/L and rose to a peak of 179 μg/L after four days of treatment with 0.1 unit GH/kg per injection). Furthermore, his growth rate increased from 2.0 cm/year to 3.0 cm/year on 0.03 mg GH/kg/day and 6.0 cm/year on 0.05 mg GH/kg/day (Table IX).

Patient 7 is likewise affected by an alteration in a single allele. A guanosine to cytosine transversion at base pair 726 introduces an aspartic acid in place of the wild-type glutamic acid at position 224 (E224D). See FIG. 11, allele 2. Patient 7 had never been treated with GH. Neither SSCA nor direct sequencing of the extracellular domain of the GHR detected a second alteration in either of these patients.

Residue R211 is exposed at the surface of the receptor away from any molecular interface. DeVos et al., supra. The histidine mutant produced a protein with an affinity comparable to wild-type receptor, $Kd_{MUT}/Kd_{WT}=1.4$. However, there was a striking reduction in the expression level of the mutant protein; it was expressed at a level about $10^{-4}$ that of wild-type. The arginine 211 to glycine LS-associated mutation reported by Amselem et al., *Hum. Mol. Genet.*, 2: 355–359 (1993), results in an undetectable level of expression. A similar effect on the receptor's affinity for GH was observed for the R224D substitution (Table X). The conservative E224D substitution was not expected to perturb GH binding and, indeed, it was found that substitution with aspartic acid ($Kd_{MUT}/Kd_{WT}=1.6$) had little effect on affinity.

TABLE X

Mutations in the GHR Gene

| Patient | Exon | Base Change | Zygosity | Amino Acid Alteration | GH Binding $Kd_{[Mabs]}$ (nM) | $Kd_{MUT}/Kd_{WT}$ |
|---|---|---|---|---|---|---|
| 1 | 7 | G->A at 686 | het. | R211H | 0.50 ± 0.02 | 1.4 |
| 2 | 5 | T->A at 418 | het. | C122X | nd[2] | nd |
| 4 | 4 | G->A at 184 | comp. het. | E44K | 112 ± 19 | 330 |
| 4 | 6 | C->T at 535 | comp. het. | R161C | 0.73 ± 0.15 | 2.1 |
| 7 | 7 | G->C at 726 | het. | E224D | 0.54 ± 0.07 | 1.6 |

[1]Expression of this mutant receptor extracellular domain was reduced by approximately four orders of magnitude compared to wild-type.
[2]nd = not done

EXAMPLE V

The etiology of growth failure is unknown for many children with marked short stature. Recent data suggests that heterozygous extracellular GHR gene mutations in some Idiopathic Short Stature (ISS) children selected for low GHBP levels may cause partial GHIS. *NEJM* 333: 1093–1098 (1995). To assess whether partial GHIS due to heterozygous GHR gene mutations exists in a less selective population of ISS children, we have analyzed the GHR gene in 34 out of 121 ISS children enrolled in a long term trial of GH therapy. All children in the study had stimulated GH>10 μg/L; the baseline mean height was −2.8 SDS and IGF-I was −0.9. These patients have been treated with GH (0.3 mg/kg/wk) for up to nine years. We analyzed an additional 11 patients with ISS who were not part of the clinical trial and for whom less growth data was available. None of these children had the phenotypic features of Laron syndrome.

Genomic DNA was extracted from Epstein Barr Virus-transformed lymphocytes, and exons 2–10 of the GHR gene were amplified by PCR. Amplified sequences were examined for subtle mutations by the technique of single strand conformational polymorphism (SSCP) analysis on MDE gels with 0% or 10% glycerol. Orita et al., *Genomics*, 5: 874–879 (1989); Soto and Sukumar, *PCR Meth. Appl.*, 2: 96–98 (1992) and any aberrant SSCP bands were reamplified and the DNA sequence determined by standard Dye-Terminator chemistry and separation on the ABD373 or ABD377 automated sequencer. SSCP analysis relies on differences in secondary structure assumed by single-stranded DNA molecules which differ by as little as a single base change. These differences in secondary structure result in variation in electrophoretic mobility in nondenaturing acrylamide-based gels. The efficiency of detecting mutations with SSCP analysis varies from approximately 90% for fragments under 200 base pairs in size to 70–80% for the 200 to 400 base pair size range. Prosser, *Tibtech,* 11: 238–246 (1993). 9 of the 44 ISS children in this less selected population carried mutations in the GHR gene. No abnormalities were detected in the GHR locus in seven control children and 34 control adults.

Three ISS patients had extracellular domain mutations and 6 carried mutations in the intracellular domain of the GH receptor. (Table 1).

Figure 14:
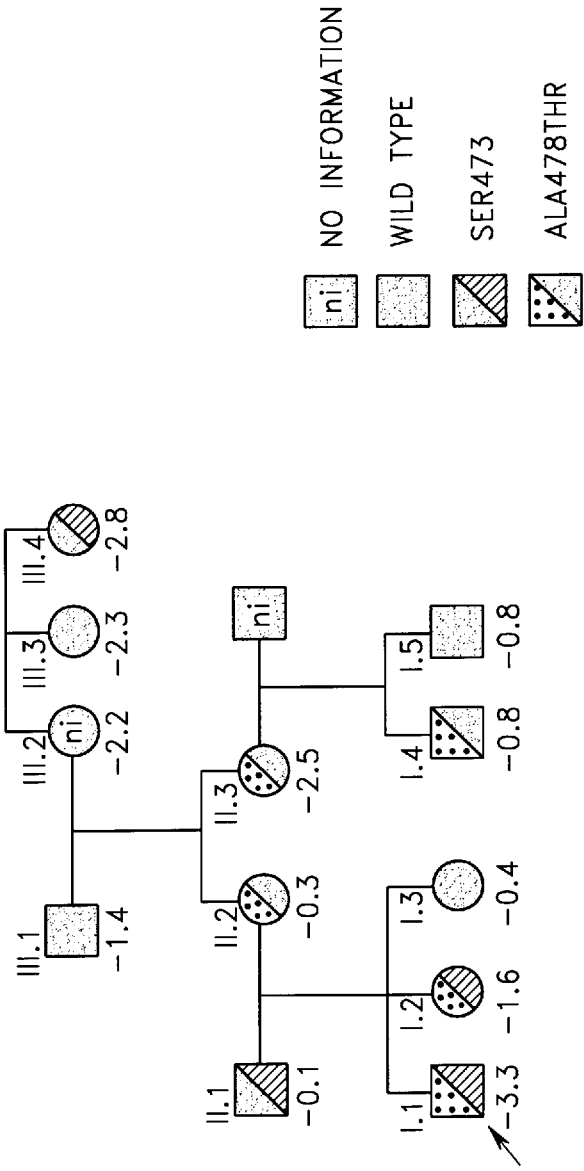

Patient 13 presented at $6^{10}/_{12}$ years of age with severe growth retardation (−4 SDS), delayed bone age ($4^{6}/_{12}$ years) and a growth rate of 3.8 cm/year. Growth hormone levels were normal, as were IGF-BP3 and GHBP levels. However, his IGF-I levels were low and did not rise in an IGF-I generation test (GH at 0.06 mg/kg/d for 5 days) (Table 1). A trial of GH therapy was given at a dose of 0.6 mg/kg/week. The patient responded with a first year growth rate of 10 cm/year and his IGF-I levels increased significantly (57 ng/mL to 339 ng/mL: normal range 88–474). Analysis of the GHR gene revealed that he carried two single base pair changes, one in each allele of the GHR gene: a silent base pair change in codon 473 (which codes for a serine residue) (FIGS. 12A–12C) and a G to A substitution in codon 478 which introduces a threonine in place of the normal alanine (Ala478Thr) (FIGS. 13A–13C). The Ser473 polymorphism was inherited from his father and the Ala478Thr from his mother (FIG. 14). The Ser473 polymorphism has been observed in three other short individuals (one IUGR patient, one ISS patient and one short adult (proband's maternal great aunt)) and in none of the normal statured controls. It remains to be seen if it has any effect on GHR mRNA processing or stability.

Figure 17:
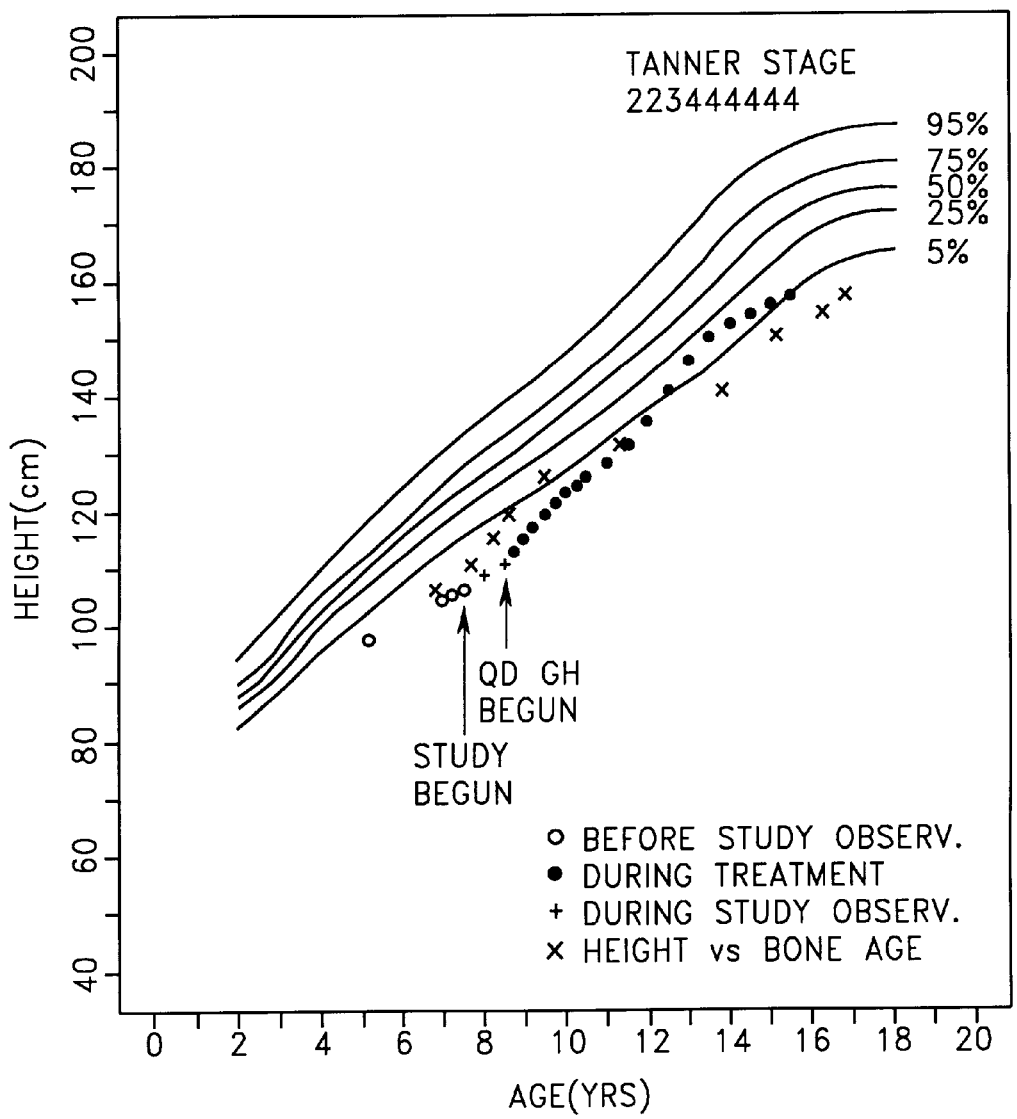

Patients 27 and 32 both carried two single base pair changes in exon 10. One changes cysteine 422 to phenylalanine (Cys422Phe) (FIGS. 15A–15C) and the second replaces proline 561 with threonine (Pro561Thr) (FIGS. 16A–16C). Patient 27 is homozygous or hemizygous for these two changes, thus the both mutations are in the same allele of the gene. Patient 32 is heterozygous for the two alterations. We do not know if these two mutations lie in the same allele or not. No growth data is available for Patient 27. Patient 32 presented with severe short stature (height −3.4 SDS), normal growth hormone levels, and GHBP, IGF-I and IGF-BP3 levels close to the mean (Table 1). Patient 32 had a good response to GH therapy, his pretreatment growth rate of 4.4 cm/year improved to 9.1 cm/year during the first year of therapy and his growth chart (FIG. 17) shows his long term response to GH therapy. The combination of these two mutations has been reported previously in a patient with growth failure and low serum GHBP levels and an inconsistent response to GH. *JCEM,* 76:54–59 (1993).

Patient 44 carries two single base pair changes. Threonine 306 is replaced by a proline due to a single base pair mutation (FIGS. 18A–18C). This patient also carries the Ser473 polymorphism observed in Patient 13 (FIG. 1). We have no clinical or growth response data for this patient.

Figure 19:
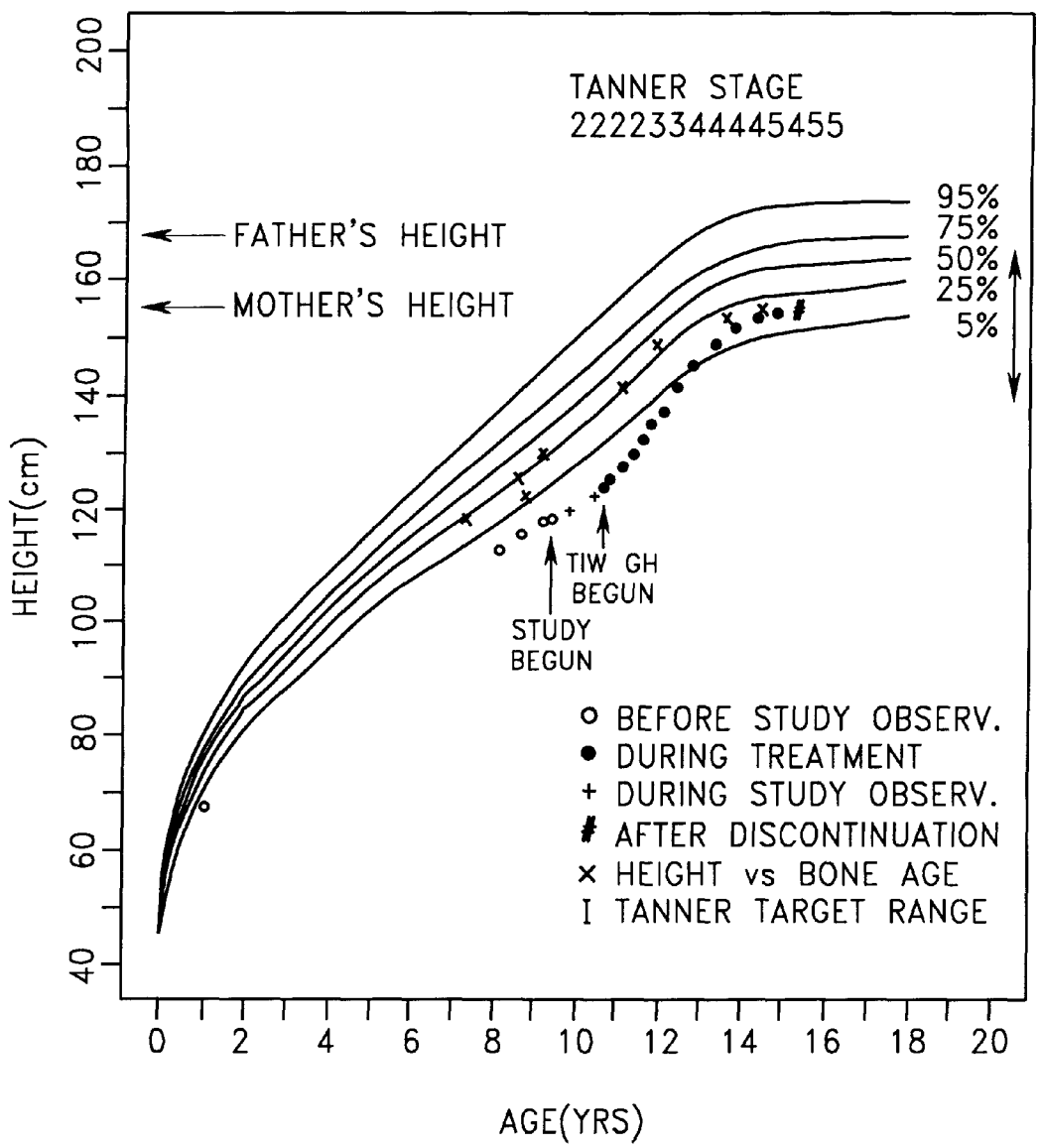

Patient 48 is heterozygous for one amino acid substitution; cysteine 422 is replaced by phenylalanine (Cys422Phe) (FIGS. 15A–15C). This is due to the same base pair substitution seen in Patients 27 and 32. The clinical data (Table 1) show that this girl presented with short stature (−2.8 SDS), low GHBP and IGF-I levels and normal IGF-BP3 levels. She responded to GH therapy with an increase in her growth rate from 4.1 cm/year pretreatment to 8.2 cm/year during her first year of therapy. Her growth curve (FIG. 19) shows her continued response to GH and her attainment of a final height within the range predicted from her parents' heights.

Figure 20B:
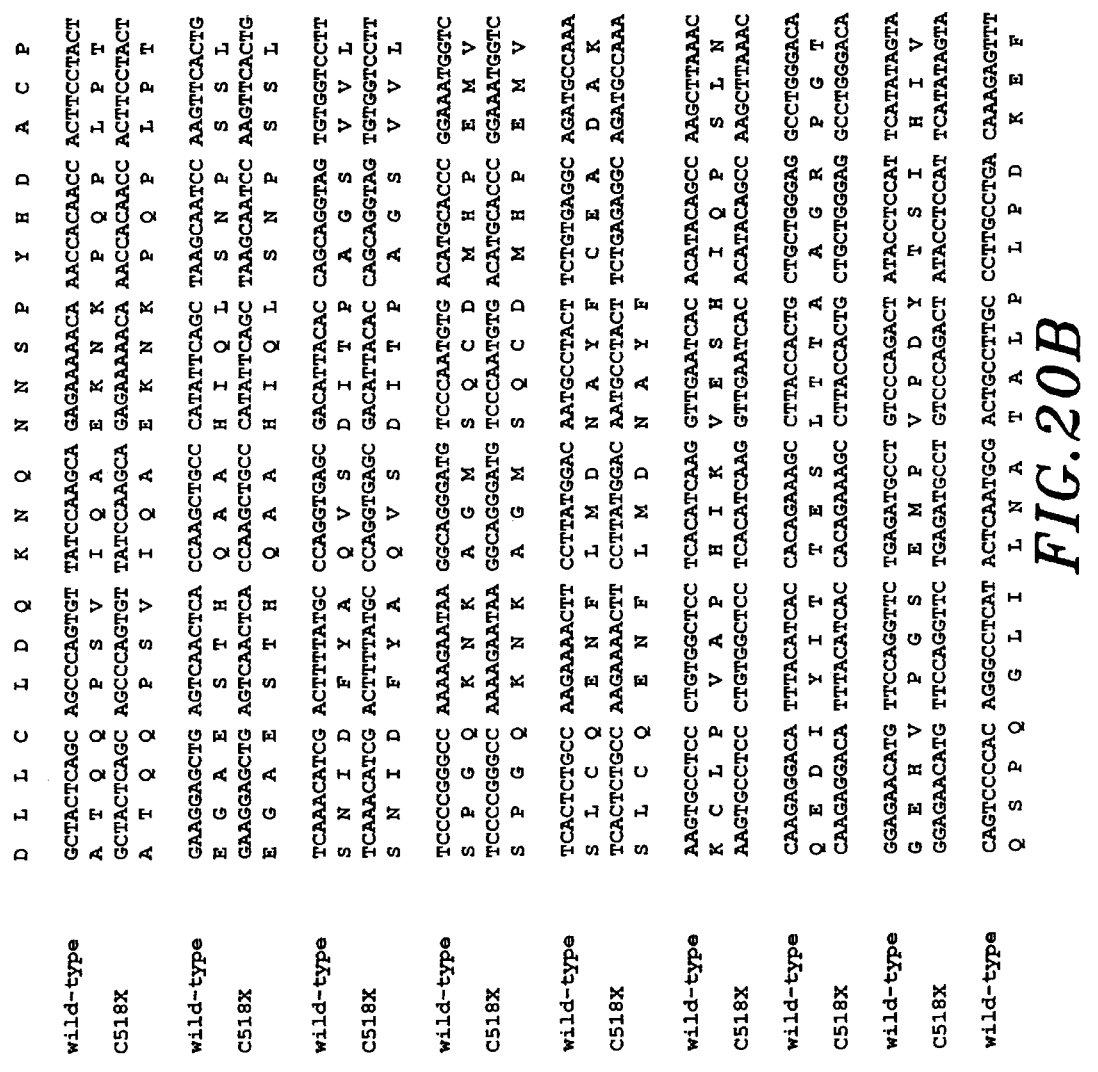
Figure 21:
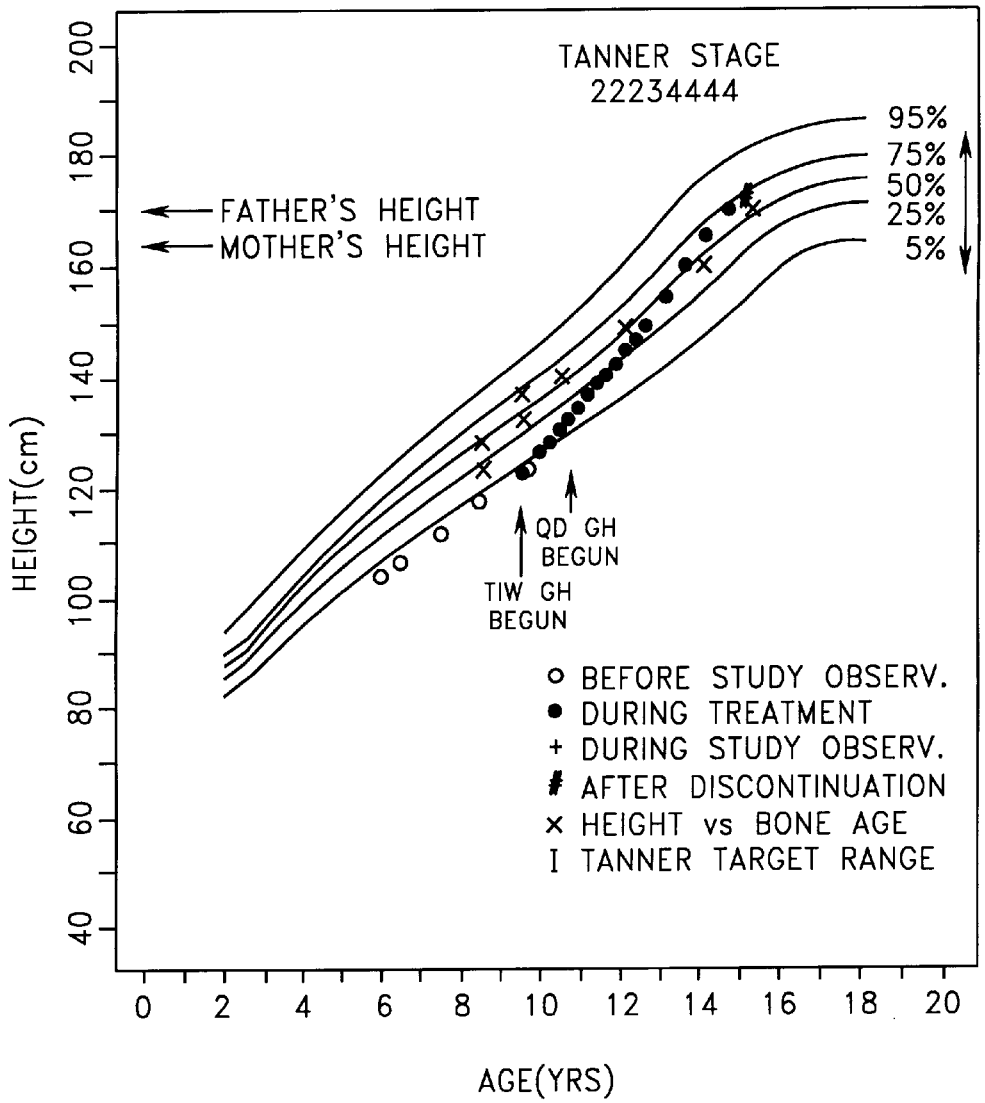

The GHR gene in Patient 49 is disrupted by two single base pair mutations. One results in the replacement of threonine 306 with a proline (Thr306Pro) (FIGS. 18A–18C); this is the same mutation as that seen in patient 44. The second mutation causes cysteine 518 to be replaced with a stop codon (Cys518Stop) (FIGS. 20A–20C), resulting in a truncated protein missing the carboxy-terminal 107 amino acids. This patient was −1.9 SDS for height and had normal GH levels and low GHBP, IGF-I and IGF-BP3 levels (Table 1). His growth curve growth curve (FIG. 21) reflects his improved growth rate on GH therapy (from 4.7 cm/year to 9.0 cm/year during first year of therapy) and attainment of a final height within the range predicted by his parents' heights.

These data suggest that heterogeneous intracellular GH receptor defects may be the cause of poor growth in a subset of non-GH-deficient short stature patients. These GH receptor defects differ from the extracellular mutations observed in complete GH-insensitivity (Laron) syndrome since they affect intracellular domain of the protein.

TABLE 1

ISS Patients with Intracellular Mutations

| Patient # | Sex | Age yrs | Height SDS | GHBP SDS | IGF-I SDS | IGFB P-3 SDS | Max. St imGH$\mu$g/L | PRE-R$_x$ GR cm/yr | 1$^{ST}$ YEAR GR cm/yr | GHR Analysis |
|---|---|---|---|---|---|---|---|---|---|---|
| 13 | M | 6 | −3.3 | 0.4 | −3.1 | −2.9 | 15.3 | 3.8 | 10(0.6 mg/kg/wk) | het S473 het A478T |
| 27 | M | 9 | na | na | na | na | na | na | na | hom/hem C422F, P561T |
| 32 | M | 8.5 | −3.4 | 0.6 | −0.5 | −0.3 | 10.2 | 4.4 | 9.1 | het C422F, P561T |
| 44 | na | na | na | na | na | na | na | na | na | het T306P, S473 |
| 48 | F | 10.5 | −2.8 | −1.1 | −1.9 | 0.2 | 34.1 | 4.1 | 8.2 | het C422F |

TABLE 1-continued

ISS Patients with Intracellular Mutations

| Patient # | Sex | Age yrs | Height SDS | GHBP SDS | IGF-I SDS | IGFB P-3 SDS | Max. St imGH$\mu$g/ L | PRE-$R_x$ GR cm/yr | $1^{ST}$ YEAR GR cm/yr | GHR Analysis |
|---|---|---|---|---|---|---|---|---|---|---|
| 49 | M | 9.6 | −1.9 | −1.6 | −0.7 | −1.5 | 19.0 | 4.7 | 9.0 | het T306P, C518X | na = not available
het = heterozygous
hom = homozygous
hem = hemizygous

Laron syndrome (LS) is a rare autosomal recessive condition characterised by severe GH resistance (1). The main clinical features of this syndrome are extreme postnatal growth failure combined with a typical facial appearance of midfacial hypoplasia with a flat nasal bridge. Infants may also suffer episodes of hypoglycaemia (1,2). Biochemically the GH resistance is manifest by elevated circulating GH levels combined with low or undetectable insulin like growth factor-I (IGF-I) and low IGF-binding protein-3 (IGFBP-3) which fail to respond to exogenous human GH (1).

The defect in LS lies at the level of the GH receptor (GHR) (3–9). This receptor belongs to the GH-prolactin-cytokine receptor superfamily and consists of 3 domains: an extracellular domain responsible for hormone binding and receptor dimerisation, a transmembrane domain, and an intracellular domain which initiates intracellular signalling (10,11). Although the first defect in the GHR to be identified in LS was a complex gene deletion (3), all the subsequent significant defects to be identified have resulted from point mutations confined to the extracellular domain of the receptor (4–9). Kou et al described one LS patient with 2 heterozygous DNA polymorphisms within the intracellular domain on the same allelle but the functional significance of these variants is yet to be established (12).

A soluble form of the GHR called high affinity GH binding protein (GHBP) is present in the circulation of normal individuals and acts as a reservoir and buffer for circulating GH (10,13,14). It is thought to be produced as a result of proteolytic cleavage of the extracellular domain from the rest of the receptor protein in man, although in rodents it has been shown to be produced as a result of alternative splicing (15,16). Initial measurement of GHBP in LS subjects revealed absent or extremely low levels, consistent with the hypothesis that the molecular defects detected in the receptor diminished or reduced the binding of GH (17).

More recently it has emerged that up to 20% of otherwise classical LS patients are GHBP "positive" with normal or even elevated GHBP (1,18). In this subgroup only one GHR mutation has been reported which involves the homozygous substitution of a highly conserved aspartate residue by a histidine at a position in the extracellular domain of the receptor known to be critical for receptor homodimerisation (D152H). Duquesnoy et al have demonstrated that failure of receptor dimerisation was indeed the mechanism of action of this mutation, and that GH binding was unaffected, explaining the normal GHBP (9).

No LS individual with a functionally significant defect outside of the extracellular domain of the GHR has been described although mutagenesis experiments have demonstrated that the majority of the intracellular domain of the GHR is required to mediate full cellular responsiveness to GH (19–22). Hence naturally occurring mutations resulting in deletion or severe disruption of the intracellular domain of the receptor might be expected to give rise to severe GH resistance with preservation of GHBP activity.

We describe two related LS patients who have severe GH resistance with GHBP activity above the normal range. Analysis of the GHR of both individuals revealed they are homozygous for an arginine to threonine substitution at the N-terminal end of the intracellular domain of the GHR. As the nucleotide substitution is located at a critical position in the 5' splice donor site of exon 8 the mutation results in the skipping of exon 8 resulting in a mutant GHR with no functional transmembrane or intracellular domain.

Methods

Patients. Patients 1 and 2 are first cousins born of a highly consanguineous pedigree originating from Kashmir, Pakistan. NS presented at the age of 2.5 yrs with severe short stature (height SDS −5.4) and a typical facial phenotype. GH levels were notably elevated with basal levels of 638 mU/I. Basal IGF-I levels were undetectable at <20 ng/ml (NR 40–150ng/ml) and IGFBP-3 levels were less than the 5th centile for age at 180 ng/ml (NR 1410–2970ng/ml) (23). Administration of exogenous hGH (0.1 lu/kg/day sc for 4 days) produced no significant response in either the IGF-I or IGFBP-3 levels confirming severe GH resistance. GHBP was >95th centile for age at 78.2% (1) with normal GH binding affinity. Remeasurement of GHBP after 6 months of IGF-I therapy revealed no change (level 82.1%) despite a good response to treatment with her height velocity increasing to 8.7 cm/yr. Her parents who are first cousins are of normal height. Her mother has recently given birth to another daughter who appears normal at this stage. Patient 2, a male first cousin has recently presented with growth failure (ht SDS −5.2), the typical facial appearance of LS and micropenis at the age of 2.2 yrs. Initial investigations have revealed a basal GH of 810 mU/I and basal IGF-1 levels of <20 ng/ml.

Amplification of genomic DNA by polymerase chain reaction and DNA sequencing. Leukocyte genomic DNA was prepared from patients and family members by standard methods. In patient 1, exons 4–10 including the intron-exon boundaries were individually amplified by polymerase chain reaction (PCR) using primer pairs (of which the antisense was biotinilated) deduced from the published DNA sequence (3) (Sequences available on request). The PCR products were submitted to direct solid phase genomic sequencing using streptavidin-coated paramagnetic beads (Dynal, Oslo, Norway) and single stranded Sequenase technology (U.S. Biochemical Corp., Cleveland, Ohio). DNA sequences from $^{35}S$ autoradiography were compared to the published GHR sequence (3).

Restriction enzyme analysis. The mutation R274T creates a restriction site for Mae II. Oligonucleotide primers 8a and 8b were used to amplify exon 8 of the GHR of patients 1 and 2 and the parents of patient 1 from leukocyte genomic DNA by PCR (For primer sequences see table 1). The placental DNA of patient 1's newborn sister was also amplified using the same primers. 10 µl of this PCR product was then digested with Mae II and separated on a 6% polyacrilamide gel. DNA was visualised by ethidium bromide staining.

cDNA analysis

Lymphoblastoid cell lines were generated from the lymphocytes of patient 1 by Epstein-Barr virus (EBV) transformation using standard procedures. Cellular RNA was isolated from these EBV-transformed lymphocytes and control lymphocytes collected from peripheral blood of a normal subject using a single step method (Biogenesis, Bournemouth, UK). 15 µg of this RNA was then converted to cDNA in a reverse transcription reaction primed by random hexamers. GHR cDNA spanning exons 7–10 was amplified using the nested PCR approach depicted in FIG. 3a. The sequence of PCR primers are listed in Table A. In the last round of PCR, primer P6 was biotinilated and single strands for direct sequencing were obtained and sequenced as described above.

GH, IGF-1, IGFBP-3 and GHBP analysis. GH was determined by enzyme-linked immunosorbent assay. IGF-I was measured by specific radioimmunoassay (RIA) after acid-ethanol extraction (24). IGFBP-3 was also measured using a specific RIA (25). GHBP was measured by HPLC gel filtration using the method described by Postel-Vinay et al (26). No correction was made for the high GH concentration.

Measurement of GHBP binding affinity

A Scatchard plot was obtained from competition binding experiments using 50 µl plasma. Analysis was performed using the program Ligand (27).

Results

Figure 22:
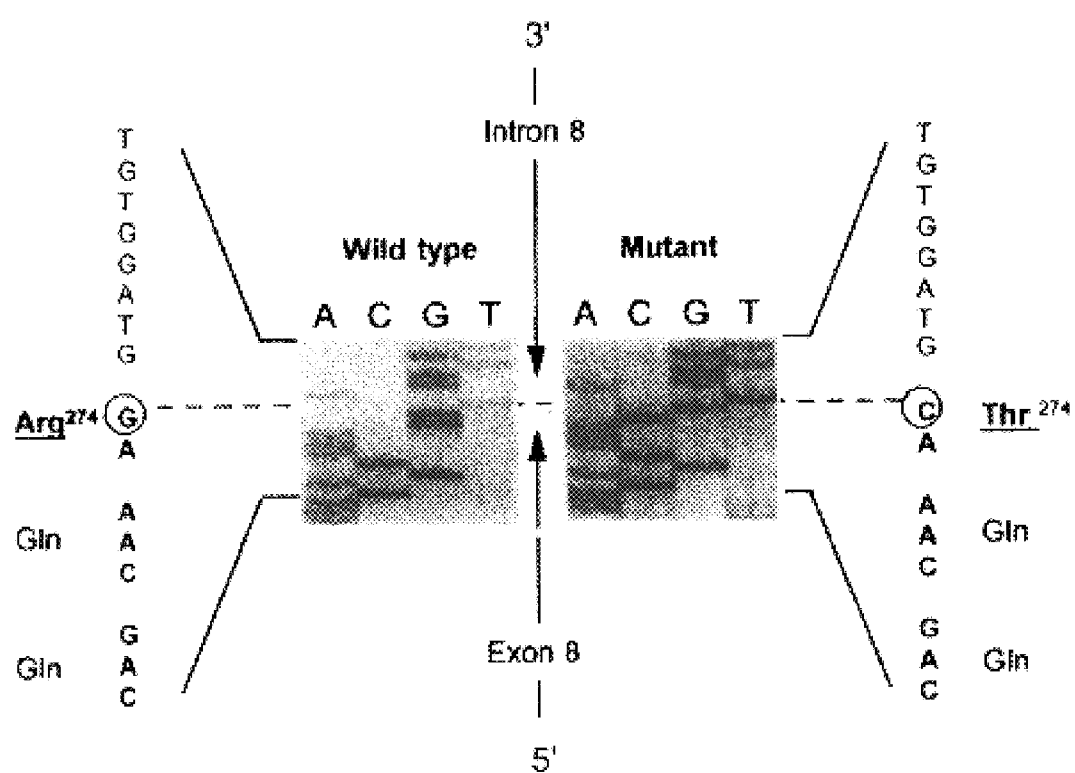
FIG. 22 is a sequencing autoradiograph of the exon/intron junction of exon 8 of the GHR showing the wild-type sequence and the mutant sequence of patient 1. Patient 1 is homozygous for a G to C transversion within codon 274 generating and ACG (Thr) codon in place of an AGG (Arg) codon.

Identification of a missense mutation at the −1 position of the 5' donor splice site of exon 8 of the GHR Sequencing of the GHR in patients 1 and 2 revealed the homozygous substitution of a G by a C at nucleotide 91 of exon 8 (FIG. 22), which is located at the -1 position of the 5' splice donor site. DNA sequencing revealed no additional alteration from the published sequence or that of a control subject. Patient 1's parents were heterozygotes for this mutation.

This nucleotide substitution results in the replacement of arginine (AGG) by threonine (ACG) at amino acid 274 of the mature GHR (R274T), which is predicted to be the fourth amino acid of the intracellular domain of the receptor protein (10).

Restriction enzyme mapping

Figure 23A:
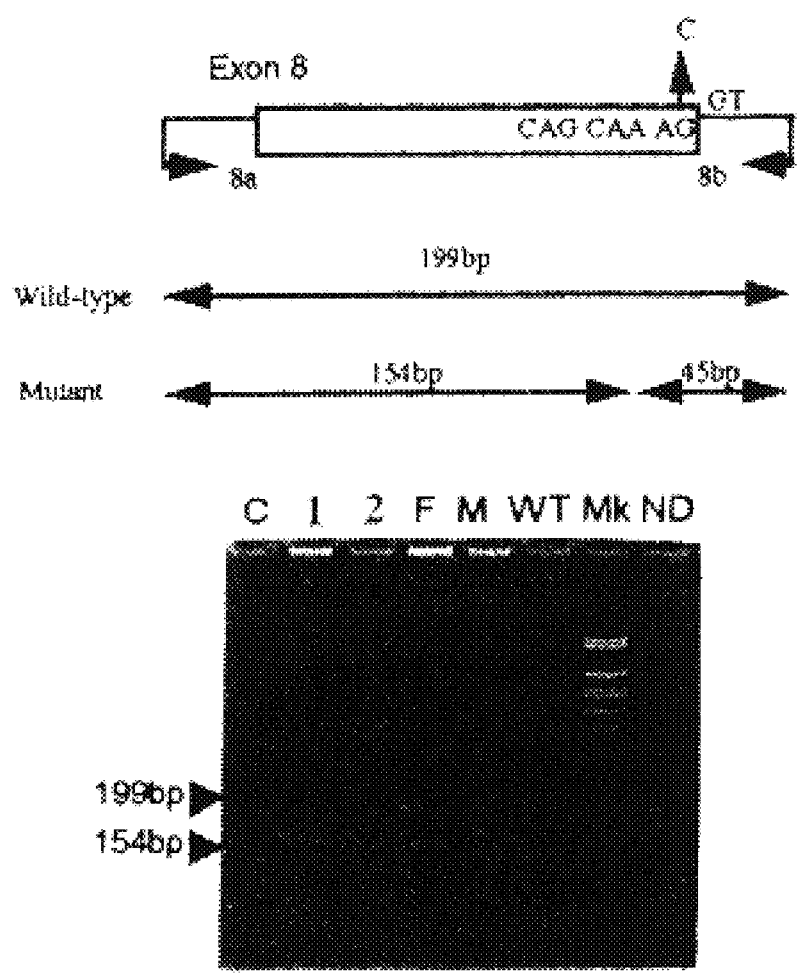
FIGS. 23(A and B) is a restriction enzyme mapping of PCR-amplified DNA from the family members.
Figure 23B:
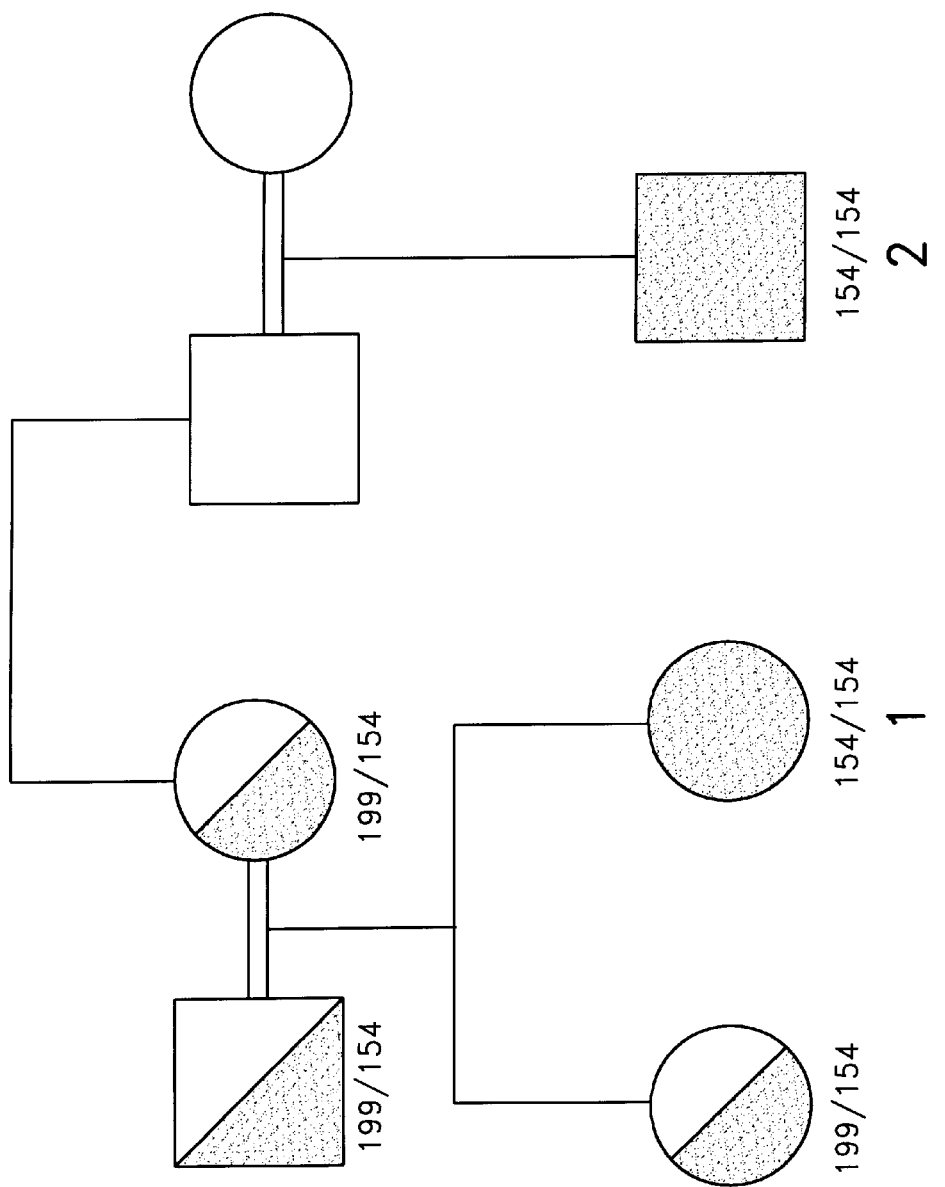

The mutation creates a recognition site for the restriction enzyme Mae II. Amplification of a 199 bp fragment of exon 8 GHR containing this mutation followed by digestion with Mae II yields 154 and 45 bp fragments whereas the normal fragment will remain uncut. As shown in FIG. 23, restriction enzyme analysis of the parents of patient 1 gave a mixed digestion pattern confirming their heterozygous status, whereas for patients 1 and 2 only the shorter 154 bp fragment can be seen demonstrating their homozygosity for the mutation. Digestion of GHR exon 8 from the placental DNA obtained from the newborn brother of patient 1 demonstrated that he is heterozygous for the mutation.

cDNA analysis cDNA amplification from control lymphocytes using primers P4 and P5 produced a band of 267 bp as expected. From the EBV-transformed lymphocytes obtained from patient 1, only a smaller product of 176 bp was obtained. Direct sequencing of these reverse transcription-PCR (RT-PCR) products demonstrated that in the GHR mRNA obtained from patient 1, exon 8 was skipped resulting in exon 7 splicing into exon 9 (FIG. 24), whereas the GHR mRNA obtained from the control lymphocytes was normally spliced with exon 8 following exon 7.

Characteristics of the serum GHBP

The GH binding affinity of the GHBP of patient 1 was within normal limits with an association constant (Ka) of $3.09 \times 10^{-8}$M (normal adult range: $3.6–7.4 \times 10^{-8}$M). The maximum binding capacity of plasma for GH (Bmax) was markedly increased to 317 ng/ml of plasma (normal adult range: 24–86 ng/ml). These results suggest that the increase in measurable GHBP reflects an absolute increase in circulating binding protein. The $^{125}$I-hGH-GHBP complex eluted at the expected time from the HPLC column suggesting that the molecular weight of the GHBP in patient 1's plasma is comparable to that of normal subjects.

Discussion

Our results document for the first time LS associated with a homozygous defect in the intracellular domain of the GHR. This mutation at the 5' donor splice site of exon 8 induces the skipping of exon 8 which encodes the transmembrane domain of the GHR. The affected children have a classical phenotype apart from GHBP in the proband which is well above the normal range. The parents, in whom we have demonstrated heterozygosity are of normal stature.

Our finding that this G C transversion at the −1 position of the 5' donor splice site results in exon skipping is not unexpected. The nucleotide G at the −1 position is conserved in 78% of all 5' donor sites and is thought to be critical for normal splicing. Shapiro and Senapathy (28) collated data on 62 other point mutations at 5' splice sites in other genes: in over half of those papers which included data on their effect on the mRNA, exon skipping was the sole aberrant transcription product (28). The other possible consequence of such a mutation is cryptic splice site utilisation but this does not appear to have been the case for this mutation as we were unable to detect any other abnormal RT-PCR fragments.

The skipping of exon 8 in the GHR mRNA also results in exon 9 (which encodes the beginning of the intracellular domain) being transcribed out of frame with a stop codon 5 amino acids downstream. Hence we predict that the mutant GHR protein produced by these individuals would have no transmembrane domain and no functional intracellular domain. This finding is consistent with the severe GH resistance encountered in the patients as such a molecule would not be capable of signal transduction.

The lack of a transmembrane domain would result in the receptor no longer being anchored in the cell membrane, but with a normal extracellular domain it should be capable of binding GH. The elevation in GHBP in patient 1 can therefore be explained on the basis of all the GHR protein she produces being released into the circulation and measurable as GHBP. The finding of normal GH binding affinity in the serum suggests that this elevation in GHBP is not to due to an increase in the affinity of the mutant receptor but reflects an absolute increase in circulating receptors available to bind GH.

This direct relationship between receptor number and measured GHBP provides a unique opportunity to assess the effect of IGF-1 on the levels of the GHR gene expression. In normal subjects, it has been suggested that a change in serum GHBP may reflect changes in cellular GHR levels, receptor proteolysis or GHBP clearance (29). Recently, Silbergeld and coworkers reported a fall in serum GHBP after IGF-1 therapy in 3 LS subjects with a possible postreceptor defect, interpreting this finding as evidence that IGF-1 may be a regulatory factor for serum GHBP (30). However in our patient, despite a good response to IGF-1 therapy in terms of growth velocity, her GHBP fell only slightly and is still well above the normal range for her age.

To summarise, we have described the first homozygous mutation affecting the intracellular domain of the receptor in the GHR of 2 patients with LS which appears to have its effect by causing skipping of exon 8 and production of a GHR containing no transmembrane or intracellular domain. We have demonstrated that in homozygous form it clearly segregates with the disease phenotype and is likely to be the causative defect in the GHR of this variant of LS with elevated GHBP. The only other mutation to be identified in this GHBP "positive" variant of LS was found in the extracellular domain of the receptor, demonstrating the molecular heterogeneity of this form of LS. Further studies of patients with this phenotype are likely to yield important insights into GHR function.

REFERENCES

1. Savage, M. O., et al. J Clin Endocrinol Metatab 77:1465–1471.
2. Laron, Z., et al. Isr J Med Sci 2:152–155.
3. Godowski, P. J. Proc Natl Acad Sci, USA 86:8083–8087.
4. Amselem, S., et al. N Engl J Med 321:989–995.
5. Amselem, S., et al. J Clin Invest 87:1098–1102.
6. Berg, M. A., et al. Hum Mutat 1:24–34.
7. Berg, M. A., et al. Am J. Hum. Genet. 52:998–1005.
8. Amselem, S., et al. Hum. Mol. Genet. 2:355–359.
9. Duquesnoy, P., et al. EMBO Journal 13: 1386–1395.
10. Leung, et al. Nature 330:537–543.
11. Bazin, J. F., et al. Proc Natl Acad Sci, USA 87:6934–6938.
12. Kou, K., et al. J Clin Endocrinol Metab 76:54–59.
13. Veldhuis, et al. J Clin Invest 91:629–641.
14. Baumann, et al. J. Clin Endocrinol Metab 64:657–660.
15. Baumbach, et al. Genes & Development 3:1199–1205.
16. Sotiropoulos, et al. Endocrinology 132:1863–1865.
17. Daughaday, et al. Proc Natl Acad Sci, USA 84:4636–4640.
18. Buchanan, et al. Clin Endocrinol 35:179–185.
19. Goujon, et al. Proc Natl Acad Sci, USA 91:957–961.
20. Billestrup, et al. [Review]. P.S.E.B.M. 206(3):205–209.
21. Sotiropoulos, et al. Endocrinology 135:1292–1298.
22. Wang, Y-D, et al. Mol Endocrinol 303–307.
23. Blum, et al. Insulin-like growth factors and their binding proteins. Functional endocrinologic diagnosis in children and adolescents. M. B. Ranke, editor, J. J. Verlag, Mannheim. 102–117.
24. Bang, P., et al. Acta Endocrinologica 124:620–629.
25. Blum, W., et al. Journal of Clinical Endocrinology & Metabolism 70:1292–1298.
26. Tar, A., et al. Journal of Clinical Endocrinology & Metabolism 71:1202–1207.
27. Munson, et al. Analytical Biochemistry 107,220–239.
28. Shapiro, et al. Nucl Acids Res 15:7155–7174.
29. Fontoura, et al. Clin Endocrinol 37:249:253.
30. Silbergeld, A., et al. P.S.E.B.M. 206:324–327.

Conclusion

A subgroup of children with ISS have phenotypes which implicate partial GHIS in the etiology of their short stature. The hypothesis posed herein of reduced GHR signaling as exemplified by lower levels of IGF-I and higher GH concentrations with lower GHBP levels has been confirmed through the identification of GHR mutations in short, non-GH deficient patients selected for low GHBP and low IGF-I. None of 24 normal controls exhibited sequence alterations detectable by SSCA, while 4 out of 14 selected ISS patients had identifiable single-base pair alterations (p=0.014). Since SSCA is able to detect approximately 80% of known mutations in model systems (Vidal-Puig and Moller, *Biotechniques*, 17: 490–496 [1994]; Ravnik-Glavac et al., *Hum. Mol. Genet.*, 3: 801–807 [1994]), there may be additional mutations present in these ISS patients which were missed.

Two of the four ISS patients with GHR mutations have responded to exogenous GH (Patients 1 and 2 of Table IX). The presence of mutations and the response to GH suggests that these patients may be partially GH insensitive due to dysfunctional GHR. Without being limited to any one theory, it is believed that the inability of Patient 4 to respond to GH most likely reflects the nature of the two mutations carried in his GHR alleles. One alteration reduces receptor affinity for GH 330-fold, presumably rendering this receptor insensitive to physiological or pharmacological levels of GH. The effect of the second alteration, R161C, is not known, but this mutation is severe; in the homozygous state it causes complete GHIS. Amselem et al., supra. The fourth patient (Patient 7) had not yet been treated with GH. It is clear from the results herein that a continuum of GH responsiveness extends from the complete GHIS seen in LS, through severely insensitive ISS patients lacking the phenotypic characteristics of LS syndrome but who may not respond to standard doses of GH, through ISS patients with partial GHIS who are responsive to standard GH therapy, and finally to the normal phenotype.

Patient 4 is a compound heterozygote for the E44K and R161C substitutions, and each parent is heterozygous for one of the two mutations. Parental and grandparental heights are all within the normal range for the adult population; however, the heights of known carriers of a single mutation are below the mean. Patient 2 is heterozygous for the cysteine to stop mutation at position 122 and thus has one allele producing a truncated, presumably unstable, protein. His mother carries the same mutation. Patient 2, now 19 years of age, is more severely affected by the presence of this mutation (height SDS −3.2) than his mother (height SDS −1.4). Without being limited to any one theory, the proband may have inherited a yet undefined mutation from his father (height SDS −1.4) affecting expression of the structurally normal GHR allele or another step in the GH axis. Family 2 is similar to a suspected LS patient and his unaffected mother, both of whom carried two mutations on one allele of the GHR locus. Kou et al., *J.C.E.M.*, 76: 54–59 (1993). The similarity between this patient and Patient 2 suggests, under one theory, that both may be carriers of an unidentified second mutation, analogous to several insulin-insensitive patients in whom reduced levels of insulin receptor mRNA have been observed despite the lack of mutation in any of the exons (reviewed by Taylor et al., *Endocrine Rev.*, 13: 566–595 [1992]).

Two other patients carry heterozygous mutations leading to amino acid substitutions (R211H in Patient 1 and E224D in Patient 7). The parents of Patient 1 both had heights within the normal range for the adult population. Hamill et al., *Am. J. Clin. Nutrition*, 32: 607–629 (1979). Similarly, the father of Patient 7 has a height SDS of −0.43 and his mother's height SDS is +1.4.

LS is an autosomal recessive condition. Affected individuals usually inherit the same mutation from consanguineous parents. Heterozygotes for GHR mutations (parents and siblings of LS patients) may have mild growth abnormalities. Laron, *The Endocrinologist*, 3: 21–28 (1993); Rosenbloom et al., *Acta Paediatr.*, Suppl. 399: 125–127 (1994). Approximately half of heterozygote carriers have levels of GHBP more than 2 SDs below the mean for age. Aguirre et al., *Horm. Res.*, 34: 4–8 (1990); Laron et al., *Acta Endocrinol.*, 121: 603–608 (1989). In addition, Laron, *The Endocrinologist*, supra, reported that the heights of parents and clinically normal siblings of LS patients are typically below the 50th percentile for their sex and ethnic origin. Without being limited to any one theory, partial GHIS resulting in height SDS less than −2 may arise in carriers of heterozygous mutations of the GHR under the influence of particular genotypes at yet unidentified modifier loci, or when the alterations confer a dominant negative phenotype, as has been proposed for heterozygous insulin receptor mutations in several insulin-insensitive patients.

The five mutations identified in the four patients (E44K, C122X, R161C, R211H, E224D) are confined to the extracellular domain of the receptor. The E44K substitution causes a 330-fold reduction in affinity for GH, while alteration of the R161, R211, or E224 residues had subtle effects on ligand binding (Table X).

Residue R211 is distal to both the ligand-binding and dimerization sites of GHR. It is, however, adjacent to the 'WS-like' motif conserved throughout the cytokine receptor superfamily. Residues from the WS-like motif pack tightly with R211 and other amino acid side chains to form a stack of alternating aromatic and basic side chains.

Residue E224 corresponds to the variable residue of the WS-like motif. Like R211, it lies outside the known binding sites on the GHR molecule and mutations do not alter GH binding significantly (Table X). A E224A substitution expressed in mammalian cells in culture had altered subcellular localization. Baumgartner et al., *J. Biol. Chem.*, 269: 29094–29101 (1994). An increased fraction of the total receptor was observed in a nuclear proximal location. It is not known whether this reflects the accumulation of newly synthesized receptor or increased receptor internalization. Without being limited to any one theory, if the E224D mutation causes a similar effect, incorrect processing could result in reduced receptor numbers on the cell surface and a concomitant reduction in serum GHBP levels.

With this study it is shown that the selection of a subset of ISS children with clinical parameters suggestive of a partial insensitivity to GH identifies patients carrying GHR mutations which may affect GHR function. Since the patients studied were selected on the basis of reduced circulating functional GHBP, the mutations must affect ligand binding directly (E44K) or cause a reduction in the availability of cell surface receptor (R161C, R211H and E224D), thereby contributing to a partial GHIS syndrome. Indeed, two of the three ISS patients with GHR mutations who were treated with exogenous GH had GH-responsive partial GHIS.

EXAMPLE VI

Eighty prepubertal children diagnosed as having an average height less than −2 standard deviations below normal height, a serum level of GHBP that is at least 2 standard deviations below the normal level, a serum level of IGF-I that is below the normal mean level, and a mean or maximum stimulated serum level of GH that is at least normal, aged 5–12, are treated as follows: 20 with IGF-I alone, 20 with GH alone, 20 with GH and IGF-I together, and 20 with placebo. When the drugs are given alone, the IGF-I is administered once per day by subcutaneous injection at a dose of 150 μg/kg/day and the GH is administered once per day by subcutaneous injection at a dose of 0.70 mg/kg/week. When the drugs are combined, the IGF-I is administered once per day by subcutaneous injection at a dose of 75 μg/kg/day and the GH is administered once per day by subcutaneous injection at a dose of 0.35 mg/kg/week. The IGF-I formulation is either (a) 10 mg/ml of IGF-I in 20 mM sodium acetate buffer, 2.5 mg/ml (0.25%) phenol, 45 mg/ml mannitol, pH 5.0; or (b) 10 mg/ml of IGF-I in 50 mM sodium acetate buffer, 2.5 mg/ml phenol, 5.84 mg/ml NaCl, and 9 mg/ml benzyl alcohol, pH 5.4. The GH formulation is either Nutropin® or PROTROPIN® brand GH available from Genentech, Inc. The patients are treated for 6 months with this protocol. The increase in height of each patient is measured.

In this study it is expected that IGF-I, GH, or the combination would increase the growth rates of all the patients as compared to those patients treated with placebo.

Alternative designs for clinical trials are as follows:

The same groups and subclass of children are treated in the same mode with GH alone at 0.35 mg/kg/week or 0.70 mg/kg/week, or IGF-I alone at 75, 100, 150, or 200 μg/kg/day. For the combination treatment, GH is used at 0.35 mg/kg/week and IGF-I at 75 or 100 μg/kg/day with or without using a placebo for comparison.

What is claimed is:

1. A method for increasing the growth rate of a human patient having partial growth hormone insensitivity syndrome, comprising administering an effective amount of growth hormone that increases the growth rate of the patient to said patient, whereby said patient has a height less than about −2 standard deviations below normal for age and sex, has a serum level of high-affinity growth hormone binding protein that is at least 2 standard deviations below normal levels, has a serum level of IGF-I that is below normal mean levels, and has a mean or maximum stimulated serum level of growth hormone that is at least normal, wherein the patient has a heterogeneous growth hormone receptor (GHR) gene defect, and does not have Laron syndrome.

2. The method according to claim 1 wherein the patient has an intracellular GHR gene defect.

3. The method according to claim 1 wherein the patient has an extracellular GHR gene defect.

4. A method for increasing the growth rate of a human patient with non-GH-deficient short stature but not Laron syndrome wherein said patient has a heterogeneous growth hormone receptor (GHR) gene defect, comprising detecting whether the patient has a height less than about −2 standard deviations below normal for age and sex, has a serum level of high-affinity growth hormone binding protein that is at least 2 standard deviations below normal levels, has a serum level of IGF-I that is below normal mean levels, and has a mean or maximum stimulated serum level of growth hormone that is at least normal, and, if so, administering an effective amount of growth hormone that increases the growth rate of the patient to said patient.

5. The method according to claim 4 wherein the patient has an intracellular GHR gene defect.

6. The method according to claim 4 wherein the patient has an extracellular GHR gene defect.

7. A method for increasing the growth rate of a human patient with non-GH-deficient short stature but not Laron syndrome wherein said patient has a heterogeneous growth hormone receptor (GHR) gene defect, comprising detecting whether the patient has a height less than about −2 standard deviations below normal for age and sex, has a serum level of high-affinity growth hormone binding protein that is at least 2 standard deviations below normal levels, has a serum level of IGF-I that is below normal levels, and has a mean or maximum stimulated serum level of growth hormone that is at least normal, and, if so, administering an effective amount of IGF-I to said patient.

8. The method according to claim 7 wherein the patient has an intracellular GHR gene defect.

9. The method according to claim 7 wherein the patient has an extracellular GHR gene defect.

10. A method for increasing the growth rate of a human patient having partial growth hormone insensitivity syndrome, comprising administering amounts of IGF-I and growth hormone that increases the growth rate of the patient to said patient which amounts are effective in combination, whereby said patient has a height less than about −2 standard deviations below normal for age and sex, has a serum level of high-affinity growth hormone binding protein that is at least 2 standard deviations below normal levels, has a serum level of IGF-1 that is below normal mean levels, and has a mean or maximum stimulated serum level of growth hormone that is at least normal, wherein the patient has a heterogeneous growth hormone receptor (GHR) gene defect and does not have Laron syndrome.

11. The method of claim 10 wherein the IGF-I and growth hormone are together administered by subcutaneous injections.

12. The method according to claim 10 wherein the patient has an intracellular GHR gene defect.

13. The method according to claim 10 wherein the patient has an extracellular GHR gene defect.

14. A method for increasing the growth rate of a human patient having partial growth hormone insensitivity syndrome whereby said patient has a heterogeneous GHR gene defect comprising administering an effective amount of growth hormone that increases the growth rate of the patient to said patient.

15. A method for increasing the growth rate of a human patient having partial growth hormone insensitivity syndrome whereby said patient has a heterogeneous gene defect comprising administering an effective amount of IGF-I to said patient.

16. The method according to claim 14 or 15 wherein the patient has an intracellular GHR gene defect.

17. The method according to claim 14 or 15 wherein the patient has an extracellular GHR gene defect.

18. A method for increasing the growth rate of a human patient with non-GH-deficient short stature but not Laron syndrome comprising detecting whether the patient has a heterogeneous GHR gene defect, and if so, administering an effective amount of growth hormone that increases the growth rate of the patient to said patient.

19. A method for increasing the growth rate of a human patient with non-GH-deficient short stature but not Laron syndrome comprising detecting whether the patient has a heterogeneous GHR gene defect, and if so, administering an effective amount of IGF-I to said patient.

20. The method according to claim 18 or 19 wherein the patient has an intracellular GHR gene defect.

21. The method according to claim 18 or 19 wherein the patient has an extracellular GHR gene defect.

* * * * *

SEQUENCE LISTING (1) GENERAL INFORMATION:

(iii) NUMBER OF SEQUENCES: 79

(2) INFORMATION FOR SEQ ID NO:1:

(i) SEQUENCE CHARACTERISTICS:
      (A) LENGTH: 445 base pairs
      (B) TYPE: nucleic acid
      (C) STRANDEDNESS: single
      (D) TOPOLOGY: linear (ii) MOLECULE TYPE: DNA (genomic)

(ix) FEATURE:

```
       (A) NAME/KEY: CDS
       (B) LOCATION: 2..445

(xi) SEQUENCE DESCRIPTION: SEQ ID NO:1:

A TCC TCT AAG GAG CCT AAA TTC ACC AAG TGC CGT TCA CCT GAG CGA         46
  Ser Ser Lys Glu Pro Lys Phe Thr Lys Cys Arg Ser Pro Glu Arg
   1               5                  10                  15

GAG ACT TTT TCA TGC CAC TGG ACA GAT GAG GTT CAT CAT GGT ACA AAG       94
Glu Thr Phe Ser Cys His Trp Thr Asp Glu Val His His Gly Thr Lys
                 20                  25                  30

AAC CTA GGA CCC ATA CAG CTG TTC TAT ACC AGA AGG AAC ACT CAA GAA       142
Asn Leu Gly Pro Ile Gln Leu Phe Tyr Thr Arg Arg Asn Thr Gln Glu
             35                  40                  45

TGG ACT CAA GAA TGG AAA GAA TGC CCT GAT TAT GTT TCT GCT GGG GAA       190
Trp Thr Gln Glu Trp Lys Glu Cys Pro Asp Tyr Val Ser Ala Gly Glu
         50                  55                  60

AAC AGC TGT TAC TTT AAT TCA TCG TTT ACC TCC ATC TGG ATA CCT TAT       238
Asn Ser Cys Tyr Phe Asn Ser Ser Phe Thr Ser Ile Trp Ile Pro Tyr
     65                  70                  75

TGT ATC AAG CTA ACT AGC AAT GGT GGT ACA GTG GAT GAA AAG TGT TTC       286
Cys Ile Lys Leu Thr Ser Asn Gly Gly Thr Val Asp Glu Lys Cys Phe
 80                  85                  90                  95

TCT GTT GAT GAA ATA GTG CAA CCA GAT CCA CCC ATT GCC CTC AAC TGG       334
Ser Val Asp Glu Ile Val Gln Pro Asp Pro Pro Ile Ala Leu Asn Trp
                100                 105                 110

ACT TTA CTG AAC GTC AGT TTA ACT GGG ATT CAT GCA GAT ATC CAA GTG       382
Thr Leu Leu Asn Val Ser Leu Thr Gly Ile His Ala Asp Ile Gln Val
            115                 120                 125

AGA TGG GAA GCA CCA TGC AAT GCA GAT ATT CAG AAA GGG TGG ATG GTT       430
Arg Trp Glu Ala Pro Cys Asn Ala Asp Ile Gln Lys Gly Trp Met Val
        130                 135                 140

CTG GAG TAT GAA CTT                                                   445
Leu Glu Tyr Glu Leu
        145

(2) INFORMATION FOR SEQ ID NO:2:

(i) SEQUENCE CHARACTERISTICS:
        (A) LENGTH: 148 amino acids
        (B) TYPE: amino acid
        (D) TOPOLOGY: linear (ii) MOLECULE TYPE: protein (xi) SEQUENCE DESCRIPTION: SEQ ID NO:2:

Ser Ser Lys Glu Pro Lys Phe Thr Lys Cys Arg Ser Pro Glu Arg Glu
 1               5                  10                  15

Thr Phe Ser Cys His Trp Thr Asp Glu Val His His Gly Thr Lys Asn
             20                  25                  30

Leu Gly Pro Ile Gln Leu Phe Tyr Thr Arg Arg Asn Thr Gln Glu Trp
         35                  40                  45

Thr Gln Glu Trp Lys Glu Cys Pro Asp Tyr Val Ser Ala Gly Glu Asn
     50                  55                  60

Ser Cys Tyr Phe Asn Ser Ser Phe Thr Ser Ile Trp Ile Pro Tyr Cys
 65                  70                  75                  80

Ile Lys Leu Thr Ser Asn Gly Gly Thr Val Asp Glu Lys Cys Phe Ser
                 85                  90                  95

Val Asp Glu Ile Val Gln Pro Asp Pro Pro Ile Ala Leu Asn Trp Thr
            100                 105                 110

Leu Leu Asn Val Ser Leu Thr Gly Ile His Ala Asp Ile Gln Val Arg
```

-continued

```
                115                 120                 125
Trp Glu Ala Pro Cys Asn Ala Asp Ile Gln Lys Gly Trp Met Val Leu
    130                 135                 140
Glu Tyr Glu Leu
145
```

(2) INFORMATION FOR SEQ ID NO:3:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..445

(xi) SEQUENCE DESCRIPTION: SEQ ID NO:3:

```
A TCC TCT AAG GAG CCT AAA TTC ACC AAG TGC CGT TCA CCT GAG CGA        46
  Ser Ser Lys Glu Pro Lys Phe Thr Lys Cys Arg Ser Pro Glu Arg
  1               5                   10                  15

AAG ACT TTT TCA TGC CAC TGG ACA GAT GAG GTT CAT CAT GGT ACA AAG     94
Lys Thr Phe Ser Cys His Trp Thr Asp Glu Val His His Gly Thr Lys
            20                  25                  30

AAC CTA GGA CCC ATA CAG CTG TTC TAT ACC AGA AGG AAC ACT CAA GAA    142
Asn Leu Gly Pro Ile Gln Leu Phe Tyr Thr Arg Arg Asn Thr Gln Glu
                35                  40                  45

TGG ACT CAA GAA TGG AAA GAA TGC CCT GAT TAT GTT TCT GCT GGG GAA    190
Trp Thr Gln Glu Trp Lys Glu Cys Pro Asp Tyr Val Ser Ala Gly Glu
            50                  55                  60

AAC AGC TGT TAC TTT AAT TCA TCG TTT ACC TCC ATC TGG ATA CCT TAT    238
Asn Ser Cys Tyr Phe Asn Ser Ser Phe Thr Ser Ile Trp Ile Pro Tyr
65                  70                  75

TGT ATC AAG CTA ACT AGC AAT GGT GGT ACA GTG GAT GAA AAG TGT TTC    286
Cys Ile Lys Leu Thr Ser Asn Gly Gly Thr Val Asp Glu Lys Cys Phe
80                  85                  90                  95

TCT GTT GAT GAA ATA GTG CAA CCA GAT CCA CCC ATT GCC CTC AAC TGG    334
Ser Val Asp Glu Ile Val Gln Pro Asp Pro Pro Ile Ala Leu Asn Trp
                100                 105                 110

ACT TTA CTG AAC GTC AGT TTA ACT GGG ATT CAT GCA GAT ATC CAA GTG    382
Thr Leu Leu Asn Val Ser Leu Thr Gly Ile His Ala Asp Ile Gln Val
            115                 120                 125

AGA TGG GAA GCA CCA CGC AAT GCA GAT ATT CAG AAA GGG TGG ATG GTT    430
Arg Trp Glu Ala Pro Arg Asn Ala Asp Ile Gln Lys Gly Trp Met Val
        130                 135                 140

CTG GAG TAT GAA CTT                                                 445
Leu Glu Tyr Glu Leu
    145
```

(2) INFORMATION FOR SEQ ID NO:4:

(i) SEQUENCE CHARACTERISTICS:
        (A) LENGTH: 148 amino acids
        (B) TYPE: amino acid
        (D) TOPOLOGY: linear (ii) MOLECULE TYPE: protein (xi) SEQUENCE DESCRIPTION: SEQ ID NO:4:

```
Ser Ser Lys Glu Pro Lys Phe Thr Lys Cys Arg Ser Pro Glu Arg Lys
1               5                   10                  15
```

```
Thr Phe Ser Cys His Trp Thr Asp Glu Val His His Gly Thr Lys Asn
             20                  25                  30

Leu Gly Pro Ile Gln Leu Phe Tyr Thr Arg Arg Asn Thr Gln Glu Trp
         35                  40                  45

Thr Gln Glu Trp Lys Glu Cys Pro Asp Tyr Val Ser Ala Gly Glu Asn
     50                  55                  60

Ser Cys Tyr Phe Asn Ser Ser Phe Thr Ser Ile Trp Ile Pro Tyr Cys
 65                  70                  75                  80

Ile Lys Leu Thr Ser Asn Gly Gly Thr Val Asp Glu Lys Cys Phe Ser
                 85                  90                  95

Val Asp Glu Ile Val Gln Pro Asp Pro Ile Ala Leu Asn Trp Thr
            100                 105                 110

Leu Leu Asn Val Ser Leu Thr Gly Ile His Ala Asp Ile Gln Val Arg
            115                 120                 125

Trp Glu Ala Pro Arg Asn Ala Asp Ile Gln Lys Gly Trp Met Val Leu
     130                 135                 140

Glu Tyr Glu Leu
145
```

(2) INFORMATION FOR SEQ ID NO:5:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..172

(xi) SEQUENCE DESCRIPTION: SEQ ID NO:5:

```
G AAC ACT CAA GAA TGG ACT CAA GAA TGG AAA GAA TGC CCT GAT TAT      46
  Asn Thr Gln Glu Trp Thr Gln Glu Trp Lys Glu Cys Pro Asp Tyr
   1               5                  10                  15

GTT TCT GCT GGG GAA AAC AGC TGT TAC TTT AAT TCA TCG TTT ACC TCC    94
Val Ser Ala Gly Glu Asn Ser Cys Tyr Phe Asn Ser Ser Phe Thr Ser
             20                  25                  30

ATC TGG ATA CCT TAT TGT ATC AAG CTA ACT AGC AAT GGT GGT ACA GTG   142
Ile Trp Ile Pro Tyr Cys Ile Lys Leu Thr Ser Asn Gly Gly Thr Val
         35                  40                  45

GAT GAA AAG TGT TTC TCT GTT GAT GAA ATA G                         173
Asp Glu Lys Cys Phe Ser Val Asp Glu Ile
     50                  55
```

(2) INFORMATION FOR SEQ ID NO:6:

(i) SEQUENCE CHARACTERISTICS:
        (A) LENGTH: 57 amino acids
        (B) TYPE: amino acid
        (D) TOPOLOGY: linear (ii) MOLECULE TYPE: protein (xi) SEQUENCE DESCRIPTION: SEQ ID NO:6:

```
Asn Thr Gln Glu Trp Thr Gln Glu Trp Lys Glu Cys Pro Asp Tyr Val
 1               5                  10                  15

Ser Ala Gly Glu Asn Ser Cys Tyr Phe Asn Ser Ser Phe Thr Ser Ile
             20                  25                  30
```

```
Trp Ile Pro Tyr Cys Ile Lys Leu Thr Ser Asn Gly Gly Thr Val Asp
        35                  40                  45

Glu Lys Cys Phe Ser Val Asp Glu Ile
    50                  55
```

(2) INFORMATION FOR SEQ ID NO:7:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 2..151

(xi) SEQUENCE DESCRIPTION: SEQ ID NO:7:

```
G AAC ACT CAA GAA TGG ACT CAA GAA TGG AAA GAA TGC CCT GAT TAT          46
  Asn Thr Gln Glu Trp Thr Gln Glu Trp Lys Glu Cys Pro Asp Tyr
  1               5                   10                  15

GTT TCT GCT GGG GAA AAC AGC TGT TAC TTT AAT TCA TCG TTT ACC TCC        94
Val Ser Ala Gly Glu Asn Ser Cys Tyr Phe Asn Ser Ser Phe Thr Ser
                20                  25                  30

ATC TGG ATA CCT TAT TGT ATC AAG CTA ACT AGC AAT GGT GGT ACA GTG       142
Ile Trp Ile Pro Tyr Cys Ile Lys Leu Thr Ser Asn Gly Gly Thr Val
            35                  40                  45

GAT GAA AAG TGATTCTCTG TTGATGAAAT AG                                  173
Asp Glu Lys
        50
```

(2) INFORMATION FOR SEQ ID NO:8:

(i) SEQUENCE CHARACTERISTICS:
        (A) LENGTH: 50 amino acids
        (B) TYPE: amino acid
        (D) TOPOLOGY: linear (ii) MOLECULE TYPE: protein (xi) SEQUENCE DESCRIPTION: SEQ ID NO:8:

```
Asn Thr Gln Glu Trp Thr Gln Glu Trp Lys Glu Cys Pro Asp Tyr Val
1               5                   10                  15

Ser Ala Gly Glu Asn Ser Cys Tyr Phe Asn Ser Ser Phe Thr Ser Ile
            20                  25                  30

Trp Ile Pro Tyr Cys Ile Lys Leu Thr Ser Asn Gly Gly Thr Val Asp
        35                  40                  45

Glu Lys
    50
```

(2) INFORMATION FOR SEQ ID NO:9:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 41..205

(xi) SEQUENCE DESCRIPTION: SEQ ID NO:9:

```
GACTCTTTGG CCAATATGCG TTTATATTTT GTCTTGAAAG ATG GAC CCT ATA TTG       55
                                             Met Asp Pro Ile Leu
                                              1               5

ACA ACA TCA GTT CCA GTG TAC TCA TTG AAA GTG GAT AAG GAA TAT GAA      103
Thr Thr Ser Val Pro Val Tyr Ser Leu Lys Val Asp Lys Glu Tyr Glu
             10                  15                  20

GTG CGT GTG AGA TCC AAA CAA CGA AAC TCT GGA AAT TAT GGC GAG TTC      151
Val Arg Val Arg Ser Lys Gln Arg Asn Ser Gly Asn Tyr Gly Glu Phe
             25                  30                  35

AGT GAG GTG CTC TAT GTA ACA CTT CCT CAG ATG AGC CAA TTT ACA TGT      199
Ser Glu Val Leu Tyr Val Thr Leu Pro Gln Met Ser Gln Phe Thr Cys
             40                  45                  50

GAA GAA GGTAAAAGAA ATAAAAGATT AAAATAGTAG CTAAC                       240
Glu Glu
    55
```

(2) INFORMATION FOR SEQ ID NO:10:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:10:

```
Met Asp Pro Ile Leu Thr Thr Ser Val Pro Val Tyr Ser Leu Lys Val
 1               5                  10                  15

Asp Lys Glu Tyr Glu Val Arg Val Arg Ser Lys Gln Arg Asn Ser Gly
                 20                  25                  30

Asn Tyr Gly Glu Phe Ser Glu Val Leu Tyr Val Thr Leu Pro Gln Met
             35                  40                  45

Ser Gln Phe Thr Cys Glu Glu
             50                  55
```

(2) INFORMATION FOR SEQ ID NO:11:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 41..205

(xi) SEQUENCE DESCRIPTION: SEQ ID NO:11:

```
GACTCTTTGG CCAATATGCG TTTATATTTT GTCTTGAAAG ATG GAC CCT ATA TTG       55
                                             Met Asp Pro Ile Leu
                                              1               5

ACA ACA TCA GTT CCA GTG TAC TCA TTG AAA GTG GAT AAG GAA TAT GAA      103
Thr Thr Ser Val Pro Val Tyr Ser Leu Lys Val Asp Lys Glu Tyr Glu
             10                  15                  20

GTG CAT GTG AGA TCC AAA CAA CGA AAC TCT GGA AAT TAT GGC GAG TTC      151
Val His Val Arg Ser Lys Gln Arg Asn Ser Gly Asn Tyr Gly Glu Phe
             25                  30                  35

AGT GAG GTG CTC TAT GTA ACA CTT CCT CAG ATG AGC CAA TTT ACA TGT      199
Ser Glu Val Leu Tyr Val Thr Leu Pro Gln Met Ser Gln Phe Thr Cys
             40                  45                  50

GAA GAA GGTAAAAGAA ATAAAAGATT AAAATAGTAG CTAAC                       240
```

Glu Glu
    55

(2) INFORMATION FOR SEQ ID NO:12:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:12:

Met Asp Pro Ile Leu Thr Thr Ser Val Pro Val Tyr Ser Leu Lys Val
 1               5                  10                  15

Asp Lys Glu Tyr Glu Val His Val Arg Ser Lys Gln Arg Asn Ser Gly
            20                  25                  30

Asn Tyr Gly Glu Phe Ser Glu Val Leu Tyr Val Thr Leu Pro Gln Met
        35                  40                  45

Ser Gln Phe Thr Cys Glu Glu
    50                  55

(2) INFORMATION FOR SEQ ID NO:13:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 41..205

(xi) SEQUENCE DESCRIPTION: SEQ ID NO:13:

GACTCTTTGG CCAATATGCG TTTATATTTT GTCTTGAAAG ATG GAC CCT ATA TTG        55
                                            Met Asp Pro Ile Leu
                                             1               5

ACA ACA TCA GTT CCA GTG TAC TCA TTG AAA GTG GAT AAG GAA TAT GAA       103
Thr Thr Ser Val Pro Val Tyr Ser Leu Lys Val Asp Lys Glu Tyr Glu
            10                  15                  20

GTG CGT GTG AGA TCC AAA CAA CGA AAC TCT GGA AAT TAT GGC GAG TTC       151
Val Arg Val Arg Ser Lys Gln Arg Asn Ser Gly Asn Tyr Gly Glu Phe
        25                  30                  35

AGT GAG GTG CTC TAT GTA ACA CTT CCT CAG ATG AGC CAA TTT ACA TGT       199
Ser Glu Val Leu Tyr Val Thr Leu Pro Gln Met Ser Gln Phe Thr Cys
    40                  45                  50

GAA GAA GGTAAAAGAA ATAAAAGATT AAAATAGTAG CTAAC                        240
Glu Glu
    55

(2) INFORMATION FOR SEQ ID NO:14:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:14:

Met Asp Pro Ile Leu Thr Thr Ser Val Pro Val Tyr Ser Leu Lys Val
 1               5                  10                  15

-continued

```
Asp Lys Glu Tyr Glu Val Arg Val Arg Ser Lys Gln Arg Asn Ser Gly
         20                  25                  30
Asn Tyr Gly Glu Phe Ser Glu Val Leu Tyr Val Thr Leu Pro Gln Met
         35                  40                  45
Ser Gln Phe Thr Cys Glu Glu
         50              55
```

(2) INFORMATION FOR SEQ ID NO:15:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 41..205

(xi) SEQUENCE DESCRIPTION: SEQ ID NO:15:

```
GACTCTTTGG CCAATATGCG TTTATATTTT GTCTTGAAAG ATG GAC CCT ATA TTG      55
                                            Met Asp Pro Ile Leu
                                             1               5

ACA ACA TCA GTT CCA GTG TAC TCA TTG AAA GTG GAT AAG GAA TAT GAA    103
Thr Thr Ser Val Pro Val Tyr Ser Leu Lys Val Asp Lys Glu Tyr Glu
             10                  15                  20

GTG CGT GTG AGA TCC AAA CAA CGA AAC TCT GGA AAT TAT GGC GAC TTC    151
Val Arg Val Arg Ser Lys Gln Arg Asn Ser Gly Asn Tyr Gly Asp Phe
         25                  30                  35

AGT GAG GTG CTC TAT GTA ACA CTT CCT CAG ATG AGC CAA TTT ACA TGT    199
Ser Glu Val Leu Tyr Val Thr Leu Pro Gln Met Ser Gln Phe Thr Cys
     40                  45                  50

GAA GAA GGTAAAAGAA ATAAAAGATT AAAATAGTAG CTAAC                      240
Glu Glu
     55
```

(2) INFORMATION FOR SEQ ID NO:16:

(i) SEQUENCE CHARACTERISTICS:
        (A) LENGTH: 55 amino acids
        (B) TYPE: amino acid
        (D) TOPOLOGY: linear (ii) MOLECULE TYPE: protein (xi) SEQUENCE DESCRIPTION: SEQ ID NO:16:

```
Met Asp Pro Ile Leu Thr Thr Ser Val Pro Val Tyr Ser Leu Lys Val
 1               5                  10                  15
Asp Lys Glu Tyr Glu Val Arg Val Arg Ser Lys Gln Arg Asn Ser Gly
             20                  25                  30
Asn Tyr Gly Asp Phe Ser Glu Val Leu Tyr Val Thr Leu Pro Gln Met
         35                  40                  45
Ser Gln Phe Thr Cys Glu Glu
         50              55
```

(2) INFORMATION FOR SEQ ID NO:17:

(i) SEQUENCE CHARACTERISTICS:
        (A) LENGTH: 1025 base pairs
        (B) TYPE: nucleic acid
        (C) STRANDEDNESS: unknown
        (D) TOPOLOGY: unknown (ix) FEATURE:
    (A) NAME/KEY: CDS
    (B) LOCATION: 43..1011

(xi) SEQUENCE DESCRIPTION: SEQ ID NO:17:

```
GAGTTTCTTT TCATAGATCT TCATTTTCTT TCTATTTTCT AG GAA GGA AAA TTA            54
                                                Glu Gly Lys Leu
                                                  1

GAG GAG GTG AAC ACA ATC TTA GCC ATT CAT GAT AGC TAT AAA CCC GAA          102
Glu Glu Val Asn Thr Ile Leu Ala Ile His Asp Ser Tyr Lys Pro Glu
  5                  10                  15                  20

TTC CAC AGT GAT GAC TCT TGG GTT GAA TTT ATT GAG CTA GAT ATT GAT          150
Phe His Ser Asp Asp Ser Trp Val Glu Phe Ile Glu Leu Asp Ile Asp
                 25                  30                  35

GAG CCA GAT GAA AAG ACT GAG GAA TCA GAC ACA GAC AGA CTT CTA AGC          198
Glu Pro Asp Glu Lys Thr Glu Glu Ser Asp Thr Asp Arg Leu Leu Ser
             40                  45                  50

AGT GAC CAT GAG AAA TCA CAT AGT AAC CTA GGG GTG AAG GAT GGC GAC          246
Ser Asp His Glu Lys Ser His Ser Asn Leu Gly Val Lys Asp Gly Asp
         55                  60                  65

TCT GGA CGT ACC AGC TGT TGT GAA CCT GAC ATT CTG GAG ACT GAT TTC          294
Ser Gly Arg Thr Ser Cys Cys Glu Pro Asp Ile Leu Glu Thr Asp Phe
     70                  75                  80

AAT GCC AAT GAC ATA CAT GAG GGT ACC TCA GAG GTT GCT CAG CCA CAG          342
Asn Ala Asn Asp Ile His Glu Gly Thr Ser Glu Val Ala Gln Pro Gln
 85                  90                  95                 100

AGG TTA AAA GGG GAA GCA GAT CTC TTA TGC CTT GAC CAG AAG AAT CAA          390
Arg Leu Lys Gly Glu Ala Asp Leu Leu Cys Leu Asp Gln Lys Asn Gln
                105                 110                 115

AAT AAC TCA CCT TAT CAT GAT GCT TGC CCT GCT ACT CAG CAG CCC AGT          438
Asn Asn Ser Pro Tyr His Asp Ala Cys Pro Ala Thr Gln Gln Pro Ser
            120                 125                 130

GTT ATC CAA GCA GAG AAA AAC AAA CCA CAA CCA CTT CCT ACT GAA GGA          486
Val Ile Gln Ala Glu Lys Asn Lys Pro Gln Pro Leu Pro Thr Glu Gly
        135                 140                 145

GCT GAG TCA ACT CAC CAA GCT GCC CAT ATT CAG CTA AGC AAT CCA AGT          534
Ala Glu Ser Thr His Gln Ala Ala His Ile Gln Leu Ser Asn Pro Ser
    150                 155                 160

TCA CTG TCA AAC ATC GAC TTT TAT GCC CAG GTG AGC GAC ATT ACA CCA          582
Ser Leu Ser Asn Ile Asp Phe Tyr Ala Gln Val Ser Asp Ile Thr Pro
165                 170                 175                 180

GCA GGT AGT GTG GTC CTT TCC CCG GGC CAA AAG AAT AAG GCA GGG ATG          630
Ala Gly Ser Val Val Leu Ser Pro Gly Gln Lys Asn Lys Ala Gly Met
                185                 190                 195

TCC CAA TGT GAC ATG CAC CCG GAA ATG GTC TCA CTC TGC CAA GAA AAC          678
Ser Gln Cys Asp Met His Pro Glu Met Val Ser Leu Cys Gln Glu Asn
            200                 205                 210

TTC CTT ATG GAC AAT GCC TAC TTC TGT GAG GCA GAT GCC AAA AAG TGC          726
Phe Leu Met Asp Asn Ala Tyr Phe Cys Glu Ala Asp Ala Lys Lys Cys
        215                 220                 225

CTC CCT GTG GCT CCT CAC ATC AAG GTT GAA TCA CAC ATA CAG CCA AGC          774
Leu Pro Val Ala Pro His Ile Lys Val Glu Ser His Ile Gln Pro Ser
    230                 235                 240

TTA AAC CAA GAG GAC ATT TAC ATC ACC ACA GAA AGC CTT ACC ACT GCT          822
Leu Asn Gln Glu Asp Ile Tyr Ile Thr Thr Glu Ser Leu Thr Thr Ala
245                 250                 255                 260

GCT GGG AGG CCT GGG ACA GGA GAA CAT GTT CCA GGT TCT GAG ATG CCT          870
Ala Gly Arg Pro Gly Thr Gly Glu His Val Pro Gly Ser Glu Met Pro
                265                 270                 275

GTC CCA GAC TAT ACC TCC ATT CAT ATA GTA CAG TCC CCA CAG GGC CTC          918
```

```
Val Pro Asp Tyr Thr Ser Ile His Ile Val Gln Ser Pro Gln Gly Leu
                280                 285                 290

ATA CTC AAT GCG ACT GCC TTG CCC TTG CCT GAC AAA GAG TTT CTC TCA     966
Ile Leu Asn Ala Thr Ala Leu Pro Leu Pro Asp Lys Glu Phe Leu Ser
            295                 300                 305

TCA TGT GGC TAT GTG AGC ACA GAC CAA CTG AAC AAA ATC ATG CCT        1011
Ser Cys Gly Tyr Val Ser Thr Asp Gln Leu Asn Lys Ile Met Pro
    310                 315                 320

TAGCCTTTCT TTGG                                                    1025
```

(2) INFORMATION FOR SEQ ID NO:18:

(i) SEQUENCE CHARACTERISTICS:
      (A) LENGTH: 323 amino acids
      (B) TYPE: amino acid
      (D) TOPOLOGY: linear (ii) MOLECULE TYPE: protein (xi) SEQUENCE DESCRIPTION: SEQ ID NO:18:

```
Glu Gly Lys Leu Glu Glu Val Asn Thr Ile Leu Ala Ile His Asp Ser
 1               5                  10                  15

Tyr Lys Pro Glu Phe His Ser Asp Asp Ser Trp Val Glu Phe Ile Glu
                20                  25                  30

Leu Asp Ile Asp Glu Pro Asp Glu Lys Thr Glu Glu Ser Asp Thr Asp
            35                  40                  45

Arg Leu Leu Ser Ser Asp His Gly Lys Ser His Ser Asn Leu Gly Val
 50                  55                  60

Lys Asp Gly Asp Ser Gly Arg Thr Ser Cys Cys Glu Pro Asp Ile Leu
 65                  70                  75                  80

Glu Thr Asp Phe Asn Ala Asn Asp Ile His Glu Gly Thr Ser Glu Val
                85                  90                  95

Ala Gln Pro Gln Arg Leu Lys Gly Glu Ala Asp Leu Leu Cys Leu Asp
                100                 105                 110

Gln Lys Asn Gln Asn Asn Ser Pro Tyr His Asp Ala Cys Pro Ala Thr
            115                 120                 125

Gln Gln Pro Ser Val Ile Gln Ala Glu Lys Asn Lys Pro Gln Pro Leu
130                 135                 140

Pro Thr Glu Gly Ala Glu Ser Thr His Gln Ala Ala His Ile Gln Leu
145                 150                 155                 160

Ser Asn Pro Ser Ser Leu Ser Asn Ile Asp Phe Tyr Ala Gln Val Ser
                165                 170                 175

Asp Ile Thr Pro Ala Gly Ser Val Val Leu Ser Pro Gly Gln Lys Asn
            180                 185                 190

Lys Ala Gly Met Ser Gln Cys Asp Met His Pro Glu Met Val Ser Leu
                195                 200                 205

Cys Gln Glu Asn Phe Leu Met Asp Asn Ala Tyr Phe Cys Glu Ala Asp
210                 215                 220

Ala Lys Lys Cys Leu Pro Val Ala Pro His Ile Lys Val Glu Ser His
225                 230                 235                 240

Ile Gln Pro Ser Leu Asn Gln Glu Asp Ile Tyr Ile Thr Thr Glu Ser
                245                 250                 255

Leu Thr Thr Ala Ala Gly Arg Pro Gly Thr Gly Glu His Val Pro Gly
            260                 265                 270

Ser Glu Met Pro Val Pro Asp Tyr Thr Ser Ile His Ile Val Gln Ser
        275                 280                 285
```

```
    Pro Gln Gly Leu Ile Leu Asn Ala Thr Ala Leu Pro Leu Pro Asp Lys
        290                 295                 300

Glu Phe Leu Ser Ser Cys Gly Tyr Val Ser Thr Asp Gln Leu Asn Lys
    305                 310                 315                 320

Ile Met Pro (2) INFORMATION FOR SEQ ID NO:19:

(i) SEQUENCE CHARACTERISTICS:
        (A) LENGTH: 1025 base pairs
        (B) TYPE: nucleic acid
        (C) STRANDEDNESS: unknown
        (D) TOPOLOGY: unknown (ix) FEATURE:
        (A) NAME/KEY: CDS
        (B) LOCATION: 43..1011

(xi) SEQUENCE DESCRIPTION: SEQ ID NO:19:

GAGTTTCTTT TCATAGATCT TCATTTTCTT TCTATTTTCT AG GAA GGA AAA TTA              54
                                              Glu Gly Lys Leu
                                                 1

GAG GAG GTG AAC ACA ATC TTA GCC ATT CAT GAT AGC TAT AAA CCC GAA            102
Glu Glu Val Asn Thr Ile Leu Ala Ile His Asp Ser Tyr Lys Pro Glu
  5                  10                  15                  20

TTC CAC AGT GAT GAC TCT TGG GTT GAA TTT ATT GAG CTA GAT ATT GAT            150
Phe His Ser Asp Asp Ser Trp Val Glu Phe Ile Glu Leu Asp Ile Asp
                 25                  30                  35

GAG CCA GAT GAA AAG ACT GAG GAA TCA GAC ACA GAC AGA CTT CTA AGC            198
Glu Pro Asp Glu Lys Thr Glu Glu Ser Asp Thr Asp Arg Leu Leu Ser
             40                  45                  50

AGT GAC CAT GAG AAA TCA CAT AGT AAC CTA GGG GTG AAG GAT GGC GAC            246
Ser Asp His Glu Lys Ser His Ser Asn Leu Gly Val Lys Asp Gly Asp
         55                  60                  65

TCT GGA CGT ACC AGC TGT TGT GAA CCT GAC ATT CTG GAG ACT GAT TTC            294
Ser Gly Arg Thr Ser Cys Cys Glu Pro Asp Ile Leu Glu Thr Asp Phe
     70                  75                  80

AAT GCC AAT GAC ATA CAT GAG GGT ACC TCA GAG GTT GCT CAG CCA CAG            342
Asn Ala Asn Asp Ile His Glu Gly Thr Ser Glu Val Ala Gln Pro Gln
 85                  90                  95                 100

AGG TTA AAA GGG GAA GCA GAT CTC TTA TGC CTT GAC CAG AAG AAT CAA            390
Arg Leu Lys Gly Glu Ala Asp Leu Leu Cys Leu Asp Gln Lys Asn Gln
                105                 110                 115

AAT AAC TCA CCT TAT CAT GAT GCT TTC CCT GCT ACT CAG CAG CCC AGT            438
Asn Asn Ser Pro Tyr His Asp Ala Phe Pro Ala Thr Gln Gln Pro Ser
            120                 125                 130

GTT ATC CAA GCA GAG AAA AAC AAA CCA CAA CCA CTT CCT ACT GAA GGA            486
Val Ile Gln Ala Glu Lys Asn Lys Pro Gln Pro Leu Pro Thr Glu Gly
        135                 140                 145

GCT GAG TCA ACT CAC CAA GCT GCC CAT ATT CAG CTA AGC AAT CCA AGT            534
Ala Glu Ser Thr His Gln Ala Ala His Ile Gln Leu Ser Asn Pro Ser
    150                 155                 160

TCA CTG TCA AAC ATC GAC TTT TAT GCC CAG GTG AGT GAC ATT ACA CCA            582
Ser Leu Ser Asn Ile Asp Phe Tyr Ala Gln Val Ser Asp Ile Thr Pro
165                 170                 175                 180

GCA GGT AGT GTG GTC CTT TCC CCG GGC CAA AAG AAT AAG GCA GGG ATG            630
Ala Gly Ser Val Val Leu Ser Pro Gly Gln Lys Asn Lys Ala Gly Met
                185                 190                 195

TCC CAA TGT GAC ATG CAC CCG GAA ATG GTC TCA CTC TGC CAA GAA AAC            678
Ser Gln Cys Asp Met His Pro Glu Met Val Ser Leu Cys Gln Glu Asn
            200                 205                 210
```

```
TTC CTT ATG GAC AAT GCC TAC TTC TGT GAG GCA GAT GCC AAA AAG TGC        726
Phe Leu Met Asp Asn Ala Tyr Phe Cys Glu Ala Asp Ala Lys Lys Cys
        215                 220                 225

CTC CCT GTG GCT CCT CAC ATC AAG GTT GAA TCA CAC ATA CAG CCA AGC        774
Leu Pro Val Ala Pro His Ile Lys Val Glu Ser His Ile Gln Pro Ser
        230                 235                 240

TTA AAC CAA GAG GAC ATT TAC ATC ACC ACA GAA AGC CTT ACC ACT GCT        822
Leu Asn Gln Glu Asp Ile Tyr Ile Thr Thr Glu Ser Leu Thr Thr Ala
245                 250                 255                 260

GCT GGG AGG CCT GGG ACA GGA GAA CAT GTT CCA GGT TCT GAG ATG CCT        870
Ala Gly Arg Pro Gly Thr Gly Glu His Val Pro Gly Ser Glu Met Pro
            265                 270                 275

GTC CCA GAC TAT ACC TCC ATT CAT ATA GTA CAG TCC CCA CAG GGC CTC        918
Val Pro Asp Tyr Thr Ser Ile His Ile Val Gln Ser Pro Gln Gly Leu
                280                 285                 290

ATA CTC AAT GCG ACT GCC TTG CCC TTG CCT GAC AAA GAG TTT CTC TCA        966
Ile Leu Asn Ala Thr Ala Leu Pro Leu Pro Asp Lys Glu Phe Leu Ser
                    295                 300                 305

TCA TGT GGC TAT GTG AGC ACA GAC CAA CTG AAC AAA ATC ATG CCT           1011
Ser Cys Gly Tyr Val Ser Thr Asp Gln Leu Asn Lys Ile Met Pro
310                 315                 320

TAGCCTTTCT TTGG                                                       1025
```

(2) INFORMATION FOR SEQ ID NO:20:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:20:

```
Glu Gly Lys Leu Glu Glu Val Asn Thr Ile Leu Ala Ile His Asp Ser
 1               5                  10                  15

Tyr Lys Pro Glu Phe His Ser Asp Asp Ser Trp Val Glu Phe Ile Glu
                20                  25                  30

Leu Asp Ile Asp Glu Pro Asp Glu Lys Thr Glu Glu Ser Asp Thr Asp
            35                  40                  45

Arg Leu Leu Ser Ser Asp His Glu Lys Ser His Ser Asn Leu Gly Val
        50                  55                  60

Lys Asp Gly Asp Ser Gly Arg Thr Ser Cys Cys Glu Pro Asp Ile Leu
 65                 70                  75                  80

Glu Thr Asp Phe Asn Ala Asn Asp Ile His Glu Gly Thr Ser Glu Val
                85                  90                  95

Ala Gln Pro Gln Arg Leu Lys Gly Glu Ala Asp Leu Leu Cys Leu Asp
                100                 105                 110

Gln Lys Asn Gln Asn Asn Ser Pro Tyr His Asp Ala Phe Pro Ala Thr
            115                 120                 125

Gln Gln Pro Ser Val Ile Gln Ala Glu Lys Asn Lys Pro Gln Pro Leu
        130                 135                 140

Pro Thr Glu Gly Ala Glu Ser Thr His Gln Ala Ala His Ile Gln Leu
145                 150                 155                 160

Ser Asn Pro Ser Ser Leu Ser Asn Ile Asp Phe Tyr Ala Gln Val Ser
                165                 170                 175

Asp Ile Thr Pro Ala Gly Ser Val Val Leu Ser Pro Gly Gln Lys Asn
                180                 185                 190

Lys Ala Gly Met Ser Gln Cys Asp Met His Pro Glu Met Val Ser Leu
```

```
            195                 200                 205
Cys Gln Glu Asn Phe Leu Met Asp Asn Ala Tyr Phe Cys Glu Ala Asp
    210                 215                 220

Ala Lys Lys Cys Leu Pro Val Ala Pro His Ile Lys Val Glu Ser His
225                 230                 235                 240

Ile Gln Pro Ser Leu Asn Gln Glu Asp Ile Tyr Ile Thr Thr Glu Ser
                245                 250                 255

Leu Thr Thr Ala Ala Gly Arg Pro Gly Thr Gly Glu His Val Pro Gly
                260                 265                 270

Ser Glu Met Pro Val Pro Asp Tyr Thr Ser Ile His Ile Val Gln Ser
            275                 280                 285

Pro Gln Gly Leu Ile Leu Asn Ala Thr Ala Leu Pro Leu Pro Asp Lys
        290                 295                 300

Glu Phe Leu Ser Ser Cys Gly Tyr Val Ser Thr Asp Gln Leu Asn Lys
305                 310                 315                 320

Ile Met Pro (2) INFORMATION FOR SEQ ID NO:21:

(i) SEQUENCE CHARACTERISTICS:
        (A) LENGTH: 1025 base pairs
        (B) TYPE: nucleic acid
        (C) STRANDEDNESS: unknown
        (D) TOPOLOGY: unknown (ix) FEATURE:
        (A) NAME/KEY: CDS
        (B) LOCATION: 43..1011

(xi) SEQUENCE DESCRIPTION: SEQ ID NO:21:

GAGTTTCTTT TCATAGATCT TCATTTTCTT TCTATTTTCT AG GAA GGA AAA TTA         54
                                              Glu Gly Lys Leu
                                                    1

GAG GAG GTG AAC ACA ATC TTA GCC ATT CAT GAT AGC TAT AAA CCC GAA       102
Glu Glu Val Asn Thr Ile Leu Ala Ile His Asp Ser Tyr Lys Pro Glu
  5                  10                  15                  20

TTC CAC AGT GAT GAC TCT TGG GTT GAA TTT ATT GAG CTA GAT ATT GAT       150
Phe His Ser Asp Asp Ser Trp Val Glu Phe Ile Glu Leu Asp Ile Asp
                 25                  30                  35

GAG CCA GAT GAA AAG ACT GAG GAA TCA GAC ACA GAC AGA CTT CTA AGC       198
Glu Pro Asp Glu Lys Thr Glu Glu Ser Asp Thr Asp Arg Leu Leu Ser
             40                  45                  50

AGT GAC CAT GAG AAA TCA CAT AGT AAC CTA GGG GTG AAG GAT GGC GAC       246
Ser Asp His Glu Lys Ser His Ser Asn Leu Gly Val Lys Asp Gly Asp
         55                  60                  65

TCT GGA CGT ACC AGC TGT TGT GAA CCT GAC ATT CTG GAG ACT GAT TTC       294
Ser Gly Arg Thr Ser Cys Cys Glu Pro Asp Ile Leu Glu Thr Asp Phe
     70                  75                  80

AAT GCC AAT GAC ATA CAT GAG GGT ACC TCA GAG GTT GCT CAG CCA CAG       342
Asn Ala Asn Asp Ile His Glu Gly Thr Ser Glu Val Ala Gln Pro Gln
 85                  90                  95                 100

AGG TTA AAA GGG GAA GCA GAT CTC TTA TGC CTT GAC CAG AAG AAT CAA       390
Arg Leu Lys Gly Glu Ala Asp Leu Leu Cys Leu Asp Gln Lys Asn Gln
                105                 110                 115

AAT AAC TCA CCT TAT CAT GAT GCT TGC CCT GCT ACT CAG CAG CCC AGT       438
Asn Asn Ser Pro Tyr His Asp Ala Cys Pro Ala Thr Gln Gln Pro Ser
            120                 125                 130

GTT ATC CAA GCA GAG AAA AAC AAA CCA CAA CCA CTT CCT ACT GAA GGA       486
Val Ile Gln Ala Glu Lys Asn Lys Pro Gln Pro Leu Pro Thr Glu Gly
        135                 140                 145
```

```
GCT GAG TCA ACT CAC CAA GCT GCC CAT ATT CAG CTA AGC AAT CCA AGT      534
Ala Glu Ser Thr His Gln Ala Ala His Ile Gln Leu Ser Asn Pro Ser
    150                 155                 160

TCA CTG TCA AAC ATC GAC TTT TAT GCC CAG GTG AGC GAC ATT ACA CCA      582
Ser Leu Ser Asn Ile Asp Phe Tyr Ala Gln Val Ser Asp Ile Thr Pro
165                 170                 175                 180

ACA GGT AGT GTG GTC CTT TCC CCG GGC CAA AAG AAT AAG GCA GGG ATG      630
Thr Gly Ser Val Val Leu Ser Pro Gly Gln Lys Asn Lys Ala Gly Met
                185                 190                 195

TCC CAA TGT GAC ATG CAC CCG GAA ATG GTC TCA CTC TGC CAA GAA AAC      678
Ser Gln Cys Asp Met His Pro Glu Met Val Ser Leu Cys Gln Glu Asn
            200                 205                 210

TTC CTT ATG GAC AAT GCC TAC TTC TGT GAG GCA GAT GCC AAA AAG TGC      726
Phe Leu Met Asp Asn Ala Tyr Phe Cys Glu Ala Asp Ala Lys Lys Cys
        215                 220                 225

CTC CCT GTG GCT CCT CAC ATC AAG GTT GAA TCA CAC ATA CAG CCA AGC      774
Leu Pro Val Ala Pro His Ile Lys Val Glu Ser His Ile Gln Pro Ser
    230                 235                 240

TTA AAC CAA GAG GAC ATT TAC ATC ACC ACA GAA AGC CTT ACC ACT GCT      822
Leu Asn Gln Glu Asp Ile Tyr Ile Thr Thr Glu Ser Leu Thr Thr Ala
245                 250                 255                 260

GCT GGG AGG CCT GGG ACA GGA GAA CAT GTT CCA GGT TCT GAG ATG CCT      870
Ala Gly Arg Pro Gly Thr Gly Glu His Val Pro Gly Ser Glu Met Pro
                265                 270                 275

GTC CCA GAC TAT ACC TCC ATT CAT ATA GTA CAG TCC CCA CAG GGC CTC      918
Val Pro Asp Tyr Thr Ser Ile His Ile Val Gln Ser Pro Gln Gly Leu
            280                 285                 290

ATA CTC AAT GCG ACT GCC TTG CCC TTG CCT GAC AAA GAG TTT CTC TCA      966
Ile Leu Asn Ala Thr Ala Leu Pro Leu Pro Asp Lys Glu Phe Leu Ser
        295                 300                 305

TCA TGT GGC TAT GTG AGC ACA GAC CAA CTG AAC AAA ATC ATG CCT         1011
Ser Cys Gly Tyr Val Ser Thr Asp Gln Leu Asn Lys Ile Met Pro
    310                 315                 320

TAGCCTTTCT TTGG                                                     1025
```

(2) INFORMATION FOR SEQ ID NO:22:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:22:

```
Glu Gly Lys Leu Glu Glu Val Asn Thr Ile Leu Ala Ile His Asp Ser
1               5                   10                  15

Tyr Lys Pro Glu Phe His Ser Asp Asp Ser Trp Val Glu Phe Ile Glu
                20                  25                  30

Leu Asp Ile Asp Glu Pro Asp Glu Lys Thr Glu Glu Ser Asp Thr Asp
            35                  40                  45

Arg Leu Leu Ser Ser Asp His Glu Lys Ser His Ser Asn Leu Gly Val
    50                  55                  60

Lys Asp Gly Asp Ser Gly Arg Thr Ser Cys Cys Glu Pro Asp Ile Leu
65                  70                  75                  80

Glu Thr Asp Phe Asn Ala Asn Asp Ile His Glu Gly Thr Ser Glu Val
                85                  90                  95

Ala Gln Pro Gln Arg Leu Lys Gly Glu Ala Asp Leu Leu Cys Leu Asp
            100                 105                 110
```

-continued

```
Gln Lys Asn Gln Asn Asn Ser Pro Tyr His Asp Ala Cys Pro Ala Thr
        115                 120                 125
Gln Gln Pro Ser Val Ile Gln Ala Glu Lys Asn Lys Pro Gln Pro Leu
130                 135                 140
Pro Thr Glu Gly Ala Glu Ser Thr His Gln Ala Ala His Ile Gln Leu
145                 150                 155                 160
Ser Asn Pro Ser Ser Leu Ser Asn Ile Asp Phe Tyr Ala Gln Val Ser
                165                 170                 175
Asp Ile Thr Pro Thr Gly Ser Val Val Leu Ser Pro Gly Gln Lys Asn
            180                 185                 190
Lys Ala Gly Met Ser Gln Cys Asp Met His Pro Glu Met Val Ser Leu
        195                 200                 205
Cys Gln Glu Asn Phe Leu Met Asp Asn Ala Tyr Phe Cys Glu Ala Asp
    210                 215                 220
Ala Lys Lys Cys Leu Pro Val Ala Pro His Ile Lys Val Glu Ser His
225                 230                 235                 240
Ile Gln Pro Ser Leu Asn Gln Glu Asp Ile Tyr Ile Thr Thr Glu Ser
                245                 250                 255
Leu Thr Thr Ala Ala Gly Arg Pro Gly Thr Gly Glu His Val Pro Gly
            260                 265                 270
Ser Glu Met Pro Val Pro Asp Tyr Thr Ser Ile His Ile Val Gln Ser
        275                 280                 285
Pro Gln Gly Leu Ile Leu Asn Ala Thr Ala Leu Pro Leu Pro Asp Lys
    290                 295                 300
Glu Phe Leu Ser Ser Cys Gly Tyr Val Ser Thr Asp Gln Leu Asn Lys
305                 310                 315                 320
Ile Met Pro
```

(2) INFORMATION FOR SEQ ID NO:23:

(i) SEQUENCE CHARACTERISTICS:
        (A) LENGTH: 1025 base pairs
        (B) TYPE: nucleic acid
        (C) STRANDEDNESS: unknown
        (D) TOPOLOGY: unknown (ix) FEATURE:
        (A) NAME/KEY: CDS
        (B) LOCATION: 43..1011

(xi) SEQUENCE DESCRIPTION: SEQ ID NO:23:

```
GAGTTTCTTT TCATAGATCT TCATTTTCTT TCTATTTTCT AG GAA GGA AAA TTA           54
                                              Glu Gly Lys Leu
                                                       1
GAG GAG GTG AAC ACA ATC TTA GCC ATT CAT GAT AGC TAT AAA CCC GAA         102
Glu Glu Val Asn Thr Ile Leu Ala Ile His Asp Ser Tyr Lys Pro Glu
  5                  10                  15                  20
TTC CAC AGT GAT GAC TCT TGG GTT GAA TTT ATT GAG CTA GAT ATT GAT         150
Phe His Ser Asp Asp Ser Trp Val Glu Phe Ile Glu Leu Asp Ile Asp
                 25                  30                  35
GAG CCA GAT GAA AAG ACT GAG GAA TCA GAC ACA GAC AGA CTT CTA AGC         198
Glu Pro Asp Glu Lys Thr Glu Glu Ser Asp Thr Asp Arg Leu Leu Ser
             40                  45                  50
AGT GAC CAT GAG AAA TCA CAT AGT AAC CTA GGG GTG AAG GAT GGC GAC         246
Ser Asp His Glu Lys Ser His Ser Asn Leu Gly Val Lys Asp Gly Asp
         55                  60                  65
TCT GGA CGT ACC AGC TGT TGT GAA CCT GAC ATT CTG GAG ACT GAT TTC         294
Ser Gly Arg Thr Ser Cys Cys Glu Pro Asp Ile Leu Glu Thr Asp Phe
```

```
            70                  75                  80
AAT GCC AAT GAC ATA CAT GAG GGT ACC TCA GAG GTT GCT CAG CCA CAG         342
Asn Ala Asn Asp Ile His Glu Gly Thr Ser Glu Val Ala Gln Pro Gln
 85                  90                  95                 100

AGG TTA AAA GGG GAA GCA GAT CTC TTA TGC CTT GAC CAG AAG AAT CAA         390
Arg Leu Lys Gly Glu Ala Asp Leu Leu Cys Leu Asp Gln Lys Asn Gln
                    105                 110                 115

AAT AAC TCA CCT TAT CAT GAT GCT TTC CCT GCT ACT CAG CAG CCC AGT         438
Asn Asn Ser Pro Tyr His Asp Ala Phe Pro Ala Thr Gln Gln Pro Ser
                120                 125                 130

GTT ATC CAA GCA GAG AAA AAC AAA CCA CAA CCA CTT CCT ACT GAA GGA         486
Val Ile Gln Ala Glu Lys Asn Lys Pro Gln Pro Leu Pro Thr Glu Gly
            135                 140                 145

GCT GAG TCA ACT CAC CAA GCT GCC CAT ATT CAG CTA AGC AAT CCA AGT         534
Ala Glu Ser Thr His Gln Ala Ala His Ile Gln Leu Ser Asn Pro Ser
        150                 155                 160

TCA CTG TCA AAC ATC GAC TTT TAT GCC CAG GTG AGC GAC ATT ACA CCA         582
Ser Leu Ser Asn Ile Asp Phe Tyr Ala Gln Val Ser Asp Ile Thr Pro
165                 170                 175                 180

GCA GGT AGT GTG GTC CTT TCC CCG GGC CAA AAG AAT AAG GCA GGG ATG         630
Ala Gly Ser Val Val Leu Ser Pro Gly Gln Lys Asn Lys Ala Gly Met
                    185                 190                 195

TCC CAA TGT GAC ATG CAC CCG GAA ATG GTC TCA CTC TGC CAA GAA AAC         678
Ser Gln Cys Asp Met His Pro Glu Met Val Ser Leu Cys Gln Glu Asn
                200                 205                 210

TTC CTT ATG GAC AAT GCC TAC TTC TGT GAG GCA GAT GCC AAA AAG TGC         726
Phe Leu Met Asp Asn Ala Tyr Phe Cys Glu Ala Asp Ala Lys Lys Cys
            215                 220                 225

CTC CCT GTG GCT CCT CAC ATC AAG GTT GAA TCA CAC ATA CAG CCA AGC         774
Leu Pro Val Ala Pro His Ile Lys Val Glu Ser His Ile Gln Pro Ser
        230                 235                 240

TTA AAC CAA GAG GAC ATT TAC ATC ACC ACA GAA AGC CTT ACC ACT GCT         822
Leu Asn Gln Glu Asp Ile Tyr Ile Thr Thr Glu Ser Leu Thr Thr Ala
245                 250                 255                 260

GCT GGG AGG CCT GGG ACA GGA GAA CAT GTT CCA GGT TCT GAG ATG CCT         870
Ala Gly Arg Pro Gly Thr Gly Glu His Val Pro Gly Ser Glu Met Pro
                    265                 270                 275

GTC CCA GAC TAT ACC TCC ATT CAT ATA GTA CAG TCC CCA CAG GGC CTC         918
Val Pro Asp Tyr Thr Ser Ile His Ile Val Gln Ser Pro Gln Gly Leu
                280                 285                 290

ATA CTC AAT GCG ACT GCC TTG CCC TTG CCT GAC AAA GAG TTT CTC TCA         966
Ile Leu Asn Ala Thr Ala Leu Pro Leu Pro Asp Lys Glu Phe Leu Ser
            295                 300                 305

TCA TGT GGC TAT GTG AGC ACA GAC CAA CTG AAC AAA ATC ATG CCT            1011
Ser Cys Gly Tyr Val Ser Thr Asp Gln Leu Asn Lys Ile Met Pro
        310                 315                 320

TAGCCTTTCT TTGG                                                        1025

(2) INFORMATION FOR SEQ ID NO:24:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:24:

Glu Gly Lys Leu Glu Glu Val Asn Thr Ile Leu Ala Ile His Asp Ser
 1               5                  10                  15
```

```
Tyr Lys Pro Glu Phe His Ser Asp Asp Ser Trp Val Glu Phe Ile Glu
             20                  25                  30

Leu Asp Ile Asp Glu Pro Asp Glu Lys Thr Glu Ser Asp Thr Asp
         35                  40                  45

Arg Leu Leu Ser Ser Asp His Glu Lys Ser His Ser Asn Leu Gly Val
     50                  55                  60

Lys Asp Gly Asp Ser Gly Arg Thr Ser Cys Cys Glu Pro Asp Ile Leu
 65                  70                  75                  80

Glu Thr Asp Phe Asn Ala Asn Asp Ile His Glu Gly Thr Ser Glu Val
                 85                  90                  95

Ala Gln Pro Gln Arg Leu Lys Gly Glu Ala Asp Leu Leu Cys Leu Asp
             100                 105                 110

Gln Lys Asn Gln Asn Ser Pro Tyr His Asp Ala Phe Pro Ala Thr
         115                 120                 125

Gln Gln Pro Ser Val Ile Gln Ala Glu Lys Asn Lys Pro Gln Pro Leu
    130                 135                 140

Pro Thr Glu Gly Ala Glu Ser Thr His Gln Ala Ala His Ile Gln Leu
145                 150                 155                 160

Ser Asn Pro Ser Ser Leu Ser Asn Ile Asp Phe Tyr Ala Gln Val Ser
                165                 170                 175

Asp Ile Thr Pro Ala Gly Ser Val Val Leu Ser Pro Gly Gln Lys Asn
            180                 185                 190

Lys Ala Gly Met Ser Gln Cys Asp Met His Pro Glu Met Val Ser Leu
        195                 200                 205

Cys Gln Glu Asn Phe Leu Met Asp Asn Ala Tyr Phe Cys Glu Ala Asp
    210                 215                 220

Ala Lys Lys Cys Leu Pro Val Ala Pro His Ile Lys Val Glu Ser His
225                 230                 235                 240

Ile Gln Pro Ser Leu Asn Gln Glu Asp Ile Tyr Ile Thr Thr Glu Ser
                245                 250                 255

Leu Thr Thr Ala Ala Gly Arg Pro Gly Thr Gly Glu His Val Pro Gly
            260                 265                 270

Ser Glu Met Pro Val Pro Asp Tyr Thr Ser Ile His Ile Val Gln Ser
        275                 280                 285

Pro Gln Gly Leu Ile Leu Asn Ala Thr Ala Leu Pro Leu Pro Asp Lys
    290                 295                 300

Glu Phe Leu Ser Ser Cys Gly Tyr Val Ser Thr Asp Gln Leu Asn Lys
305                 310                 315                 320

Ile Met Pro (2) INFORMATION FOR SEQ ID NO:25:

(i) SEQUENCE CHARACTERISTICS:
        (A) LENGTH: 1025 base pairs
        (B) TYPE: nucleic acid
        (C) STRANDEDNESS: unknown
        (D) TOPOLOGY: unknown (ix) FEATURE:
        (A) NAME/KEY: CDS
        (B) LOCATION: 43..1011

(xi) SEQUENCE DESCRIPTION: SEQ ID NO:25:

GAGTTTCTTT TCATAGATCT TCATTTTCTT TCTATTTTCT AG GAA GGA AAA TTA          54
                                              Glu Gly Lys Leu
                                                1

GAG GAG GTG AAC ACA ATC TTA GCC ATT CAT GAT AGC TAT AAA CCC GAA        102
```

```
            Glu Glu Val Asn Thr Ile Leu Ala Ile His Asp Ser Tyr Lys Pro Glu
              5                  10                  15                  20

TTC CAC AGT GAT GAC TCT TGG GTT GAA TTT ATT GAG CTA GAT ATT GAT                150
Phe His Ser Asp Asp Ser Trp Val Glu Phe Ile Glu Leu Asp Ile Asp
                     25                  30                  35

GAG CCA GAT GAA AAG ACT GAG GAA TCA GAC ACA GAC AGA CTT CTA AGC                198
Glu Pro Asp Glu Lys Thr Glu Glu Ser Asp Thr Asp Arg Leu Leu Ser
         40                  45                  50

AGT GAC CAT GAG AAA TCA CAT AGT AAC CTA GGG GTG AAG GAT GGC GAC                246
Ser Asp His Glu Lys Ser His Ser Asn Leu Gly Val Lys Asp Gly Asp
             55                  60                  65

TCT GGA CGT ACC AGC TGT TGT GAA CCT GAC ATT CTG GAG ACT GAT TTC                294
Ser Gly Arg Thr Ser Cys Cys Glu Pro Asp Ile Leu Glu Thr Asp Phe
 70                  75                  80

AAT GCC AAT GAC ATA CAT GAG GGT ACC TCA GAG GTT GCT CAG CCA CAG                342
Asn Ala Asn Asp Ile His Glu Gly Thr Ser Glu Val Ala Gln Pro Gln
 85                  90                  95                 100

AGG TTA AAA GGG GAA GCA GAT CTC TTA TGC CTT GAC CAG AAG AAT CAA                390
Arg Leu Lys Gly Glu Ala Asp Leu Leu Cys Leu Asp Gln Lys Asn Gln
                    105                 110                 115

AAT AAC TCA CCT TAT CAT GAT GCT TGC CCT GCT ACT CAG CAG CCC AGT                438
Asn Asn Ser Pro Tyr His Asp Ala Cys Pro Ala Thr Gln Gln Pro Ser
                120                 125                 130

GTT ATC CAA GCA GAG AAA AAC AAA CCA CAA CCA CTT CCT ACT GAA GGA                486
Val Ile Gln Ala Glu Lys Asn Lys Pro Gln Pro Leu Pro Thr Glu Gly
            135                 140                 145

GCT GAG TCA ACT CAC CAA GCT GCC CAT ATT CAG CTA AGC AAT CCA AGT                534
Ala Glu Ser Thr His Gln Ala Ala His Ile Gln Leu Ser Asn Pro Ser
150                 155                 160

TCA CTG TCA AAC ATC GAC TTT TAT GCC CAG GTG AGC GAC ATT ACA CCA                582
Ser Leu Ser Asn Ile Asp Phe Tyr Ala Gln Val Ser Asp Ile Thr Pro
165                 170                 175                 180

GCA GGT AGT GTG GTC CTT TCC CCG GGC CAA AAG AAT AAG GCA GGG ATG                630
Ala Gly Ser Val Val Leu Ser Pro Gly Gln Lys Asn Lys Ala Gly Met
                185                 190                 195

TCC CAA TGT GAC ATG CAC CCG GAA ATG GTC TCA CTC TGC CAA GAA AAC                678
Ser Gln Cys Asp Met His Pro Glu Met Val Ser Leu Cys Gln Glu Asn
                200                 205                 210

TTC CTT ATG GAC AAT GCC TAC TTC TGT GAG GCA GAT GCC AAA AAG TGC                726
Phe Leu Met Asp Asn Ala Tyr Phe Cys Glu Ala Asp Ala Lys Lys Cys
            215                 220                 225

CTC CCT GTG GCT CCT CAC ATC AAG GTT GAA TCA CAC ATA CAG CCA AGC                774
Leu Pro Val Ala Pro His Ile Lys Val Glu Ser His Ile Gln Pro Ser
230                 235                 240

TTA AAC CAA GAG GAC ATT TAC ATC ACC ACA GAA AGC CTT ACC ACT GCT                822
Leu Asn Gln Glu Asp Ile Tyr Ile Thr Thr Glu Ser Leu Thr Thr Ala
245                 250                 255                 260

GCT GGG AGG ACT GGG ACA GGA GAA CAT GTT CCA GGT TCT GAG ATG CCT                870
Ala Gly Arg Thr Gly Thr Gly Glu His Val Pro Gly Ser Glu Met Pro
                265                 270                 275

GTC CCA GAC TAT ACC TCC ATT CAT ATA GTA CAG TCC CCA CAG GGC CTC                918
Val Pro Asp Tyr Thr Ser Ile His Ile Val Gln Ser Pro Gln Gly Leu
            280                 285                 290

ATA CTC AAT GCG ACT GCC TTG CCC TTG CCT GAC AAA GAG TTT CTC TCA                966
Ile Leu Asn Ala Thr Ala Leu Pro Leu Pro Asp Lys Glu Phe Leu Ser
295                 300                 305

TCA TGT GGC TAT GTG AGC ACA GAC CAA CTG AAC AAA ATC ATG CCT                   1011
Ser Cys Gly Tyr Val Ser Thr Asp Gln Leu Asn Lys Ile Met Pro
310                 315                 320
```

```
TAGCCTTTCT TTGG                                                  1025
```

(2) INFORMATION FOR SEQ ID NO:26:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:26:

```
Glu Gly Lys Leu Glu Val Asn Thr Ile Leu Ala Ile His Asp Ser
 1               5                  10                  15

Tyr Lys Pro Glu Phe His Ser Asp Asp Ser Trp Val Glu Phe Ile Glu
            20                  25                  30

Leu Asp Ile Asp Glu Pro Asp Glu Lys Thr Glu Glu Ser Asp Thr Asp
        35                  40                  45

Arg Leu Leu Ser Ser Asp His Glu Lys Ser His Ser Asn Leu Gly Val
    50                  55                  60

Lys Asp Gly Asp Ser Gly Arg Thr Ser Cys Cys Glu Pro Asp Ile Leu
65                  70                  75                  80

Glu Thr Asp Phe Asn Ala Asn Asp Ile His Glu Gly Thr Ser Glu Val
                85                  90                  95

Ala Gln Pro Gln Arg Leu Lys Gly Glu Ala Asp Leu Leu Cys Leu Asp
            100                 105                 110

Gln Lys Asn Gln Asn Asn Ser Pro Tyr His Asp Ala Cys Pro Ala Thr
        115                 120                 125

Gln Gln Pro Ser Val Ile Gln Ala Glu Lys Asn Lys Pro Gln Pro Leu
    130                 135                 140

Pro Thr Glu Gly Ala Glu Ser Thr His Gln Ala Ala His Ile Gln Leu
145                 150                 155                 160

Ser Asn Pro Ser Ser Leu Ser Asn Ile Asp Phe Tyr Ala Gln Val Ser
                165                 170                 175

Asp Ile Thr Pro Ala Gly Ser Val Val Leu Ser Pro Gly Gln Lys Asn
            180                 185                 190

Lys Ala Gly Met Ser Gln Cys Asp Met His Pro Glu Met Val Ser Leu
        195                 200                 205

Cys Gln Glu Asn Phe Leu Met Asp Asn Ala Tyr Phe Cys Glu Ala Asp
    210                 215                 220

Ala Lys Lys Cys Leu Pro Val Ala Pro His Ile Lys Val Glu Ser His
225                 230                 235                 240

Ile Gln Pro Ser Leu Asn Gln Glu Asp Ile Tyr Ile Thr Thr Glu Ser
                245                 250                 255

Leu Thr Thr Ala Ala Gly Arg Thr Gly Thr Gly Glu His Val Pro Gly
            260                 265                 270

Ser Glu Met Pro Val Pro Asp Tyr Thr Ser Ile His Ile Val Gln Ser
        275                 280                 285

Pro Gln Gly Leu Ile Leu Asn Ala Thr Ala Leu Pro Leu Pro Asp Lys
    290                 295                 300

Glu Phe Leu Ser Ser Cys Gly Tyr Val Ser Thr Asp Gln Leu Asn Lys
305                 310                 315                 320

Ile Met Pro
```

(2) INFORMATION FOR SEQ ID NO:27:

```
    (i) SEQUENCE CHARACTERISTICS:
        (A) LENGTH: 1025 base pairs
        (B) TYPE: nucleic acid
        (C) STRANDEDNESS: unknown
        (D) TOPOLOGY: unknown (ix) FEATURE:
        (A) NAME/KEY: CDS
        (B) LOCATION: 43..1011

(xi) SEQUENCE DESCRIPTION: SEQ ID NO:27:
```

```
GAGTTTCTTT TCATAGATCT TCATTTTCTT TCTATTTTCT AG GAA GGA AAA TTA       54
                                              Glu Gly Lys Leu
                                                1

GAG GAG GTG AAC CCA ATC TTA GCC ATT CAT GAT AGC TAT AAA CCC GAA     102
Glu Glu Val Asn Pro Ile Leu Ala Ile His Asp Ser Tyr Lys Pro Glu
  5                  10                  15                  20

TTC CAC AGT GAT GAC TCT TGG GTT GAA TTT ATT GAG CTA GAT ATT GAT     150
Phe His Ser Asp Asp Ser Trp Val Glu Phe Ile Glu Leu Asp Ile Asp
                 25                  30                  35

GAG CCA GAT GAA AAG ACT GAG GAA TCA GAC ACA GAC AGA CTT CTA AGC     198
Glu Pro Asp Glu Lys Thr Glu Glu Ser Asp Thr Asp Arg Leu Leu Ser
             40                  45                  50

AGT GAC CAT GAG AAA TCA CAT AGT AAC CTA GGG GTG AAG GAT GGC GAC     246
Ser Asp His Glu Lys Ser His Ser Asn Leu Gly Val Lys Asp Gly Asp
         55                  60                  65

TCT GGA CGT ACC AGC TGT TGT GAA CCT GAC ATT CTG GAG ACT GAT TTC     294
Ser Gly Arg Thr Ser Cys Cys Glu Pro Asp Ile Leu Glu Thr Asp Phe
     70                  75                  80

AAT GCC AAT GAC ATA CAT GAG GGT ACC TCA GAG GTT GCT CAG CCA CAG     342
Asn Ala Asn Asp Ile His Glu Gly Thr Ser Glu Val Ala Gln Pro Gln
 85                  90                  95                 100

AGG TTA AAA GGG GAA GCA GAT CTC TTA TGC CTT GAC CAG AAG AAT CAA     390
Arg Leu Lys Gly Glu Ala Asp Leu Leu Cys Leu Asp Gln Lys Asn Gln
                105                 110                 115

AAT AAC TCA CCT TAT CAT GAT GCT TGC CCT GCT ACT CAG CAG CCC AGT     438
Asn Asn Ser Pro Tyr His Asp Ala Cys Pro Ala Thr Gln Gln Pro Ser
            120                 125                 130

GTT ATC CAA GCA GAG AAA AAC AAA CCA CAA CCA CTT CCT ACT GAA GGA     486
Val Ile Gln Ala Glu Lys Asn Lys Pro Gln Pro Leu Pro Thr Glu Gly
        135                 140                 145

GCT GAG TCA ACT CAC CAA GCT GCC CAT ATT CAG CTA AGC AAT CCA AGT     534
Ala Glu Ser Thr His Gln Ala Ala His Ile Gln Leu Ser Asn Pro Ser
    150                 155                 160

TCA CTG TCA AAC ATC GAC TTT TAT GCC CAG GTG AGC GAC ATT ACA CCA     582
Ser Leu Ser Asn Ile Asp Phe Tyr Ala Gln Val Ser Asp Ile Thr Pro
165                 170                 175                 180

GCA GGT AGT GTG GTC CTT TCC CCG GGC CAA AAG AAT AAG GCA GGG ATG     630
Ala Gly Ser Val Val Leu Ser Pro Gly Gln Lys Asn Lys Ala Gly Met
                185                 190                 195

TCC CAA TGT GAC ATG CAC CCG GAA ATG GTC TCA CTC TGC CAA GAA AAC     678
Ser Gln Cys Asp Met His Pro Glu Met Val Ser Leu Cys Gln Glu Asn
            200                 205                 210

TTC CTT ATG GAC AAT GCC TAC TTC TGT GAG GCA GAT GCC AAA AAG TGC     726
Phe Leu Met Asp Asn Ala Tyr Phe Cys Glu Ala Asp Ala Lys Lys Cys
        215                 220                 225

CTC CCT GTG GCT CCT CAC ATC AAG GTT GAA TCA CAC ATA CAG CCA AGC     774
Leu Pro Val Ala Pro His Ile Lys Val Glu Ser His Ile Gln Pro Ser
    230                 235                 240

TTA AAC CAA GAG GAC ATT TAC ATC ACC ACA GAA AGC CTT ACC ACT GCT     822
Leu Asn Gln Glu Asp Ile Tyr Ile Thr Thr Glu Ser Leu Thr Thr Ala
245                 250                 255                 260
```

```
GCT GGG AGG CCT GGG ACA GGA GAA CAT GTT CCA GGT TCT GAG ATG CCT      870
Ala Gly Arg Pro Gly Thr Gly Glu His Val Pro Gly Ser Glu Met Pro
            265                 270                 275

GTC CCA GAC TAT ACC TCC ATT CAT ATA GTA CAG TCC CCA CAG GGC CTC      918
Val Pro Asp Tyr Thr Ser Ile His Ile Val Gln Ser Pro Gln Gly Leu
                280                 285                 290

ATA CTC AAT GCG ACT GCC TTG CCC TTG CCT GAC AAA GAG TTT CTC TCA      966
Ile Leu Asn Ala Thr Ala Leu Pro Leu Pro Asp Lys Glu Phe Leu Ser
            295                 300                 305

TCA TGT GGC TAT GTG AGC ACA GAC CAA CTG AAC AAA ATC ATG CCT         1011
Ser Cys Gly Tyr Val Ser Thr Asp Gln Leu Asn Lys Ile Met Pro
310                 315                 320

TAGCCTTTCT TTGG                                                      1025
```

(2) INFORMATION FOR SEQ ID NO:28:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:28:

```
Glu Gly Lys Leu Glu Glu Val Asn Pro Ile Leu Ala Ile His Asp Ser
 1               5                  10                  15

Tyr Lys Pro Glu Phe His Ser Asp Asp Ser Trp Val Glu Phe Ile Glu
                20                  25                  30

Leu Asp Ile Asp Glu Pro Asp Glu Lys Thr Glu Glu Ser Asp Thr Asp
            35                  40                  45

Arg Leu Leu Ser Ser Asp His Glu Lys Ser His Ser Asn Leu Gly Val
        50                  55                  60

Lys Asp Gly Asp Ser Gly Arg Thr Ser Cys Cys Glu Pro Asp Ile Leu
65                  70                  75                  80

Glu Thr Asp Phe Asn Ala Asn Asp Ile His Glu Gly Thr Ser Glu Val
                85                  90                  95

Ala Gln Pro Gln Arg Leu Lys Gly Glu Ala Asp Leu Leu Cys Leu Asp
            100                 105                 110

Gln Lys Asn Gln Asn Asn Ser Pro Tyr His Asp Ala Cys Pro Ala Thr
        115                 120                 125

Gln Gln Pro Ser Val Ile Gln Ala Glu Lys Asn Lys Pro Gln Pro Leu
    130                 135                 140

Pro Thr Glu Gly Ala Glu Ser Thr His Gln Ala His Ile Gln Leu
145                 150                 155                 160

Ser Asn Pro Ser Ser Leu Ser Asn Ile Asp Phe Tyr Ala Gln Val Ser
                165                 170                 175

Asp Ile Thr Pro Ala Gly Ser Val Val Leu Ser Pro Gly Gln Lys Asn
            180                 185                 190

Lys Ala Gly Met Ser Gln Cys Asp Met His Pro Glu Met Val Ser Leu
        195                 200                 205

Cys Gln Glu Asn Phe Leu Met Asp Asn Ala Tyr Phe Cys Glu Ala Asp
    210                 215                 220

Ala Lys Lys Cys Leu Pro Val Ala Pro His Ile Lys Val Glu Ser His
225                 230                 235                 240

Ile Gln Pro Ser Leu Asn Gln Glu Asp Ile Tyr Ile Thr Thr Glu Ser
                245                 250                 255
```

```
Leu Thr Thr Ala Ala Gly Arg Pro Gly Thr Gly Glu His Val Pro Gly
            260                 265                 270

Ser Glu Met Pro Val Pro Asp Tyr Thr Ser Ile His Ile Val Gln Ser
        275                 280                 285

Pro Gln Gly Leu Ile Leu Asn Ala Thr Ala Leu Pro Leu Pro Asp Lys
    290                 295                 300

Glu Phe Leu Ser Ser Cys Gly Tyr Val Ser Thr Asp Gln Leu Asn Lys
305                 310                 315                 320

Ile Met Pro
```

(2) INFORMATION FOR SEQ ID NO:29:

(i) SEQUENCE CHARACTERISTICS:
        (A) LENGTH: 1025 base pairs
        (B) TYPE: nucleic acid
        (C) STRANDEDNESS: unknown
        (D) TOPOLOGY: unknown (ix) FEATURE:
        (A) NAME/KEY: CDS
        (B) LOCATION: 43..702

(xi) SEQUENCE DESCRIPTION: SEQ ID NO:29:

```
GAGTTTCTTT TCATAGATCT TCATTTTCTT TCTATTTTCT AG GAA GGA AAA TTA           54
                                              Glu Gly Lys Leu
                                                1

GAG GAG GTG AAC ACA ATC TTA GCC ATT CAT GAT AGC TAT AAA CCC GAA         102
Glu Glu Val Asn Thr Ile Leu Ala Ile His Asp Ser Tyr Lys Pro Glu
  5              10                  15                  20

TTC CAC AGT GAT GAC TCT TGG GTT GAA TTT ATT GAG CTA GAT ATT GAT         150
Phe His Ser Asp Asp Ser Trp Val Glu Phe Ile Glu Leu Asp Ile Asp
                25                  30                  35

GAG CCA GAT GAA AAG ACT GAG GAA TCA GAC ACA GAC AGA CTT CTA AGC         198
Glu Pro Asp Glu Lys Thr Glu Glu Ser Asp Thr Asp Arg Leu Leu Ser
            40                  45                  50

AGT GAC CAT GAG AAA TCA CAT AGT AAC CTA GGG GTG AAG GAT GGC GAC         246
Ser Asp His Glu Lys Ser His Ser Asn Leu Gly Val Lys Asp Gly Asp
        55                  60                  65

TCT GGA CGT ACC AGC TGT TGT GAA CCT GAC ATT CTG GAG ACT GAT TTC         294
Ser Gly Arg Thr Ser Cys Cys Glu Pro Asp Ile Leu Glu Thr Asp Phe
    70                  75                  80

AAT GCC AAT GAC ATA CAT GAG GGT ACC TCA GAG GTT GCT CAG CCA CAG         342
Asn Ala Asn Asp Ile His Glu Gly Thr Ser Glu Val Ala Gln Pro Gln
85                  90                  95                 100

AGG TTA AAA GGG GAA GCA GAT CTC TTA TGC CTT GAC CAG AAG AAT CAA         390
Arg Leu Lys Gly Glu Ala Asp Leu Leu Cys Leu Asp Gln Lys Asn Gln
                105                 110                 115

AAT AAC TCA CCT TAT CAT GAT GCT TGC CCT GCT ACT CAG CAG CCC AGT         438
Asn Asn Ser Pro Tyr His Asp Ala Cys Pro Ala Thr Gln Gln Pro Ser
            120                 125                 130

GTT ATC CAA GCA GAG AAA AAC AAA CCA CAA CCA CTT CCT ACT GAA GGA         486
Val Ile Gln Ala Glu Lys Asn Lys Pro Gln Pro Leu Pro Thr Glu Gly
        135                 140                 145

GCT GAG TCA ACT CAC CAA GCT GCC CAT ATT CAG CTA AGC AAT CCA AGT         534
Ala Glu Ser Thr His Gln Ala Ala His Ile Gln Leu Ser Asn Pro Ser
    150                 155                 160

TCA CTG TCA AAC ATC GAC TTT TAT GCC CAG GTG AGC GAC ATA ACA CCA         582
Ser Leu Ser Asn Ile Asp Phe Tyr Ala Gln Val Ser Asp Ile Thr Pro
165                 170                 175                 180

GCA GGT AGT GTG GTC CTT TCC CCG GGC CAA AAG AAT AAG GCA GGG ATG         630
Ala Gly Ser Val Val Leu Ser Pro Gly Gln Lys Asn Lys Ala Gly Met
```

```
                        185                  190                  195
TCC CAA TGT GAC ATG CAC CCG GAA ATG GTC TCA CTC TGC CAA GAA AAC       678
Ser Gln Cys Asp Met His Pro Glu Met Val Ser Leu Cys Gln Glu Asn
            200                  205                  210

TTC CTT ATG GAC AAT GCC TAC TTC TGAGAGGCAG ATGCCAAAAA GTGCCTCCCT      732
Phe Leu Met Asp Asn Ala Tyr Phe
        215                 220

GTGGCTCCTC ACATCAAGGT TGAATCACAC ATACAGCCAA GCTTAAACCA AGAGGACATT     792

TACATCACCA CAGAAAGCCT TACCACTGCT GCTGGGAGGC CTGGGACAGG AGAACATGTT     852

CCAGGTTCTG AGATGCCTGT CCCAGACTAT ACCTCCATTC ATATAGTACA GTCCCCACAG     912

GGCCTCATAC TCAATGCGAC TGCCTTGCCC TTGCCTGACA AAGAGTTTCT CTCATCATGT     972

GGCTATGTGA GCACAGACCA ACTGAACAAA ATCATGCCTT AGCCTTTCTT TGG          1025

(2) INFORMATION FOR SEQ ID NO:30:

(i) SEQUENCE CHARACTERISTICS:
        (A) LENGTH: 220 amino acids
        (B) TYPE: amino acid
        (D) TOPOLOGY: linear (ii) MOLECULE TYPE: protein (xi) SEQUENCE DESCRIPTION: SEQ ID NO:30:

Glu Gly Lys Leu Glu Val Asn Thr Ile Leu Ala Ile His Asp Ser
 1               5                  10                  15

Tyr Lys Pro Glu Phe His Ser Asp Asp Ser Trp Val Glu Phe Ile Glu
                20                  25                  30

Leu Asp Ile Asp Glu Pro Asp Glu Lys Thr Glu Glu Ser Asp Thr Asp
            35                  40                  45

Arg Leu Leu Ser Ser Asp His Glu Lys Ser His Ser Asn Leu Gly Val
    50                  55                  60

Lys Asp Gly Asp Ser Gly Arg Thr Ser Cys Cys Glu Pro Asp Ile Leu
65                  70                  75                  80

Glu Thr Asp Phe Asn Ala Asn Asp Ile His Glu Gly Thr Ser Glu Val
                85                  90                  95

Ala Gln Pro Gln Arg Leu Lys Gly Glu Ala Asp Leu Leu Cys Leu Asp
            100                 105                 110

Gln Lys Asn Gln Asn Asn Ser Pro Tyr His Asp Ala Cys Pro Ala Thr
        115                 120                 125

Gln Gln Pro Ser Val Ile Gln Ala Glu Lys Asn Lys Pro Gln Pro Leu
    130                 135                 140

Pro Thr Glu Gly Ala Glu Ser Thr His Gln Ala Ala His Ile Gln Leu
145                 150                 155                 160

Ser Asn Pro Ser Ser Leu Ser Asn Ile Asp Phe Tyr Ala Gln Val Ser
                165                 170                 175

Asp Ile Thr Pro Ala Gly Ser Val Val Leu Ser Pro Gly Gln Lys Asn
            180                 185                 190

Lys Ala Gly Met Ser Gln Cys Asp Met His Pro Glu Met Val Ser Leu
        195                 200                 205

Cys Gln Glu Asn Phe Leu Met Asp Asn Ala Tyr Phe
    210                 215                 220

(2) INFORMATION FOR SEQ ID NO:31:

(i) SEQUENCE CHARACTERISTICS:
        (A) LENGTH: 22 base pairs
```

```
        (B) TYPE: nucleic acid
        (C) STRANDEDNESS: unknown
        (D) TOPOLOGY: unknown (xi) SEQUENCE DESCRIPTION: SEQ ID NO:31:

GAAACTGTGC TTCAACTAGT CG                                              22

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (xi) SEQUENCE DESCRIPTION: SEQ ID NO:32:

GGTCTAACAC AACTGGTACA G                                               21

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (xi) SEQUENCE DESCRIPTION: SEQ ID NO:33:

CAACTGGACT TTACTGAACG                                                 20

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (xi) SEQUENCE DESCRIPTION: SEQ ID NO:34:

TGCTATTAAA TACGTAGC                                                   18

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (xi) SEQUENCE DESCRIPTION: SEQ ID NO:35:

GGATAAGGAA TATGAAGTGC                                                 20

(2) INFORMATION FOR SEQ ID NO:36:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (xi) SEQUENCE DESCRIPTION: SEQ ID NO:36:

GCTGGTGTAA TGTCGCTCA                                                  19

(2) INFORMATION FOR SEQ ID NO:37:

(i) SEQUENCE CHARACTERISTICS:
        (A) LENGTH: 18 base pairs
        (B) TYPE: nucleic acid
```

```
        (C) STRANDEDNESS: unknown
        (D) TOPOLOGY: unknown (xi) SEQUENCE DESCRIPTION: SEQ ID NO:37:

ACACTTCCTC AGATGAGC                                                    18

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (xi) SEQUENCE DESCRIPTION: SEQ ID NO:38:

CACTGTGGAA TTCGGGTTTA                                                  20

(2) INFORMATION FOR SEQ ID NO:39:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

TCGTGGGCTT TACCTTAC                                                    18

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

CAAAACACTG AGGGTGGA                                                    18

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

TACACAGGGT CATATCAGAT TG                                               22

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

CTATTCCAGT TACTACCATC CC                                               22
```

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

CTGATTTCAT GCCTTGCC                                                  18

(2) INFORMATION FOR SEQ ID NO:44:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

AGAAAGGCAT GATGGTGG                                                  18

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

ACTTAAGCTA CAACATGATT                                           20

(2) INFORMATION FOR SEQ ID NO:46:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

GCTTCCCCAT TTATTTAGT                                              19

(2) INFORMATION FOR SEQ ID NO:47:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

ATGCTCTGTT GAATTGCAC                                              19

(2) INFORMATION FOR SEQ ID NO:48:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:48:

GTGTAAGGTG TAGCAACAT                                       19

(2) INFORMATION FOR SEQ ID NO:49:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

GACTCTTTGG CCAATATG                                        18

(2) INFORMATION FOR SEQ ID NO:50:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

AAGCCAGGTT AGCTACTA                                        18

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

GAAACTGTGC TTCAACTAGT C                                    21

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

GGTCTAACAC AACTGGTACA                                      20

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:53:

ATGTAGCTTT TAACATCTCA A                                              21

(2) INFORMATION FOR SEQ ID NO:54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

ATGACAGGAG TCTTCAGG                                                  18

(2) INFORMATION FOR SEQ ID NO:55:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

GAGTTTCTTT TCATAGATCT TC                                             22

(2) INFORMATION FOR SEQ ID NO:56:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

TTAACCTCTG TGGCTGAG                                                  18

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

ACATGAGGGT ACCTCAGA                                                  18

(2) INFORMATION FOR SEQ ID NO:58:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (xi) SEQUENCE DESCRIPTION: SEQ ID NO:58:

```
CAGAAGTAGG CATTGTCC                                                    18

(2) INFORMATION FOR SEQ ID NO:59:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:59:

GGAAATGGTC TCACTCTG                                                    18

(2) INFORMATION FOR SEQ ID NO:60:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:60:

CCAAAGAAAG GCTAAGGC                                                    18

(2) INFORMATION FOR SEQ ID NO:61:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:61:

GTCCTACAGG TATGGATCTC T                                                21

(2) INFORMATION FOR SEQ ID NO:62:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:62:

GAATATCTGC ATTGCGTGGT G                                                21

(2) INFORMATION FOR SEQ ID NO:63:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:63:

CTGGTATAGA ACAGCTGTAT G                                                21

(2) INFORMATION FOR SEQ ID NO:64:
```

```
    (i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

ATTCTTCTAA GGAGCCTAAA TTCACCA                                          27

(2) INFORMATION FOR SEQ ID NO:65:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

CCACCATTGC TAGTTAGCTT G                                                21

(2) INFORMATION FOR SEQ ID NO:66:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

ATGGACTCAA GAATGGAAAG AATG                                             24

(2) INFORMATION FOR SEQ ID NO:67:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

CACCACGCAA TGCAGATATT C                                                21

(2) INFORMATION FOR SEQ ID NO:68:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

CTCATGGTCA CTGCTTAGAA G                                                21

(2) INFORMATION FOR SEQ ID NO:69:

(i) SEQUENCE CHARACTERISTICS:
        (A) LENGTH: 21 base pairs
        (B) TYPE: nucleic acid
```

(C) STRANDEDNESS: single
            (D) TOPOLOGY: linear (ii) MOLECULE TYPE: DNA (genomic)

(xi) SEQUENCE DESCRIPTION: SEQ ID NO:69:

GTTACATAGA GCACCTCACT G                                              21

(2) INFORMATION FOR SEQ ID NO:70:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:70:

ATGGACCCTA TATTGACAAC ATC                                            23

(2) INFORMATION FOR SEQ ID NO:71:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:71:

CCTTTAATCT TTGGAACTGG AAC                                            23

(2) INFORMATION FOR SEQ ID NO:72:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:72:

GGGCTAACAG TGATGCTATT T                                              21

(2) INFORMATION FOR SEQ ID NO:73:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:73:

GCTTAGAAGT CTGTCTGTGT C                                              21

(2) INFORMATION FOR SEQ ID NO:74:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:74:

GCTAGATATT GATGAGCCAG A                                              21

(2) INFORMATION FOR SEQ ID NO:75:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

GCTAAGGCAT GATTTTGTTC A                                              21

(2) INFORMATION FOR SEQ ID NO:76:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

GTCGATGTTT GACAGTGAAC T                                              21

(2) INFORMATION FOR SEQ ID NO:77:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

GAAGGAGCTG AGTCAACTCA C                                              21

(2) INFORMATION FOR SEQ ID NO:78:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

GCTTGGCTGT ATGTGTGATT C                                              21

(2) INFORMATION FOR SEQ ID NO:79:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:79:

TACTTCTGTG AGGCAGATGC C                    21